(12) United States Patent
Hachiya et al.

(10) Patent No.: US 9,284,295 B2
(45) Date of Patent: *Mar. 15, 2016

(54) TETRAHYDROBENZOTHIOPHENE COMPOUND

(71) Applicant: Astellas Pharma Inc., Chuo-ku (JP)

(72) Inventors: Shunichiro Hachiya, Chuo-ku (JP); Masanori Miura, Chuo-ku (JP); Yoshimasa Imamura, Chuo-ku (JP); Daisuke Kaga, Chuo-ku (JP); Ippei Sato, Chuo-ku (JP); Hiroyuki Moritomo, Chuo-ku (JP); Koji Kato, Chuo-ku (JP); Kazuhiro Terai, Chuo-ku (JP); Yoh Terada, Chuo-ku (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/229,146

(22) Filed: Mar. 28, 2014

(65) Prior Publication Data

US 2014/0329802 A1    Nov. 6, 2014

Related U.S. Application Data

(63) Continuation of application No. 13/661,545, filed on Oct. 26, 2012, now Pat. No. 8,729,068, which is a continuation-in-part of application No. PCT/JP2011/060261, filed on Apr. 27, 2011.

(30) Foreign Application Priority Data

Apr. 28, 2010    (JP) .................................. 2010-104044

(51) Int. Cl.
| | |
|---|---|
| *C07D 333/68* | (2006.01) |
| *A61K 31/381* | (2006.01) |
| *A61K 31/4025* | (2006.01) |
| *A61K 31/4436* | (2006.01) |
| *C07D 333/66* | (2006.01) |
| *A61K 31/444* | (2006.01) |
| *A61K 31/4535* | (2006.01) |
| *A61K 31/454* | (2006.01) |
| *A61K 31/496* | (2006.01) |

(Continued)

(52) U.S. Cl.
CPC ............ *C07D 333/66* (2013.01); *A61K 31/381* (2013.01); *A61K 31/4025* (2013.01); *A61K 31/444* (2013.01); *A61K 31/4436* (2013.01); *A61K 31/454* (2013.01); *A61K 31/4535* (2013.01); *A61K 31/496* (2013.01); *A61K 31/5377* (2013.01); *A61K 31/55* (2013.01); *A61K 31/63* (2013.01); *A61K 31/7042* (2013.01); *C07D 333/68* (2013.01); *C07D 409/12* (2013.01)

(58) Field of Classification Search
CPC ............ A61K 31/381; A61K 31/4436; A61K 31/444; A61K 31/4535; A61K 31/454; A61K 31/55; A61K 31/63; C07D 409/12
See application file for complete search history.

(56) References Cited

U.S. PATENT DOCUMENTS

| 2006/0217426 A1 | 9/2006 | Eto et al. |
| 2009/0163545 A1 | 6/2009 | Goldfarb |
| 2013/0029973 A1 | 1/2013 | Hachiya et al. |

FOREIGN PATENT DOCUMENTS

| EP | 1 614 676 A1 | 1/2006 |
| JP | 2007 131532 | 5/2007 |

(Continued)

OTHER PUBLICATIONS

Nakamura, I. et al. Transition-Metal-Catalyzed Reactions in Heterocyclic Synthesis. Chem. Rev. 2004, vol. 104, p. 2127.*

(Continued)

*Primary Examiner* — Savitha Rao
(74) *Attorney, Agent, or Firm* — Oblon, McClelland, Maier & Neustadt, L.L.P.

(57) ABSTRACT

The purpose is to provide a compound which has an intestinal phosphate transporter (NPT-IIb) inhibitory action and is useful as an active ingredient of an agent for treating and/or preventing hyperphosphatemia.

A tetrahydrobenzothiophene compound of the following formula (I) has NPT-IIb inhibitory action and can be used as an agent for treating and/or preventing hyperphosphatemia:

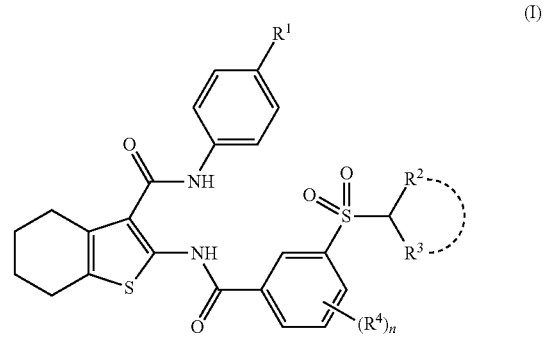

(I)

wherein, $R^1$ represents —O-lower alkyl, -lower alkylene-phenyl, or the like; $R^2$ and $R^3$ are the same as or different from each other and represent H, lower alkyl, cycloalkyl, aryl, heteroaryl or the like, or, $R^2$ and $R^3$ may be combined with a nitrogen atom to which they bind to form 5- to 7-membered saturated cyclic amino; $R^4$'s are the same as or different from each other and represent halogen, lower alkyl; and n represents 0 to 2.

9 Claims, No Drawings

(51) Int. Cl.
  *A61K 31/5377* (2006.01)
  *A61K 31/55* (2006.01)
  *A61K 31/63* (2006.01)
  *A61K 31/7042* (2006.01)
  *C07D 409/12* (2006.01)

(56) References Cited

FOREIGN PATENT DOCUMENTS

| | | |
|---|---|---|
| WO | 03 048134 | 6/2003 |
| WO | 2004 069149 | 8/2004 |
| WO | 2004 085382 | 10/2004 |
| WO | 2005 023818 | 3/2005 |
| WO | 2005 033102 | 4/2005 |
| WO | 2006 026619 | 3/2006 |
| WO | 2006 044826 | 4/2006 |
| WO | 2006 093518 | 9/2006 |
| WO | 2007 009661 | 1/2007 |
| WO | 2009 079373 | 6/2009 |
| WO | 2009 087564 | 7/2009 |
| WO | 2010 003533 | 1/2010 |
| WO | 2012 006475 | 1/2012 |

OTHER PUBLICATIONS

Anderson (Chem and Biol 10:787-797, 2003).*
Thiel (Nature Biotechnol 2:513-519, 2004).*
"KDIGO Clinical Practice Guideline for the Diagnosis, Evaluation, Prevention, and Treatment of Chronic Kidney Disease-Mineral and Bone Disorder (CKD-MBD)," Kidney International, vol. 76, Supplement 113, Total 71 Pages, (Aug. 2009).
Sabbagh, Y., et al., "Intestinal Npt2b Plays a Major Role in Phosphate Absorption and Homeostasis," Journal of the American Society of Nephrology, vol. 20, pp. 2348-2358, (2009).
Chemical Abstracts Services (CAS), Report for CAS RN 939927-55-6 (Export of SciFinder search result) (dated 2012), Total 1 Page.
Chemincal Abstracts Services (CAS), Report for CAS RN 1099306-08-7 (Export of SciFinder search result) (dated 2012) Total 1 Page.
Chemical Abstracts Services (CAS), Report for CAS RN 851297-80-8 (Export of SciFinder search result) (dated 2012) Total 2 Pages.
International Search Report Issued May 31, 2011 in PCT/JP11/60261.
Office Action issued Apr. 3, 2013 in Mexican Application No. MX/a/2012/012421 filed Apr. 27, 2011 (with English-language translation).
Extended European Search Report issued Jul. 18, 2013 in Patent Application No. 11775050.5.
Database PubChem [Online] NCBI; Database accession No. CID-4869359, XP002699994, Sep. 17, 2005, 6 pages.
Combined Office Action and Search Report issued Jun. 25, 2013 in Chinese Patent Application No. 201180021504.6 (with English translation).
Office Action issued Sep. 23, 2013 in Eurasian Patent Application No. 201291121/28 with English language translation.

* cited by examiner

TETRAHYDROBENZOTHIOPHENE COMPOUND

CROSS REFERENCE TO RELATED APPLICATIONS

This application is a continuation of U.S. Ser. No. 13/661,545, filed Oct. 26, 2012, which is a continuation-in-part of International Application No. PCT/JP2011/060261 filed on Apr. 27, 2011, which claims the benefit of Japan Patent Application. No. 2010-104044 filed on Apr. 28, 2010. The entire disclosures of International Application No. PCT/JP2011/060261 and Japan Patent Application. No. 2010-104044 are incorporated by reference herein.

TECHNICAL FIELD

The present invention relates to a tetrahydrobenzothiophene compound which is useful as an active ingredient of a pharmaceutical composition, for example, a pharmaceutical composition for treating hyperphosphatemia.

BACKGROUND ART

Phosphorus is an essential element in the maintenance of life and plays very important roles in various physiological functions. Phosphorus is taken up in the form of phosphate through the gastrointestinal tract from food, and most of the phosphorous is excreted by incorporation into urine, whereby its total amount in a living body is maintained and regulated. It is known that in the process of formation of urine, substantially most of phosphate is filtered at the glomerulus and only a required amount thereof is reabsorbed in the tubules. Accordingly, if the filtration ability of the glomerulus decreases as renal failure progresses, excretion of phosphorus becomes insufficient. Thus, an abnormal increment of the serum phosphorus concentration, that is, hyperphosphatemia develops.

Hyperphosphatemia induces an concentration increase of FGF-23 in the blood which is a promoting factor for phosphorous excretion in urine, or that of parathyroid hormone (iPTH). An abnormal rise in iPTH is one of the complications of renal failure, called hyperparathyroidism, which also causes ectopic calcification or the like through the activation of bone metabolism. In this way, hyperphosphatemia becomes one of the causes or aggravating factors of other complications associated with decreased renal function, through the action of compensatory functions of the body accompanying hyperphosphatemia.

As described above, it is thought that hyperphosphatemia inducing various complications of renal failure becomes a cause of decrease in QOL for patients with renal failure due to bone fracture, bone pain, or the like, or the death of patients with renal failure due to cardiovascular diseases caused by calcification of the cardiovascular system. In this regard, hyperphosphatemia becomes a very significant problem in clinical practice.

Currently, for the treatment of hyperphosphatemia, phosphate binders, for example, various calcium salt preparations typically exemplified by precipitated calcium carbonate, a polymer typically exemplified by sevelamer hydrochloride, or metal salt preparations such as lanthanum carbonate, aluminum hydroxide, an iron preparation, and the like are used for the purpose of inhibiting the phosphorus absorption from the gastrointestinal tract. These drugs, however, have various problems, such as poor dose adherence due to the requirement for several grams per day, gastrointestinal symptoms such as constipation/diarrhea, and the like, elevated concentration of calcium in the serum, accumulation of various metals, and the like, and thus, there is a demand for development of a novel agent for treating hyperphosphatemia having modifications of these weak points (see, for example, Non-Patent Document 1).

On the other hand, it is thought that absorption and excretion of phosphorus are associated with phosphate transporters presenting on the brush border membrane of the gastrointestinal tract and kidney tubules. A number of the phosphate transporters have been reported, but among them, NPT-IIb and NPT-IIa play a major role in phosphate absorption in the gastrointestinal tract and phosphate reabsorption in the kidney, respectively. Moreover, these molecules have also been reported as a sodium and phosphate cotransporter. From this, it is thought that the phosphorus absorption from the gastrointestinal tract can be inhibited by inhibition of the function of NPT-IIb (see, for example, Non-Patent Document 2).

From the above, it is suggested that an NPT-IIb inhibiting agent is promising as a medicament for treating hyperphosphatemia with novel mechanism of actions which will replace various phosphate binders that have currently been used in clinical practice.

In Patent Document 1, there is disclosed a compound having an NPT-IIb inhibitory action, which is represented by the general formula (A) and specifically, a compound having a tetrahydrobenzothiophene skeleton is also disclosed, but its substituents at the 2-position and the 3-position are each different from those of the compound of the present invention. That is, from a viewpoint that its substituent at the 3-position is a hydrazinocarbonyl group, it is clearly different from the compound of the present invention in which the substituent at the 3-position is a phenylcarbamoyl group. Further, a substituent at the 2-position is a benzoylamino group, but the substituents of this benzene ring do not include a sulfamoyl group as in the compound of the present invention.

[Chem. 1]

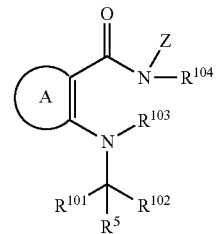

(A)

(wherein A represents a 5- to 9-membered unsaturated heterocycle or the like, $R^5$ represents an aryl group or the like, $R^{101}$ and $R^{102}$, combined together, represent =O, or the like, and Z represents a compound represented by the following formula (i), (ii), or (iii). For the other symbols in the formula, refer to the corresponding patent publications).

[Chem. 2]

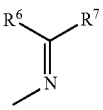

(i)

-continued

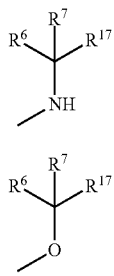

(ii)

(iii)

Furthermore, in Patent Documents 2 and 3, there are disclosed compounds having a NPT-IIb inhibitory action, which have a triazole skeleton and a quinazolinone skeleton, respectively, but there is not disclosed a compound having a tetrahydrobenzothiophene skeleton as in the compound of the present invention.

In Patent Document 4, there is disclosed a compound represented by the general formula (B), but there is not disclosed a compound in which the substituent at the 2-position of a tetrahydrobenzothiophene ring is a sulfamoylbenzoylamino group as in the compound of the present invention.

[Chem. 3]

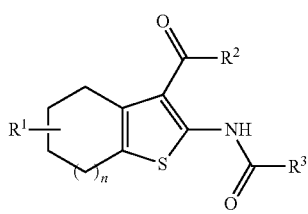

(B)

(wherein $R^2$ represents an optionally substituted phenylamino, or the like, $R^3$ represents an optionally substituted phenyl, or the like, and n represents 1 or the like. For the other symbols in the formula, refer to the corresponding patent publications.)

In Patent Document 5, for example, there is disclosed a compound represented by the formula (C) or the like, but there is neither disclosed a compound having phenyl instead of cyclopropyl as a substituent of carbamoyl, which is a substituent at the 3-position of the tetrahydrobenzothiophene ring nor a compound having a sulfamoyl group as a substituent of a benzene ring of a benzoylamino group, which is a substituent at the 2-position.

[Chem. 4]

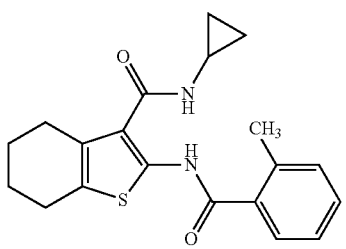

(C)

In Patent Document 6, there is disclosed a compound represented by the formula (D) or the like, in Patent Document 7, there is disclosed a compound represented by the formula (E) or the like, and in Patent Document 8, there is disclosed a compound represented by the formula (F) or the like. However, there is not disclosed a compound having a sulfamoyl group as a substituent of a benzene ring of a benzoylamino group, which is a substituent at the 2-position of a tetrahydrobenzothiophene ring.

[Chem. 5]

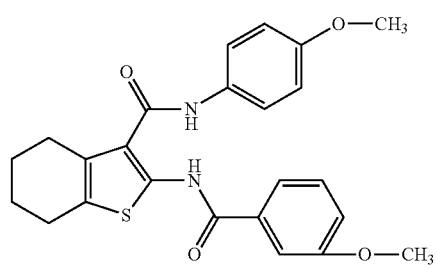

(D)

[Chem. 6]

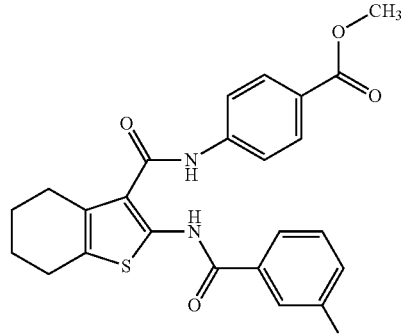

(E)

[Chem. 7]

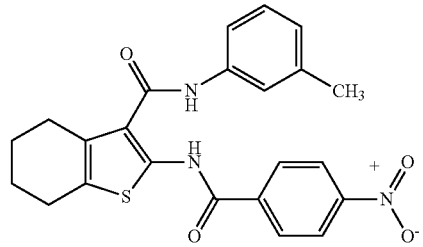

(F)

In Patent Document 9, for example, there is disclosed a compound represented by the formula (G) or the like, but there is neither disclosed a compound having a benzene ring as a substituent of carbamoyl, which is a substituent at the 3-position of the tetrahydrobenzothiophene ring nor a compound having a sulfamoyl group as a substituent of benzene ring of a benzoylamino group, which is a substituent at the 2-position.

[Chem. 8]

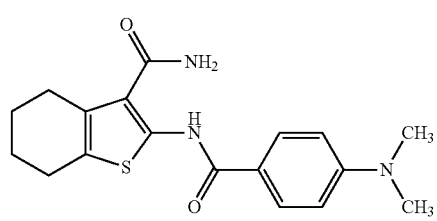

(G)

In Patent Document 10, there is disclosed a compound represented by the formula (H) or the like, but there is neither disclosed a compound having phenyl as a substituent of carbamoyl which is a substituent at the 3-position of the tetrahydrobenzothiophene ring nor a compound having sulfamoylphenyl instead of cyclobutyl of a cyclobutylcarbonylamino group which is a substituent at the 2-position.

[Chem. 9]

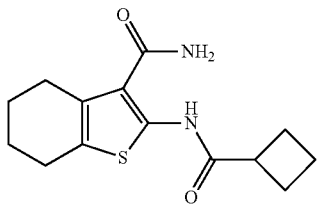

(H)

In Patent Document 11, there is disclosed a compound represented by the general formula (K-a), but it is different from the compound of the present invention in that it does not include a tetrahydrobenzothiophene skeleton. There is further disclosed a compound represented by the general formula (K-b), which can include a tetrahydrobenzothiophene skeleton. However, such a compound in which the substituent at the 2-position is a substituted carbamoyl group is different from the compound of the present invention in which the substituent at the 2-position is a substituted carbonylamino group, and such a compound in which the substituent at the 3-position is a pyrrolidylcarbonylamino group is also different from the compound of the present invention in which the substituent at the 3-position is a phenylcarbamoyl group.

[Chem. 10]

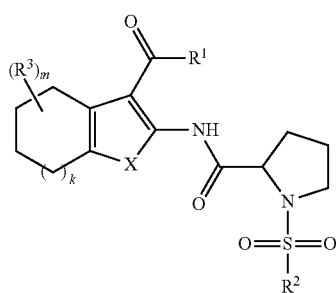

(K-a)

[Chem. 11]

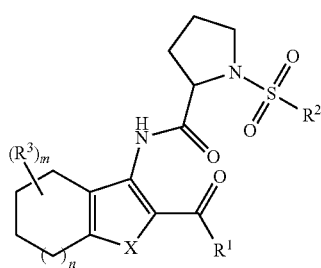

(K-b)

(wherein X represents S or O, and $R^1$ represents —NH($C_1$-$C_4$ alkyl), the following group:

[Chem. 12]

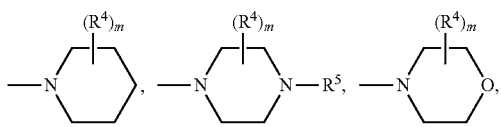

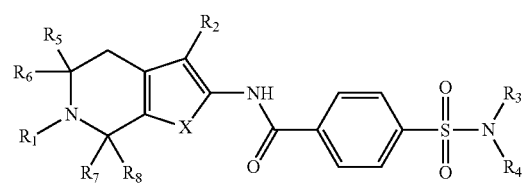

-continued or the like. $R^2$ represents $C_1$-$C_{10}$ alkyl, $C_3$-$C_8$ cycloalkyl, phenyl, 5 to 7-membered heteroaryl, or the like, k represents an integer of 2 to 4, $R^3$ represents optionally substituted phenyl, or the like, and n represents an integer of 0 to 4. For the other symbols in the formula, refer to the corresponding patent publications).

In Patent Document 12, there is disclosed a compound represented by the general formula (L), but such a compound which has a tetrahydrothieno[2,3-c]pyridine skeleton is different from the compound of the present invention which has a tetrahydrobenzothiophene skeleton. In addition, there is not specifically disclosed a compound in which the substituent at the 2-position is a phenylaminocarbonyl group.

[Chem. 13]

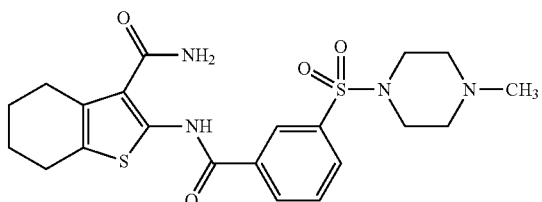

(L)

(wherein $R_2$ represents arylaminocarbonyl in which aryl is optionally substituted, or the like. For the other symbols in the formula, refer to the corresponding patent publications).

In Patent Document 13, there is disclosed a compound represented by the formula (M-a) or the formula (M-b), but there is not disclosed a compound having a benzene ring as a substituent of carbamoyl, which is a substituent at the 3-position of the tetrahydrobenzothiophene ring.

[Chem. 14]

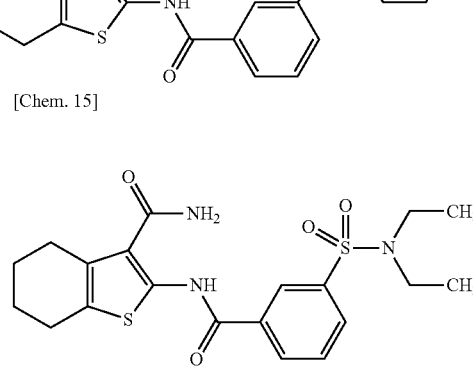

(M-a)

[Chem. 15]

(M-b)

Further, in Patent Documents 4 to 13, it is neither suggested nor disclosed that the compound has an NPT-IIb inhibitory action or is used for preventing or treating hyperphosphatemia.

In addition, there is a compound represented by a formula (N), the formula (O) or the formula (P) as a compound known according to the database. The compound represented by the formula (N) or the formula (O) does not have a benzene ring as a substituent of carbamoyl, which is a substituent at the 3-position of the tetrahydrobenzothiophene ring. Further, the compound represented by the formula (P) is different from the compound of the formula (I). In addition, it is neither suggested nor disclosed that the compound has an NPT-IIb inhibitory action or is used for preventing or treating hyperphosphatemia.

[Chem. 16]

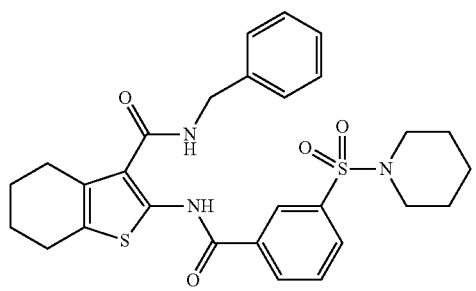

(N)

[Chem. 17]

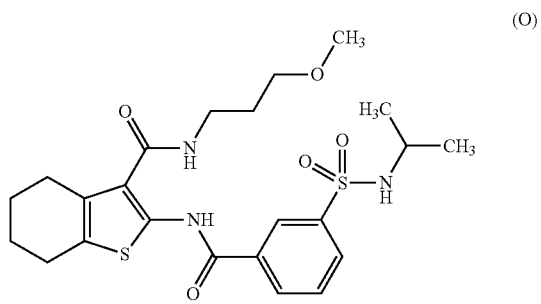

(O)

[Chem. 18]

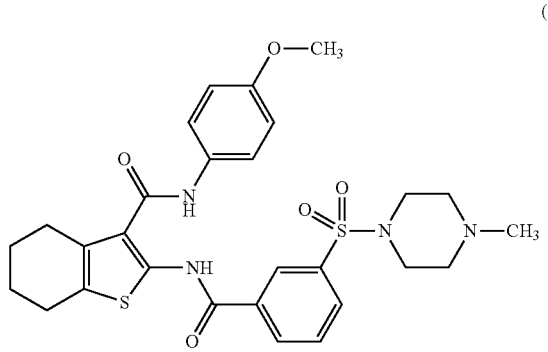

(P)

RELATED ART

Patent Document

[Patent Document 1] Pamphlet of International Publication WO 2004/085382
[Patent Document 2] Pamphlet of International Publication WO 2003/048134
[Patent Document 3] JP-A-No. 2007-131532
[Patent Document 4] Pamphlet of International Publication WO 2009/079373
[Patent Document 5] Pamphlet of International Publication WO 2007/009661
[Patent Document 6] Pamphlet of International Publication WO 2006/093518
[Patent Document 7] Pamphlet of International Publication WO 2006/044826
[Patent Document 8] Pamphlet of International Publication WO 2006/026619
[Patent Document 9] Pamphlet of International Publication WO 2005/033102
[Patent Document 10] Pamphlet of International Publication WO 2005/023818
[Patent Document 11] Pamphlet of International Publication WO 2009/087564
[Patent Document 12] Pamphlet of International Publication WO 2004/069149
[Patent Document 13] Specification of U.S. Patent Application Publication No. 2009/0163545

Non-Patent Document

[Non-Patent Document 1] "KDIGO Clinical Guideline for the Diagnosis, Evaluation, Prevention, and Treatment of Chronic Kidney Disease—Mineral and Bone Disorder (CKD-MBD)", Kidney International, 76, Supplement 113 (2009)
[Non-Patent Document 2] Journal of the American Society of Nephrology, 20: p. 2348-2358 (2009)

SUMMARY OF INVENTION

Problems to be Solved by the Invention

Provided is a compound which has an NPT-IIb inhibitory action and is useful as an active ingredient of a pharmaceutical composition for preventing or treating hyperphosphatemia.

Means for Solving the Problems

The present inventors have extensively studied a compound having an NPT-IIb inhibitory action, and as a result, they have found that the tetrahydrobenzothiophene compound of the present invention is useful as a compound having an NPT-IIb inhibitory action, thereby completing the present invention.

That is, the present invention relates to a compound of the formula (I) or a salt thereof, and a pharmaceutical composition comprising a compound of formula (I) or a salt thereof and an excipient:

[Chem. 19]

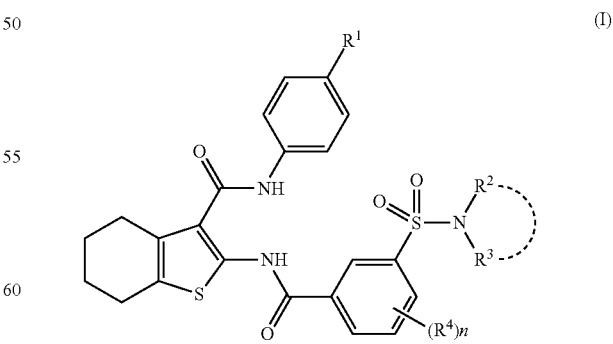

(I)

[wherein
$R^1$ represents —O-lower alkyl, -lower alkylene-phenyl, or -lower alkylene-pyridyl (in which phenyl or pyridyl may be substituted with carboxy or protected carboxy), R² and R³ are the same as or different from each other and represent H, lower alkyl, cycloalkyl, aryl, heteroaryl, nitrogen-containing saturated hetero ring, -lower alkylene-aryl, or -lower alkylene-heteroaryl (in which lower alkyl, cycloalkyl, aryl, heteroaryl, and nitrogen-containing saturated hetero ring may be substituted), or R² and R³ may be combined with a nitrogen atom to which they bind to form 5- to 7-membered saturated cyclic amino (in which the 5- to 7-membered saturated cyclic amino may be substituted), R⁴'s are the same as or different from each other and represent halogen, lower alkyl, —OH, —O-lower alkyl, —NO₂, or a group represented by the formula (II):

[Chem. 20]

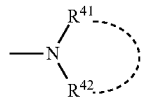

(II)

(wherein $R^{41}$ and $R^{42}$ are the same as or different from each other and represent H or lower alkyl which may be substituted, or $R^{41}$ and $R^{42}$ may be combined with a nitrogen atom to which they bind to form 5- to 7-membered saturated cyclic amino), and n represents 0 to 2, provided that N-(4-methoxyphenyl)-2-({3-[(4-methylpiperazin-1-yl)sulfonyl]benzoyl}amino)-4,5,6,7-tetrahydro-1-benzothiophene-3-carboxamide is excluded].

The present invention also relates to a compound of the formula (Ia) or a salt thereof, and a pharmaceutical composition comprising a compound of the formula (Ia) or a salt thereof and an excipient:

[Chem. 21]

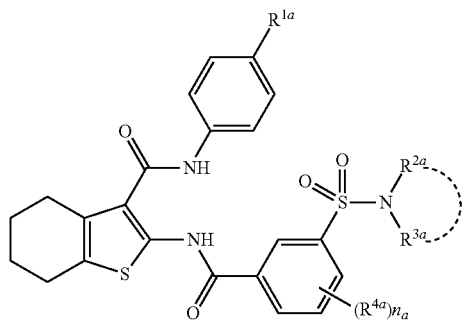

(Ia)

[wherein
$R^{1a}$ represents —O-lower alkyl, -lower alkylene-phenyl, or -lower alkylene-pyridyl (in which phenyl or pyridyl may be substituted with carboxy or protected carboxy), $R^{2a}$ and $R^{3a}$ are the same as or different from each other and represent H, lower alkyl, cycloalkyl, phenyl, pyridyl, -lower alkylene-phenyl, or -lower alkylene-pyridyl (in which the cycloalkyl, phenyl, or pyridyl may be substituted with carboxy or protected carboxy and the lower alkyl may be substituted with —O-lower alkyl, —[CH(—OH)]$_m$—H, carboxy, or protected carboxy), or $R^{2a}$ and $R^{3a}$ may be combined with an N atom to which they bind to form a 5- to 7-membered saturated cyclic amino (in which the 5- to 7-membered saturated cyclic amino may have substituent(s)), $R^{4a}$ represents halogen, lower alkyl, —OH, —O-lower alkyl, —NO₂, or a group represented by the formula (IIa):

[Chem. 22]

(IIa)

(wherein $R^{41a}$ and $R^{42a}$ are the same as or different from each other and represent H, or lower alkyl which may be substituted, or $R^{41a}$ and $R^{42a}$ may be combined with an N atom to which they bind to form 5- to 7-membered saturated cyclic amino), m represents 1 to 5, and $n_a$ represents 0 to 2, provided that N-(4-methoxyphenyl)-2-({3-[(4-methylpiperazin-1-yl)sulfonyl]benzoyl}amino)-4,5,6,7-tetrahydro-1-benzothiophene-3-carboxamide is excluded].

Furthermore, unless specifically described otherwise, in the case where the symbols in any of the formulas in the present specification are also used in other formulas, the same symbols denote the same meanings Furthermore, the present invention relates to a pharmaceutical composition for treating hyperphosphatemia, which includes a compound of the formula (I) or a salt thereof, or a compound of the formula (Ia) or a salt thereof. Further, the composition includes an agent for treating hyperphosphatemia, which includes a compound of the formula (I) or a salt thereof, or a compound of the formula (Ia) or a salt thereof.

The present invention further relates to use of the compound of the formula (I) or a salt thereof, or the compound of the formula (Ia) or a salt thereof, for preparation of a pharmaceutical composition for treating hyperphosphatemia, use of the compound of the formula (I) or a salt thereof, or the compound of the formula (Ia) or a salt thereof for treatment of hyperphosphatemia, a compound of the formula (I) or a salt thereof, or a compound of the formula (Ia) or a salt thereof for treating hyperphosphatemia, and a method for treating hyperphosphatemia, including administering to a subject an effective amount of the compound of the formula (I) or a salt thereof, or the compound of the formula (Ia) or a salt thereof. In addition, the "subjects" refer to humans or other animals in need of the prevention or treatment thereof, and in a certain embodiment, humans in need of the prevention or treatment thereof.

In addition, the compound of the formula (Ia) or a salt thereof is included in the compound of the formula (I) or a salt thereof. Accordingly, in the present specification, the description of the compound of the formula (I) also includes that of the compound of the formula (Ia).

Effects of the Invention

The compound of the formula (I), or a salt thereof, or the compound of the formula (Ia) or a salt thereof has an NPT-IIb inhibitory action and can be used as an agent for preventing and/or treating hyperphosphatemia or the like.

MODE FOR CARRYING OUT THE INVENTION

The "lower alkyl" refers to a straight or branched alkyl having 1 to 6 carbon atoms (hereinafter simply referred to as $C_{1-6}$), for example, methyl, ethyl, n-propyl, isopropyl, n-butyl, isobutyl, sec-butyl, tert-butyl, n-pentyl, n-hexyl, or the like, in another embodiment, methyl, ethyl, n-propyl, isopropyl, n-butyl, or isobutyl, in a further embodiment, methyl, or ethyl, and in a further embodiment, methyl.

The "lower alkylene" refers to a straight or branched $C_{1-6}$ alkylene, for example, methylene, ethylene, trimethylene, tetramethylene, pentamethylene, hexamethylene, propylene, methylmethylene, dimethylmethylene, ethylethylene, 1,2-dimethylethylene, 1,1,2,2-tetramethylethylene, or the like, in another embodiment, $C_{1-4}$ alkylene, in a further embodiment, ethylene or propylene, in a further embodiment methylene.

The "halogen" means F, Cl, Br, or I.

The "cycloalkyl" refers to a $C_{3-10}$ saturated hydrocarbon ring group, which may have bridge(s), and is, for example, cyclopropyl, cyclobutyl, cyclopentyl, cyclohexyl, cycloheptyl, cyclooctyl, adamantyl, or the like, in another embodiment, $C_{3-8}$ cycloalkyl, in a further embodiment, $C_{3-6}$ cycloalkyl, in a further embodiment, cyclopropyl, cyclobutyl, cyclopentyl or cyclohexyl, and in a further embodiment, cyclopropyl or cyclohexyl.

The "aryl" refers to a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 4-indenyl, 1-fluorenyl, or the like, and in another embodiment, phenyl.

The "hetero ring" means a ring group containing i) a monocyclic 3- to 8-membered, and in another embodiment, a 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by ring-fusion of said monocyclic hetero ring with one or two rings which is selected from a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring" include the following embodiments:

(1) Monocyclic Saturated Hetero Ring Group (a) those containing 1 to 4 nitrogen atoms, for example, azepanyl, diazepanyl, aziridinyl, azetidinyl, pyrrolidinyl, imidazolidinyl, piperidyl, pirazolidinyl, piperazinyl, azocanyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like; and (e) those containing 1 to 2 oxygen atoms, for example, oxiranyl, oxetanyl, dioxolanyl, tetrahydrofuranyl, tetrahydropyranyl, 1,4-dioxanyl, and the like;

(2) Monocyclic Unsaturated Hetero Ring Group (a) those containing 1 to 4 nitrogen atoms, for example, pyrrolyl, imidazolyl, pyrazolyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, hydrodithionyl, and the like;

(d) those containing 1 to 2 sulfur atoms and 1 to 2 oxygen atoms, for example, dihydroxythiopyranyl and the like; and (e) those containing 1 to 2 oxygen atoms, for example, furyl, pyranyl, oxepinyl, dioxolyl, and the like;

(3) Fused Polycyclic Saturated Hetero Ring Group (a) those containing 1 to 5 nitrogen atoms, for example, quinuclidinyl, 7-azabicyclo[2.2.1]heptyl, 3-azabicyclo[3.2.2]nonanyl, and the like;

(b) those containing 1 to 4 nitrogen atoms and 1 to 3 sulfur atoms, and/or 1 to 3 oxygen atoms, for example, trithiadiazaindenyl, dioxoloimidazolidinyl, and the like; and (c) those containing 1 to 3 sulfur atoms and/or 1 to 3 oxygen atoms, for example, 2,6-dioxabicyclo[3.2.2]octo-7-yl and the like;

(4) Fused Polycyclic Unsaturated Hetero Ring Group (a) those containing 1 to 5 nitrogen atoms, for example, indolyl, isoindolyl, indolinyl, indolidinyl, benzoimidazolyl, dihydrobenzoimidazolyl, tetrahydrobenzoimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, and the like;

(b) those containing 1 to 4 nitrogen atoms, and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxazinyl, benzoxadiazolyl, benzoisothiazolyl, benzoisoxazolyl, and the like;

(c) those containing 1 to 3 sulfur atoms, for example, benzothienyl, benzodithiopyranyl, dibenzo[b,d]thienyl, and the like;

(d) those containing 1 to 3 sulfur atoms and 1 to 3 oxygen atoms, for example, benzoxathiopyranyl, phenoxazinyl, and the like;

(e) those containing 1 to 3 oxygen atoms, for example, benzodioxolyl, benzofuranyl, dihydrobenzofuranyl, isobenzofuranyl, chromanyl, chromenyl, dibenzo[b,d]furanyl, methylenedioxyphenyl, ethylenedioxyphenyl, and the like; etc.

The "cyclic amino" means a monovalent group of a 3- to 8-membered cyclic amine ring, which may contain a partially unsaturated bond and may contain nitrogen, oxygen, or sulfur. Specific examples thereof include those in which a nitrogen atom in (1) "Monocyclic saturated hetero ring group" and (2) "Monocyclic unsaturated hetero ring group" as described for the "hetero ring" forms a monovalent group.

The ring atom, sulfur or nitrogen, may be oxidized to form an oxide or a dioxide.

Examples of the saturated cyclic amino include aziridin-1-yl, azetidin-1-yl, pyrrolidin-1-yl, pyrazolidin-1-yl, piperidin-1-yl, piperazin-1-yl, morpholin-4-yl, thiomorpholin-4-yl, and azepan-1-yl, and examples of the unsaturated cyclic amino include pyrrol-1-yl, imidazol-1-yl, pyrazol-1-yl, pyrrolin-1-yl, imidazolin-1-yl, 1,2-dihydropyrimidin-1-yl, 1,4-dihydropyridin-1-yl, 1,4,5,6-tetrahydropyridazin-1-yl, and azepin-1-yl.

Examples of the 5- to 7-membered saturated cyclic amino formed when $R^2$ and $R^3$ are combined with a nitrogen atom to which they bind include pyrrolidin-1-yl, piperidin-1-yl, piperazin-1-yl, morpholin-4-yl, and azepan-1-yl, in another embodiment, pyrrolidin-1-yl, piperidin-1-yl, and piperazin-1-yl, in a further embodiment, piperazin-1-yl and morpholin-4-yl, and in a further embodiment, piperazin-1-yl.

Examples of the 5- to 7-membered saturated cyclic amino formed when $R^{41}$ and $R^{42}$ are combined with a nitrogen atom to which they bind include pyrrolidin-1-yl and morpholin-4-yl.

The "heteroaryl" refers to an aromatic ring group within the formally described "hetero ring" (2), or hetero ring group within the formally described "hetero ring" (4) which comprises at least one aromatic group. Examples thereof include a monocyclic heteroaryl such as pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, and the like, a bicyclic heteroaryl such as indolyl, isoindolyl, benzoimidazolyl, indazolyl, quinolyl, isoquinolyl, quinazolinyl, quinoxalinyl, phthalazinyl, benzothiazolyl, benzoisothiazolyl, benzothiadiazolyl, benzoxazolyl, benzoisoxazolyl, benzofuranyl, benzothienyl, and the like, and a tricyclic heteroaryl such as carbazolyl, dibenzo[b,d]furanyl, dibenzo[b,d]thienyl, and the like.

Examples of the "heteroaryl" in $R^2$ and $R^3$ include pyridyl, pyrrolyl, pyrazinyl, pyrimidinyl, pyridazinyl, imidazolyl, triazolyl, triazinyl, tetrazolyl, and pyrazolyl, and in another embodiment, pyridyl.

The "nitrogen-containing saturated hetero ring" refers to a monocyclic saturated hetero ring or a fused polycyclic saturated hetero ring, which includes at least one nitrogen atom and may further include a heteroatom selected from oxygen and sulfur, as described in (1) (a), (1) (b), (3) (a), and (3) (b) of the "hetero ring" above. The ring atom, sulfur or nitrogen, may be oxidized to form an oxide or a dioxide.

Examples of the "nitrogen-containing saturated hetero ring" in $R^2$ and $R^3$ include azepanyl, diazepanyl, aziridinyl, azetidinyl, pyrrolidinyl, imidazolidinyl, piperidyl, pyrazolidinyl, piperazinyl, and azocanyl, and in another embodiment, piperidyl.

Examples of the "protected carboxy" group can include the following groups:

(1) Esterified carboxy group. Specific examples thereof include —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, and the like.

(2) Amidated carboxy group. Specific examples thereof include —CO—NH$_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-CO$_2$H, and the like; and in another embodiment, —CO—O-lower alkyl such as —CO—O-methyl, —CO—O-ethyl, —CO—O-tert-butyl, and the like.

In the present specification, the expression "which may be substituted" represents "which is not substituted" or "which is substituted with 1 to 5 substituents". Further, if it has a plurality of substituents, the substituents may be the same as or different from each other.

Examples of the substituent in the "lower alkyl, cycloalkyl, aryl, heteroaryl, and nitrogen-containing saturated hetero ring" in $R^2$ and $R^3$ include halogen; lower alkyl; pyridyl; carboxy; protected carboxy; amino which may be substituted with one lower alkyl, or the same or different two or more lower alkyls; —O-lower alkyl; —[CH(—OH)]$_m$—H; and —OH, in another embodiment, carboxy; and protected carboxy, and in a further embodiment, carboxy.

Examples of the substituent in the "5- to 7-membered saturated cyclic amino" "pyrrolidin-1-yl, piperidin-1-yl, piperazin-1-yl, morpholin-4-yl, or azepan-1-yl", or "piperazin-1-yl" each of which is formed when $R^2$ and $R^3$ are combined with a nitrogen atom to which they bind, include halogen; —OH; oxo(═O); —O-lower alkyl; cyano; nitro; cycloalkyl; aryl; hetero ring; lower alkylene-aryl; lower alkylene-hetero ring; lower alkyl which may be substituted with halogen, —OH, —O-lower alkyl, or cyano; carboxy; protected carboxy; and —CO-lower alkyl; in another embodiment, lower alkyl; carboxy; protected carboxy; —CO-lower alkyl; and aryl, in a further embodiment, lower alkyl; carboxy; and —CO-lower alkyl, and in a further embodiment, —CO-lower alkyl.

Examples of the substituent in the "lower alkyl which may be substituted" in $R^{41}$ or $R^{42}$ include —OH.

Embodiments of the compound of the formula (I) or a salt thereof are shown below.

(1-1) The compound or a salt thereof, wherein $R^1$ is —O-lower alkyl, and in another embodiment, the compound or a salt thereof, wherein $R^1$ is —O-methyl.

(1-2) The compound or a salt thereof, wherein $R^1$ is -lower alkylene-pyridyl, and in another embodiment, the compound or a salt thereof, wherein $R^1$ is pyridin-4-ylmethyl.

(1-3) The compound or a salt thereof, wherein $R^1$ is -lower alkylene-(phenyl substituted with carboxy or protected carboxy), in another embodiment, the compound or a salt thereof, wherein $R^1$ is -lower alkylene-(phenyl substituted with carboxy), in a further embodiment, the compound or a salt thereof, wherein $R^1$ is 2-(4-carboxyphenyl)ethyl or 3-(4-carboxyphenyl)propyl, in a further embodiment, the compound or a salt thereof, wherein $R^1$ is 2-(4-carboxyphenyl)ethyl, and in a further embodiment, the compound or a salt thereof, wherein $R^1$ is 3-(4-carboxyphenyl)propyl.

(2-1) The compound or a salt thereof, wherein $R^2$ is lower alkyl which may be substituted with at least one substituent selected from the group consisting of carboxy, protected carboxy, —OH, pyridyl, carboxyphenyl, and methoxycarbonylphenyl, in another embodiment, the compound or a salt thereof, wherein $R^2$ is $C_{2-4}$ alkyl substituted with carboxy, and in a further embodiment, the compound or a salt thereof, wherein $R^2$ is 2-carboxyethyl, 3-carboxypropyl, 4-carboxybutyl, or 2-carboxypropan-2-yl.

(2-2) The compound or a salt thereof, wherein $R^2$ is a cycloalkyl which may be substituted with at least one substituent selected from the group consisting of carboxy and protected carboxy, in another embodiment, the compound or a salt thereof, wherein $R^2$ is $C_{3-6}$ cycloalkyl substituted with carboxy, and in a further embodiment, the compound or a salt thereof, wherein $R^2$ is 1-carboxycyclopropyl or 4-carboxycyclohexyl.

(2-3) The compound or a salt thereof, wherein $R^2$ is phenyl which may be substituted with at least one substituent selected from the group consisting of carboxy, protected carboxy, and —O-lower alkyl, in another embodiment, the compound or a salt thereof, wherein $R^2$ is phenyl substituted with carboxy, and in a further embodiment, the compound or a salt thereof, wherein $R^2$ is 4-carboxyphenyl.

(2-4) The compound or a salt thereof, wherein $R^2$ is pyridyl which may be substituted with at least one substituent selected from the group consisting of carboxy and protected carboxy.

(2-5) The compound or a salt thereof, wherein $R^2$ is 2-carboxyethyl, 3-carboxypropyl, 4-carboxybutyl, 2-carboxypropan-2-yl, 1-carboxycyclopropyl, 4-carboxycyclohexyl, or 4-carboxyphenyl.

(3-1) The compound or a salt thereof, wherein $R^3$ is a lower alkyl which may be substituted with at least one substituent selected from the group consisting of —O-lower alkyl, and amino which may be substituted with one alkyl, or the same or different two lower alkyls, in another embodiment, the compound or a salt thereof, wherein $R^3$ is methyl, ethyl, isopropyl, n-propyl, 2-methoxyethyl, or 2-(diisopropylamino)ethyl, and in a further embodiment, the compound or a salt thereof, wherein $R^3$ is methyl, ethyl, isopropyl, or n-propyl.

(3-2) The compound or a salt thereof, wherein $R^3$ is cycloalkyl, and in another embodiment, the compound or a salt thereof, wherein $R^3$ is cyclopropyl.

(3-3) The compound or a salt thereof, wherein $R^3$ is piperidin-4-yl substituted with lower alkyl, and in another embodiment, the compound or a salt thereof, wherein $R^3$ is 1-(isopropyl)piperidin-4-yl.

(3-4) The compound or a salt thereof, wherein $R^3$ is methyl, ethyl, isopropyl, n-propyl, or cyclopropyl.

(4-1) The compound or a salt thereof, wherein n is 0.

(4-2) The compound or a salt thereof, wherein n is 1 and $R^4$ is halogen, methyl, —OH, —O-methyl, —NO$_2$, 2-hydroxyethylamino, pyrrolidin-1-yl, or morpholin-4-yl.

(5-1) The compound or a salt thereof, wherein $R^2$ and $R^3$ are combined with a nitrogen atom to which they bind to form pyrrolidin-1-yl, piperidin-1-yl, piperazin-1-yl, or morpholin-4-yl, which may be substituted with at least one substituent selected from the group consisting of lower alkyl, carboxy, protected carboxy, —CO-lower alkyl, and phenyl.

(5-2) The compound or a salt thereof, wherein $R^2$ and $R^3$ are combined with a nitrogen atom to which they bind to form 4-acetylpiperazin-1-yl.

(5-3) The compound or a salt thereof, wherein $R^2$ and $R^3$ are combined with a nitrogen atom to which they bind to form morpholin-4-yl.

(5-4) The compound or a salt thereof, wherein $R^2$ and $R^3$ are combined with a nitrogen atom to which they bind to form piperidin-1-yl which may be substituted with at least one substituent selected from the group consisting of carboxy and protected carboxy.

(6) The compound or a salt thereof, which is a combination of two or more groups recited in (1-1) to (5-4) as described above.

The compound or a salt thereof as described above in (6), which is a combination of two or more groups recited in (1-1) to (5-4) as described above, is included in the present invention, but the specific examples thereof and the following embodiments are also included.

(7) The compound or a salt thereof, wherein n is 0.

(8) The compound or a salt thereof as described in (7), wherein $R^1$ is -lower alkylene-(phenyl substituted with carboxy or protected carboxy).

(9) The compound or a salt thereof as described in (8), wherein $R^1$ is lower alkylene-(phenyl substituted with carboxy).

(10) The compound or a salt thereof as described in (9), wherein $R^2$ is lower alkyl, cycloalkyl, or phenyl, each of which is substituted with carboxy.

(11) The compound or a salt thereof as described in (10), wherein $R^3$ is lower alkyl or cycloalkyl.

(12) The compound or a salt thereof as described in (9), wherein $R^2$ and $R^3$ are combined with a nitrogen atom to which they bind to form pyrrolidin-1-yl, piperidin-1-yl, piperazin-1-yl, morpholin-4-yl, or azepan-1-yl (these may be substituted).

(13) The compound or a salt thereof as described in (12), wherein $R^2$ and $R^3$ are combined with a nitrogen atom to which they bind to form piperazin-1-yl which may be substituted.

Examples of the specific compounds encompassed by the present invention include:

4-{2-[4-({[2-({3-[(4-carboxycyclohexyl)(ethyl)sulfamoyl]benzoyl}amino)-4,5,6,7-tetrahydro-1-benzothiophen-3-yl]carbonyl}amino)phenyl]ethyl}benzoic acid, 4-{2-[4-({[2-({3-[(4-carboxycyclohexyl)(cyclopropyl)sulfamoyl]benzoyl}amino)-4,5,6,7-tetrahydro-1-benzothiophen-3-yl]carbonyl}amino)phenyl]ethyl}benzoic acid, 4-{2-[4-({[2-({3-[(3-carboxypropyl)(cyclopropyl)sulfamoyl]benzoyl}amino)-4,5,6,7-tetrahydro-1-benzothiophen-3-yl]carbonyl}amino)phenyl]ethyl}benzoic acid, 4-{2-[4-({[2-({3-[(1-carboxycyclopropyl)(ethyl)sulfamoyl]benzoyl}amino)-4,5,6,7-tetrahydro-1-benzothiophen-3-yl]carbonyl}amino)phenyl]ethyl}benzoic acid, 4-{2-[4-({[2-({3-[(1-carboxycyclopropyl)(isopropyl)sulfamoyl]benzoyl}amino)-4,5,6,7-tetrahydro-1-benzothiophen-3-yl]carbonyl}amino)phenyl]ethyl}benzoic acid, 4-{[(3-{[3-({4-[2-(4-carboxyphenyl)ethyl]phenyl}carbamoyl)-4,5,6,7-tetrahydro-1-benzothiophen-2-yl]carbamoyl}phenyl)sulfonyl](ethyl)amino}benzoic acid, 4-{3-[4-({[2-({3-[(4-carboxycyclohexyl)(ethyl)sulfamoyl]benzoyl}amino)-4,5,6,7-tetrahydro-1-benzothiophen-3-yl]carbonyl}amino)phenyl]propyl}benzoic acid, 4-{2-[4-({[2-({3-[(4-acetylpiperazin-1-yl)sulfonyl]benzoyl}amino)-4,5,6,7-tetrahydro-1-benzothiophen-3-yl]carbonyl}amino)phenyl]ethyl}benzoic acid, 4-{2-[4-({[2-({3-[(4-carboxybutyl)(cyclopropyl)sulfamoyl]benzoyl}amino)-4,5,6,7-tetrahydro-1-benzothiophen-3-yl]carbonyl}amino)phenyl]ethyl}benzoic acid, 4-{3-[4-({[2-({3-[(4-carboxycyclohexyl)(propyl)sulfamoyl]benzoyl}amino)-4,5,6,7-tetrahydro-1-benzothiophen-3-yl]carbonyl}amino)phenyl]propyl}benzoic acid, or salts thereof The compound of the formula (I) may exist in the form of tautomers or geometrical isomers depending on the kind of substituents. In the present specification, the compound of the formula (I) shall be described in only one form of isomer, yet the present invention includes the other isomers, isolated forms of the isomers, or a mixture thereof.

In addition, the compound of the formula (I) may have asymmetric carbon atoms or axial asymmetry in some cases, and correspondingly, it may exist in the form of optical isomers. The present invention includes both an isolated form of the optical isomers of the compound of the formula (I) or a mixture thereof Moreover, the present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the functional group) at the stage from starting material to an intermediate may be effective depending on the type of the functional group in the production technology in some cases. The protective group for such a functional group may include, for example, the protective groups described in "Greene's Protective Groups in Organic Synthesis (4$^{th}$ Ed., 2006)" written by P. G. M. Wuts and T. W. Greene, and one of these may be selected and used as necessary depending on the reaction conditions. In this kind of method, a desired compound can be obtained by introducing the protective group and carrying out the reaction before eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the compound of the formula (I) are not limited to the examples as shown below.

(Production Process 1)

[Chem. 23]

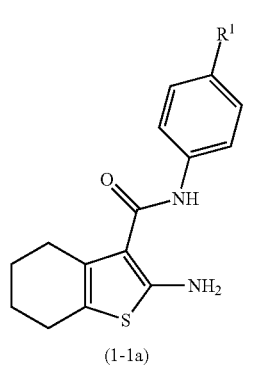

(1-1a)

No. 1

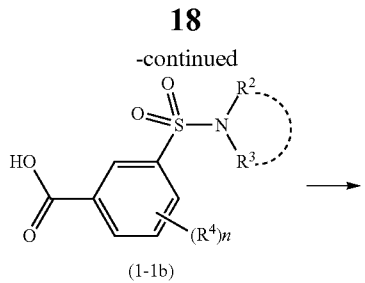

(1-1b)

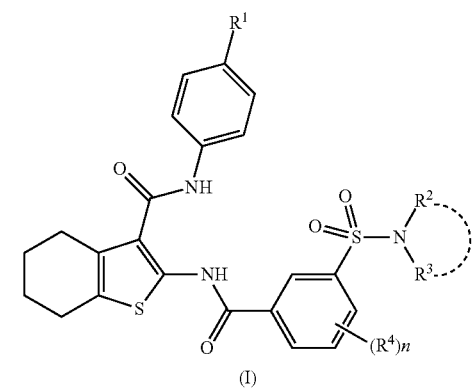

(I)

[Chem. 24]

No. 2

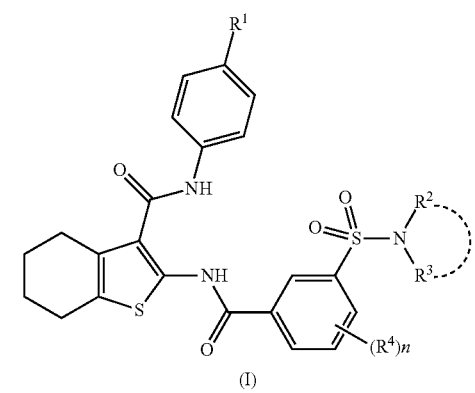

(1-2a)

(1-2b)

(I)

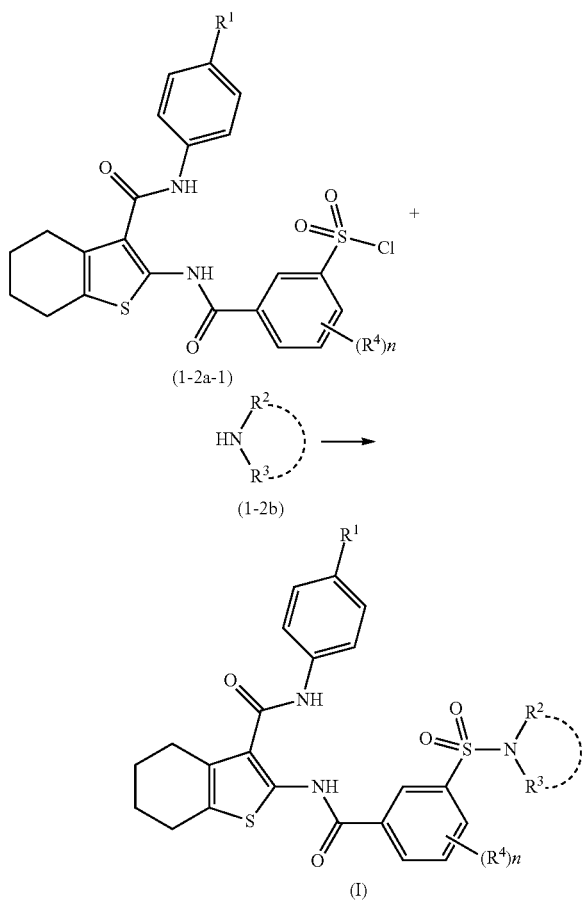

The compound of the formula (I) can be obtained by an amidation reaction of a compound (1-1a) with a compound (1-1b) or a sulfonamidation reaction of a compound (1-2a) with a compound (1-2b).

In this reaction, the compound (1-1a) and the compound (1-1b) or the compound (1-2a) and the compound (1-2b) in an equivalent amount or in an excess amount are used, and a mixture thereof is stirred under any temperature condition from cooling to heating, preferably at −20° C. to 120° C., usually for 0.1 hours to 5 days, in a solvent which is inert to the reaction, in the presence of a condensing agent. Examples of the solvent as used herein are not particularly limited, but include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran (THF), dioxane, dimethoxyethane, and the like, N,N-dimethylformamide (DMF), dimethylsulfoxide (DMSO), ethyl acetate, acetonitrile, N,N-dimethylacetamide (DMA), N-methylpyrrolidone (NMP), or water, and a mixture thereof. Examples of the condensing agent include 1-(3-dimethylamino propyl)-3-ethylcarbodiimide (EDCI), O-(7-azabenzotriazol-1-yl)-N,N,N',N'-tetramethyluronium hexafluorophosphate (HATU), O-(benzotriazol-1-yl)-N,N,N',N'-tetramethyluronium tetrafluoroborate (TBTU), bromo(tripyrrolidin-1-yl)phosphonium hexafluorophosphate, 1,1'-carbonyldiimidazole, diphenylphosphoric azide, phosphoryl chloride, N,N'-dicyclohexylcarbodiimide (DCC), 1,1'-carbonylbisimidazole (CDI), N,N'-disuccinimidyl carbonate, a BOP reagent (Aldrich, U.S.A.), 2-(1H-benzotriazol-1-yl)-1,1,3,3-tetramethyluronium hexafluorophosphate (HBTU), phosphorus oxychloride, phosphoric trichloride, triphenylphosphine/N-bromosuccinimide, and the like, but are not limited thereto. Further, a condensing agent-carrying polystyrene resin, for example, a PS-Carbodiimide (Biotage AB, Sweden), may also be used. In some cases, it is preferable to use an additive (for example, 1-hydroxybenzotriazole) for the reaction. It is in some cases advantageous in advancing the reaction smoothly to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like. Further, use of a microwave reactor (Biotage AB) makes it possible to advance the reaction smoothly in some cases. Also, depending on the case, it is possible to use an isocyanate-carrying polystyrene resin, for example, PS-Isocyanate (Biotage AB, Sweden) and the like, in order to remove an excessive amount of amine after completion of the reaction, or to use a quaternary ammonium salt-carrying polystyrene resin, for example, MP-Carbonate (Biotage AB, Sweden) and the like, in order to remove excessive amounts of carboxylic acid and the above-mentioned additives after completion of the reaction.

Furthermore, it is also possible to use a method in which a carboxylic acid of the compound (1-1b) or a sulfonic acid of the compound (1-2a) is reacted with an amine after conversion to its reactive derivative. Examples of the reactive derivative include acid halides that can be obtained by the reaction of a carboxylic acid or sulfonic acid with a halogenating agent such as oxalyl chloride, phosphorus oxychloride, thionyl chloride, and the like, mixed acid anhydrides that can be obtained by the reaction with isobutyl chloroformate or the like, active esters that can be obtained by condensation with 1-hydroxybenzotriazole or the like, etc. For example, examples of the reactive derivative of the compound (1-2a) include a compound (1-2a-1), and by a sulfonamidation reaction of the compound (1-2a-1) with the compound (1-2b), the compound (I) of the present invention can be obtained.

Furthermore, the reactive derivative (1-2a-1) can be derived even though it is not via sulfonic acid (1-2a), as shown below (Starting Material Synthesis 2).

For this process, reference may be made to, for example, the conditions for acylation or sulfonylation described in "Greene's Protective Groups in Organic Synthesis" above, or the method described in S. R. Sandler and W. Karo, "Organic Functional Group Preparations", 2$^{nd}$ edition, Vol. 1, Academic Press Inc., 1991 and "Courses in Experimental Chemistry (5$^{th}$ edition)", edited by The Chemical Society of Japan, Vol. 14 (2005) (Maruzen Company, Limited).

(Production Process 2)

[Chem. 26]

No. 1

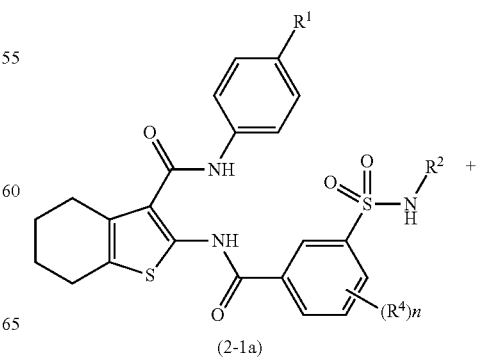

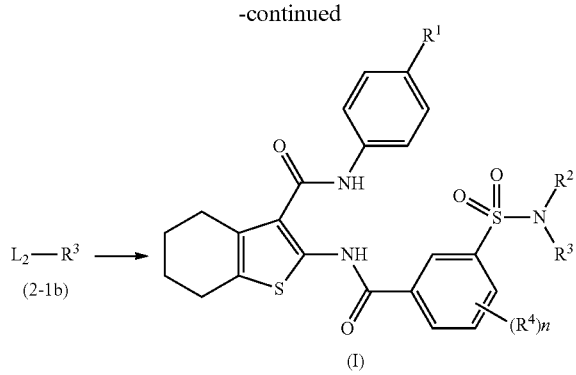

[Chem. 27]

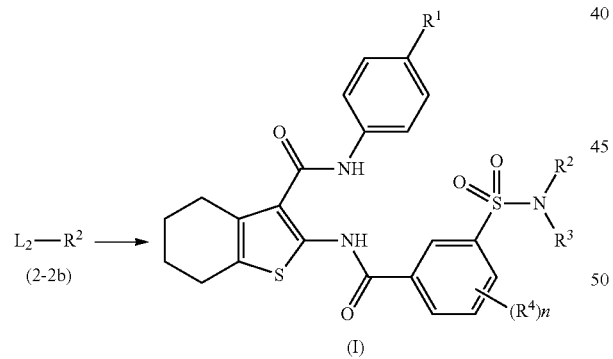

(wherein L₂ represents a leaving group. The same shall apply hereinafter.)

In "No. 1" above, the compound of the formula (I), wherein $R^3$ is lower alkyl, cycloalkyl, a nitrogen-containing saturated hetero ring, -lower alkylene-aryl, or -lower alkylene-heteroaryl (in which lower alkyl, cycloalkyl, aryl, heteroaryl, and the nitrogen-containing saturated hetero ring may be substituted) can be obtained by an alkylation reaction of an amine with the compound (2-1a) and the compound (2-1b).

In "No. 2" above, the compound of the formula (I), wherein $R^2$ is lower alkyl, cycloalkyl, a nitrogen-containing saturated hetero ring, -lower alkylene-aryl, or -lower alkylene-heteroaryl (in which lower alkyl, cycloalkyl, aryl, heteroaryl, and the nitrogen-containing saturated hetero ring may be substituted) can be obtained by an alkylation reaction of an amine with the compound (2-2a) and the compound (2-2b).

Here, examples of the leaving group include halogen, methanesulfonyloxy, p-toluenesulfonyloxy groups, and the like.

In this reaction, the compound (2-1a) and the compound (2-1b), or the compound (2-2a) and the compound (2-2b) in an equivalent amount or in an excess amount are used, and a mixture thereof is stirred under any temperature condition from cooling to heating under reflux, preferably at 0° C. to 80° C., usually for 0.1 hours to 5 days, in a solvent which is inert to the reaction or without a solvent. Examples of the solvent as used herein are not particularly limited, but include aromatic hydrocarbons such as benzene, toluene, xylene, pyridine, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, or a mixture thereof. It is in some cases advantageous in advancing the reaction smoothly to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like.

For this process, reference may be made to, for example, the aforementioned "Organic Functional Group Preparations" and "Courses in Experimental Chemistry ($5^{th}$ edition)", Vol. 14.

(Production Process 3)

[Chem. 28]

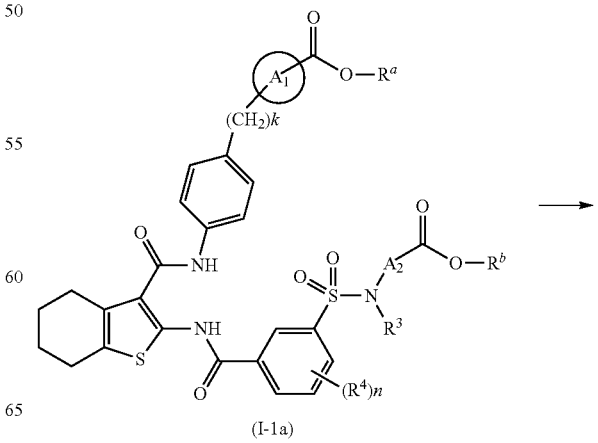

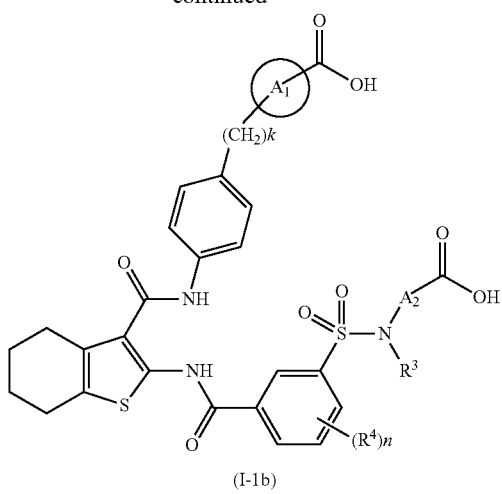

(I-1b)

[Chem. 29]

No. 2

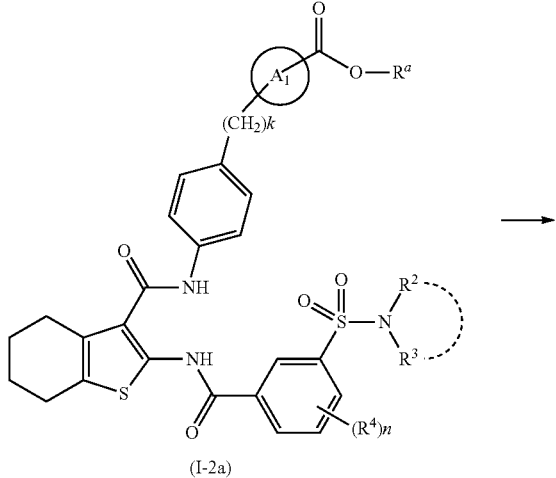

(I-2a)

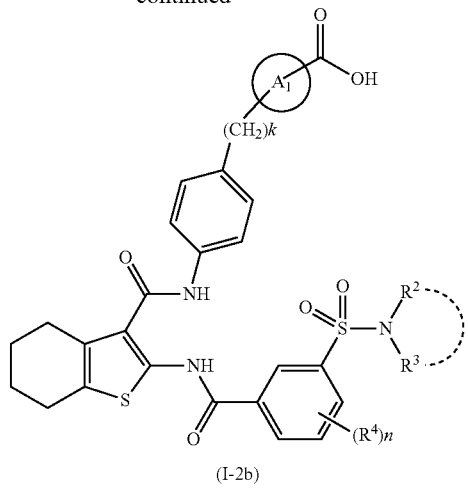

(I-2b)

(wherein $A_1$ represents phenylene or pyridinediyl, $A_2$ represents lower alkylene, cycloalkanediyl, phenylene, or pyridinediyl, k represents 1 to 6, and $R^a$ and $R^b$ represent lower alkyl, which are the same as or different from each other).

Among the compound of the formula (I), the compound represented by the general formula (I-1b) or the general formula (I-2b) can be prepared by hydrolysis of the compound of the general formula (I-1a) or the general formula (I-2a). Here, the hydrolysis reaction can be carried out in accordance with the aforementioned "Protective Groups in Organic Synthesis".

Moreover, the compound (I) of the present invention having various functional groups, for example, a carboxyl group, an amide group, a hydroxyl group, an alkylamino group, and the like, can be prepared from the compound (I) of the present invention, by any combination of the steps that can usually be employed by a person skilled in the art, such as alkylation, acylation, a substitution reaction, oxidation, reduction, hydrolysis, deprotection, halogenation, and the like (see the aforementioned "Courses in Experimental Chemistry ($5^{th}$ edition)", "Greene's Protective Groups in Organic Synthesis", or the like. In addition, the processes that can usually be employed by a person skilled in the art may be used in the application for the preparation of intermediates.

(Starting Material Synthesis 1)

[Chem. 30]

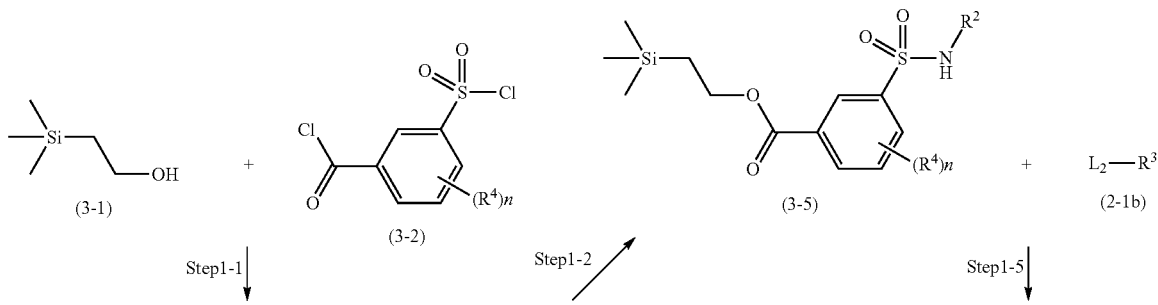

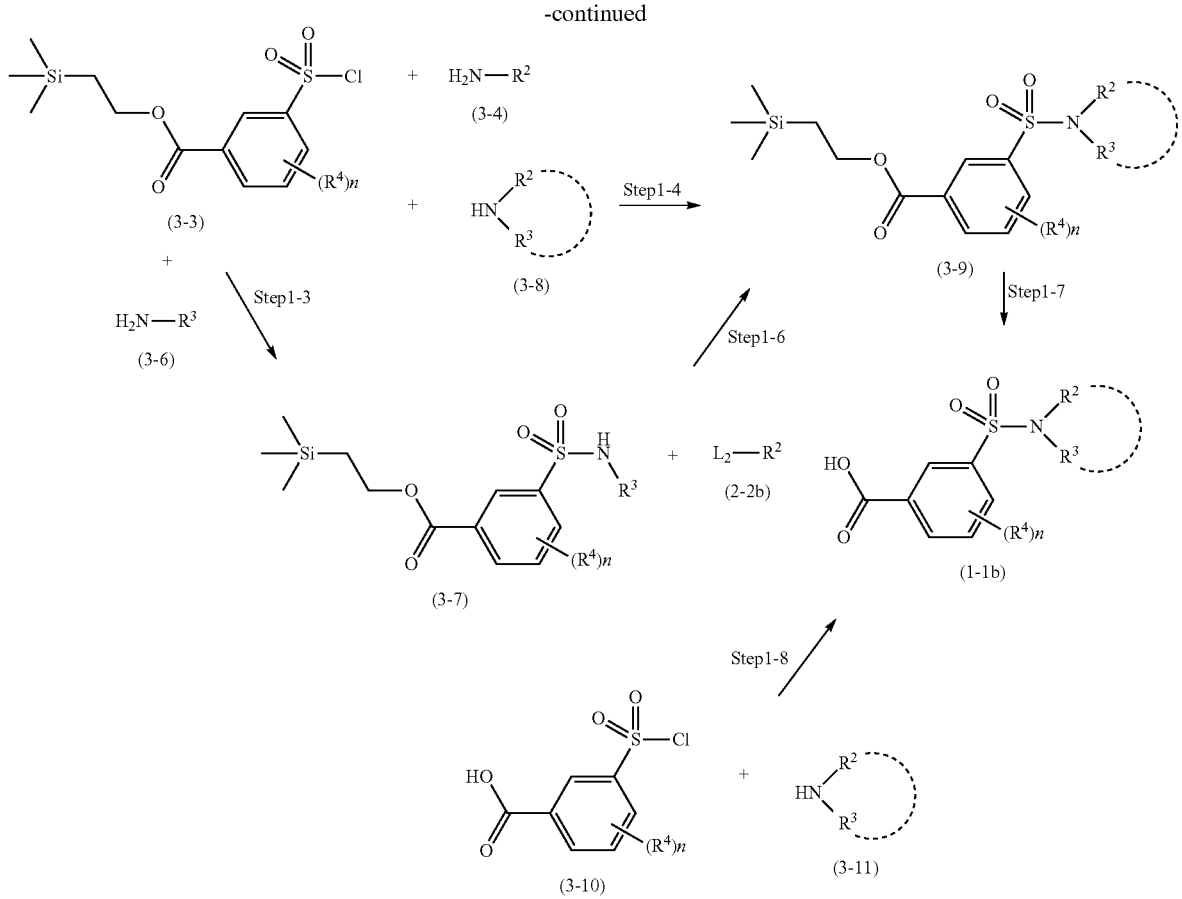

The step represented by Step 1-1 is a step in which a compound (3-3) is obtained by an esterification using a compound (3-1) and a compound (3-2). The esterification reaction can be carried out in accordance with the aforementioned "Protective Groups in Organic Synthesis".

Each of the steps represented by Step 1-2, Step 1-3, and Step 1-4 is a step in which a compound (3-5), a compound (3-7), and a compound (3-9) are obtained by a sulfonamidation reaction using the compound (3-3) and a compound (3-4), the compound (3-3) and a compound (3-6), and the compound (3-3) and a compound (3-8), respectively. The sulfonamidation reaction can be carried out in accordance with 2 of the Production Process 1.

Each of the steps represented by Step 1-5 and Step 1-6 is a step in which a compound (3-9) is obtained by an alkylation reaction of an amine using the compound (3-5) and the compound (2-1b), or the compound (3-7) and the compound (2-2b). The alkylation reaction of an amine can be carried out in accordance with Production Process 2.

The step represented by Step 1-7 is a step in which a compound (1-1b) is obtained by deprotection of the compound (3-9). For the deprotection in the present step, the condition for deprotection usually used by a person skilled in the art can be applied. For example, the deprotection can be carried out in accordance with the aforementioned "Protective Groups in Organic Synthesis", p. 573-575, or the like. In addition, the deprotection can also be carried out by hydrolysis in accordance with Production Process 3.

The step represented by Step 1-8 is a step in which a compound (1-1b) is obtained by a sulfonamidation reaction using a compound (3-10) and a compound (3-11). The sulfonamidation reaction can be carried out in accordance with 2 of the Production Process 1.

(Starting Material Synthesis 2)

[Chem. 31]

-continued

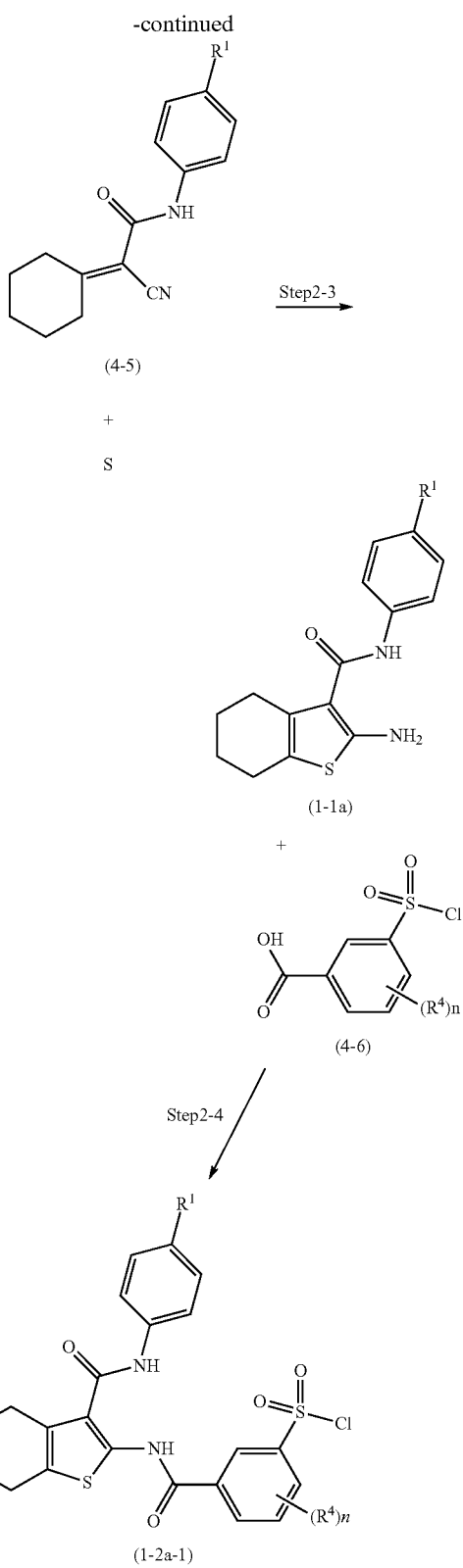

The step represented by Step 2-2 is a step in which a compound (4-5) which is an intermediate for the Gewald reaction is obtained by a reaction of the compound (4-3) with a compound (4-4) by a Gewald reaction. Further, the step represented by Step 2-3 is a step in which a compound (1-1a) which is a thiophene derivative is obtained by a reaction by a reaction of the compound (4-5) with sulfur. This reaction is carried out by stirring a mixture of the compound (4-3) and the compound (4-4), or a mixture of the compound (4-5) and sulfur under any temperature condition from room temperature to heating, usually for 0.1 hours to 5 days, in a solvent which is inert to the reaction, in the presence of a base. Further, it is also possible to carry out Step 2-2 and Step 2-3, simultaneously. That is, the reaction can also be carried out by stirring a mixture of the compound (4-3), the compound (4-4), and sulfur under any temperature condition from room temperature to heating, usually for 0.1 hours to 5 days, in a solvent which is inert to the reaction, in the presence of a base. Further, it is also possible to carry out Step 2-2 and Step 2-3 simultaneously. Examples of the solvent as used herein are not particularly limited, but include aromatic hydrocarbons such as benzene, toluene, xylene, pyridine, and the like, ethers such as diethyl ether, tetrahydrofuran, dioxane, dimethoxyethane, and the like, halogenated hydrocarbons such as dichloromethane, 1,2-dichloroethane or chloroform, and the like, alcohols such as methanol, ethanol, 2-propanol, butanol, and the like, N,N-dimethylformamide, dimethylsulfoxide, and a mixed solvent thereof. The base is not particularly limited, but examples thereof include organic bases such as morpholine and the like. For this process, reference may be made to, for example, the method described in McKibben, B. P., et al., Tetrahedron Lett., 40:5471, (1999).

The step represented by Step 2-4 is a step in which a compound (1-2a-1) is obtained by an amidation reaction using the compound (1-1a) and the compound (4-6). The amidation reaction can be carried out in accordance with 1 of the Production Process 1.

Further, the compound (2-1a) or the compound (2-2a) can be obtained by a sulfonamidation reaction using the compound (1-2a-1) and the compound (3-4), or the compound (1-2a-1) and the compound (3-6). The sulfonamidation reaction can be carried out in accordance with 2 of the Production Process 1.

(Starting Material Synthesis 3)

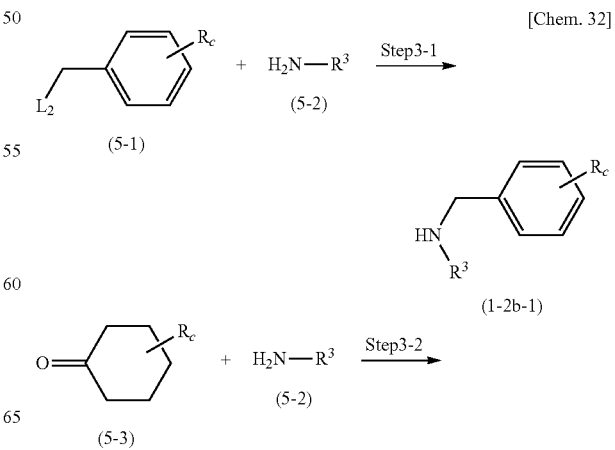

The step represented by Step 2-1 is a step in which a compound (4-3) is obtained by an amidation reaction using a compound (4-1) and a compound (4-2). The amidation reaction can be carried out in accordance with 1 of the Production Process 1.

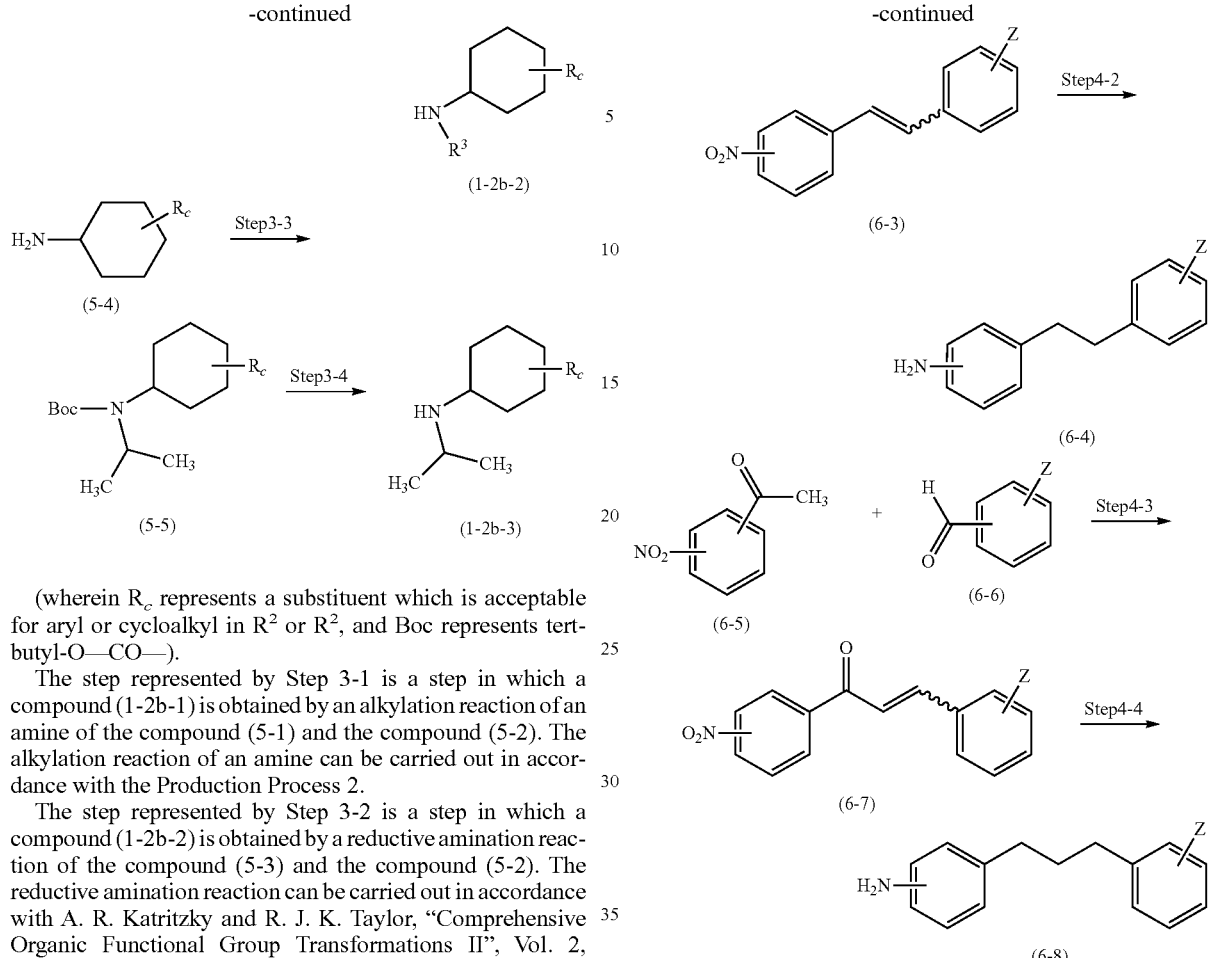

(wherein $R_c$ represents a substituent which is acceptable for aryl or cycloalkyl in $R^2$ or $R^2$, and Boc represents tert-butyl-O—CO—).

The step represented by Step 3-1 is a step in which a compound (1-2b-1) is obtained by an alkylation reaction of an amine of the compound (5-1) and the compound (5-2). The alkylation reaction of an amine can be carried out in accordance with the Production Process 2.

The step represented by Step 3-2 is a step in which a compound (1-2b-2) is obtained by a reductive amination reaction of the compound (5-3) and the compound (5-2). The reductive amination reaction can be carried out in accordance with A. R. Katritzky and R. J. K. Taylor, "Comprehensive Organic Functional Group Transformations II", Vol. 2, Elsevier Pergamon, 2005, or the aforementioned "Courses in Experimental Chemistry ($5^{th}$ edition)".

The step represented by Step 3-3 is a step in which a compound (5-5) is obtained by a reductive amination reaction of the compound (5-4) and then a subsequent Boc-addition reaction thereof. The Boc-addition reaction can be carried out in accordance with the aforementioned "Protective Groups in Organic Synthesis".

The step represented by Step 3-4 is a step in which a compound (1-2b-3) is obtained by eliminating Boc of the compound (5-5). The elimination of Boc can be carried out in accordance with the afore-mentioned "Protective Groups in Organic Synthesis".

(Starting Material Synthesis 4)

[Chem. 33]

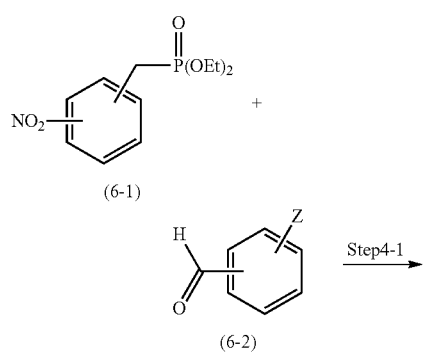

(wherein Z means a protected carboxyl group).

The step represented by Step 4-1 is a reaction in which a compound (6-3) is obtained by a reaction of a compound (6-1) and a compound (6-2) by a Horner-Wadsworth-Emmons reaction. In this reaction, a mixture of the compound (6-1) and the compound (6-2) are stirred under any temperature condition from room temperature to heating under reflux, preferably at a temperature from 0° C. to 80° C., usually for 0.1 hours to 5 days, in a solvent which is inert to the reaction, in the presence of a base. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile and a mixture thereof. Examples of the base include organic bases such as sodium methoxide, potassium-tert-butoxide, n-butyl lithium, lithium hexamethyldisilazide, and the like, and inorganic bases such as potassium carbonate, sodium carbonate, potassium hydroxide, sodium hydride, and the like. For this process, reference may be made to, for example, the method described in W. S. Wadsworth, Jr., W. D. Emmons, Journal of American Chemical Society, 1961, 83:1733.

The step represented by Step 4-2 is a reaction in which a compound (6-4) is obtained by a hydrogenation reaction of the compound (6-3). For the hydrogenation reaction, reference may be made to, for example, the method described in M. Hudlicky, "Reductions in Organic Chemistry, $2^{nd}$ ed. (ACS Monograph: 188)", ACS, 1996, and the aforementioned "Courses in Experimental Chemistry ($5^{th}$ edition)", Vol. 19 (2005).

The step represented by Step 4-3 is a reaction in which a compound (6-7) is obtained by a Claisen-Schmidt reaction of the compound (6-5) with the compound (6-6). For the Claisen-Schmidt reaction, reference may be made to, for example, the method described in J. March, "Advanced Organic Chemistry, $4^{th}$ ed. "Wiley Interscience, 1992.

The step represented by Step 4-4 is a reaction in which a compound (6-8) is obtained by a hydrogenation reaction of the compound (6-7). For the hydrogenation reaction, reference may be made to, for example, the method described in C. W. Jefford, Tetrahedron Letter, 1994, 35:4759.

The compound of the formula (I) can be isolated and purified as their free compounds, salts, hydrates, solvates, or polymorphic crystal substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

Test Example 1

$^{33}$P Phosphate Uptake Inhibiting Action of Rat NPT-IIb Expressing Cell

Preparation of Rat NPT-IIb Expressing Cell

Using rat small intestine cDNA library as a template, rat NPT-IIb ORF was cloned into p3×FLAG-CMV-10 by PCR according to a standard method. Then, the cloned rat NPT-IIb expressing plasmid was transfected into 293 cells, and G418 was used to obtain a rat NPT-IIb-stably expressing cell line.

Evaluation System on Inhibition of Phosphate Uptake into Rat NPT-IIb Expressing Cell The rat NPT-IIb expressing cells were seeded into a 96-well plate and incubated overnight. The medium was taken out and washed with buffer A (137 mM N-methyl-D-glucamine, 5.4 mM KCl, 2.8 mM $CaCl_2$, 1.2 mM $MgCl_2$, 10 mM HEPES (adjusted to pH 7.4 with HCl)), and then buffer B (137 mM NaCl, 5.4 mM KCl, 2.8 mM $CaCl_2$, 1.2 mM $MgCl_2$, 0.1 mM $KH_2PO_4$, 10 mM HEPES (adjusted to pH 7.4 with KOH)) was added thereto. Then, a compound having 10-fold higher concentration relative to the evaluation concentration was prepared by dilution with the buffer B and added thereto, followed by incubation in $CO_2$ incubator. Buffer B supplemented 50 µCi/mL $^{33}$P was added thereto, followed by further incubation in a $CO_2$ incubator. After the reaction, the buffer was taken out and the cells were washed with buffer C (137 mM NaCl, 10 mM Tris/HCl pH 7.2). Then, Microscint-20 was added thereto and $^{33}$P uptake was measured by using TopCount. The inhibitory rate was determined according to the following equation.

Inhibitory rate (%)=(1−($^{33}$P uptake of drug-treated well)/($^{33}$P uptake of DMSO-added well))×100

For several compounds of the formula (I), rat NPT-IIb inhibitory activity at a pharmacological evaluation concentration of 1 µM is shown in Table 1. Here, Ex represents Example No. as denoted below (this shall apply hereinafter).

TABLE 1

| Ex. | Rat NPT-IIb inhibitory rate (%) |
|---|---|
| 2 | 83 |
| 4 | 82 |
| 5 | 87 |
| 10 | 42 |
| 12 | 76 |
| 14 | 71 |
| 17 | 75 |
| 21 | 85 |
| 23 | 86 |
| 25 | 52 |
| 27 | 58 |
| 29 | 51 |
| 34 | 80 |
| 58 | 65 |
| 70 | 83 |
| 102 | 87 |
| 109 | 52 |

Test Example 2

Blood Radioactivity Increase Inhibiting Action in Orally $^{32}$P Phosphate Loaded Rats (Phosphate Absorption Inhibitory Action)

Male Wistar rats (6 to 7 weeks old) were fasted for 24 hours and used as experimental animals. The compound was dissolved or suspended with a solvent, and was used at a concentration of 0.6 mg/mL. The compound-administered animals were forcibly orally administered with the compound at a dose of 3 mg/kg. Control-group animals were administered a solvent containing no compound at a dose of 5 mL/kg. After 5 minutes from administration of the compound or from administration of the solvent, a $^{32}$P-containing phosphate solution (8.3 mM $NaH_2PO_4$) was orally administered thereto at a dose of 7.2 mL/kg. After 15 minutes and 30 minutes, the blood was taken from the orbital venous plexus and the serum was collected. Radioactivity in 0.1 mL of the serum was measured by a liquid scintillation counter. $AUC_{0-30min}$ calculated from the measured counts was considered as a phosphate absorption amount. The phosphate absorption inhibitory rate was determined from the $AUC_{0-30min}$ value according to the following equation.

Phosphate absorption inhibitory rate (%)=(1−Phosphate absorption count of compound-administered group/Phosphate absorption count of control group)×100

As a result, it was confirmed that several compounds of the formula (I) have an intestinal phosphate absorption inhibitory action. With the several compounds of the formula (I), the phosphate absorption inhibitory rates at a pharmacological evaluation dose of 3 mg/kg are shown in Table 2.

TABLE 2

| Ex. | Phosphate absorption inhibitory rate (%) |
|---|---|
| 2 | ≥60 |
| 4 | ≥60 |
| 12 | ≥60 |
| 14 | 47 |
| 23 | ≥60 |
| 34 | ≥60 |
| 58 | ≥60 |
| 102 | ≥60 |

As a result of the above test, with several compounds of the formula (I), an NPT-IIb inhibitory action and an intestinal phosphate absorption inhibitory action were confirmed. Therefore, the compound of the formula (I) can be used to treat hyperphosphatemia or the like.

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or more active ingredient(s) are mixed with at least one inactive excipient, such as lactose, mannitol, glucose, hydroxypropyl cellulose, microcrystalline cellulose, starch, polyvinyl pyrrolidone, and/or magnesium aluminometasilicate. In a conventional method, the composition may contain inactive additives, such as a lubricant such as magnesium stearate, a disintegrating agent such as carboxymethyl starch sodium and the like, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, cataplasm, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, hydrofluoroalkane, carbon dioxide, and the like, or other forms.

In oral administration, the daily dose is generally from about 0.001 to 100 mg/kg, preferably from 0.1 to 30 mg/kg, and more preferably 0.1 to 10 mg/kg, per body weight, administered in one portion or in two or more divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various therapeutic or prophylactic agents for the diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

Furthermore, the following abbreviations may be used in some cases in the Examples, Preparation Examples, and Tables below. Pr: Preparation Example No., Ex: Example No., Structure: Structural formula, Syn: Preparation method (the numeral shows that the Example compound was prepared in the similar manner as a compound having its number as the Example No.), Data: Physicochemical data, ESI+: m/z values in mass spectroscopy (Ionization ESI, representing (M+H)$^+$ unless otherwise specified), ESI−: m/z values in mass spectroscopy (Ionization ESI, representing (M−H)$^−$ unless otherwise specified), EI: m/z values in mass spectroscopy (Ionization EI, representing (M)$^+$ unless otherwise specified), FAB+: m/z values in mass spectroscopy (Ionization FAB, representing (M+H)$^+$ unless otherwise specified), FAB−: m/z values in mass spectroscopy (Ionization FAB, representing (M−H)$^−$ unless otherwise specified), APCI+: m/z values in mass spectroscopy (Ionization APCI, representing (M+H)$^+$ unless otherwise specified), APCI/ESI+: m/z values in mass spectroscopy (Ionization APCI and ESI simultaneously performed, representing (M+H)$^+$ unless otherwise specified), APCI/ESI−: m/z values in mass spectroscopy (Ionization APCI and ESI simultaneously performed, representing (M−H)$^−$ unless otherwise specified), CI+: m/z values in mass spectroscopy (Ionization CI, representing (M+H)$^+$ unless otherwise specified), NMR: δ (ppm) of peak in $^1$H NMR in DMSO-d$_6$, s: singlet (spectrum), d: doublet (spectrum), t: triplet (spectrum), q: quartet (spectrum), m: multiplet (spectrum), br: broad line (spectrum) (e.g.: br s), m.p.: Melting point HCl in the structural formula indicates that the Example compound is isolated as a hydrochloride.

Furthermore, for the sake of convenience, a concentration mol/l is expressed as M. For example, a 1 M aqueous sodium hydroxide solution means a 1 mol/l aqueous sodium hydroxide solution.

Preparation Example 1

(1) To a mixture of 50.3 g of diethyl (4-nitrobenzyl)phosphonate and 500 mL of methanol was added dropwise a solution of sodium methylate in methanol (ca. 5 mol/L, 73.7 mL) under ice-cooling, followed by stirring for 30 minutes under ice-cooling. To the reaction mixture was added dropwise a mixture of 30.6 g of methyl 4-formylbenzoate and 300 mL of methanol for 1 hour under ice-cooling, followed by stirring at room temperature for 15 hours after the addition dropwise. The precipitate was collected by filtration to obtain 48.8 g of methyl 4-[(E)-2-(4-nitrophenyl)vinyl]benzoate as a yellow solid. EI: 283

(2) To a mixture of 48.8 g of methyl 4-[(E)-2-(4-nitrophenyl)vinyl]benzoate, 600 mL of THF, and 200 mL of N,N-dimethylformamide (DMF) was added 10.0 g of 10% palladium on carbon (wetted with 55% H$_2$O), followed by stirring at room temperature for 8 hours under a hydrogen atmosphere (1 atm). The inside of the reaction container was replaced with argon, and then the insoluble materials were filtered off on a celite layer. The filtrate was concentrated under reduced pressure, and to the residue was added 1000 mL of water, followed by stirring at room temperature for 30 minutes. The precipitate was collected by filtration to obtain 43.3 g of methyl 4-[2-(4-aminophenyl)ethyl]benzoate as a white solid.

Preparation Example 2

(1) To a mixture of 16.5 g of 1-(4-nitrophenyl)ethanone, 16.4 g of methyl 4-formyl benzoate, and 100 mL of ethanol was added dropwise 4.0 mL of piperidine at room temperature, followed by stirring for 8 hours under heating and refluxing. The precipitate was collected by filtration to obtain 24.6 g of a crude product as a beige solid. The crude product was suspended in 100 mL, followed by stirring for 6 hours under heating and refluxing. The precipitate was collected by filtration to obtain 24.0 g of methyl 4-[3-(4-nitrophenyl)-3-oxoprop-1-en-1-yl]benzoate as a beige solid. ESI+: 312

(2) Under an argon atmosphere, to a mixture of 5.0 g of methyl 4-[3-(4-nitrophenyl)-3-oxoprop-1-en-1-yl]benzoate and 150 mL of methanol was added dropwise 5.0 mL of concentrated sulfuric acid under ice-cooling. Under an argon atmosphere, to the reaction mixture was added 500 mg of palladium on carbon under ice-cooling, followed by replacing with hydrogen (3 atm) at room temperature and then stirring at room temperature for 24 hours. The insoluble materials were filtered off on a celite layer and the filtrate was concentrated under reduced pressure. The residue was neutralized by the addition of a saturated aqueous sodium hydrogen carbonate solution under ice-cooling, followed by extraction with ethyl acetate. The organic layer was washed with water and saturated brine, and then dried over anhydrous sodium sulfate. The solvent was evaporated under reduced pressure and the obtained residue was purified by silica gel column chromatography (chloroform) to obtain 2.9 g of methyl 4-[3-(4-aminophenyl)propyl]benzoate as a pink oil.

Preparation Example 3

To a mixture of 43.9 g of methyl 4-[2-(4-aminophenyl)ethyl]benzoate, 22.3 g of cyanoacetic acid, and 150 mL of DMF was added 49.5 g of EDCI/hydrochloride under ice-cooling. After stirring at room temperature for 24 hours, to the reaction mixture was added 450 mL of water at room temperature. After vigorous stirring at room temperature for 30 minutes, the precipitate was collected by filtration to obtain 54.2 g of methyl 4-(2-{4-[(cyanoacetyl)amino]phenyl}ethyl)benzoate as a white solid.

Preparation Example 4

To a mixture of 16.0 g of methyl 4-[3-(4-aminophenyl)propyl]benzoate, 7.70 g of cyanoacetic acid, and 50 mL of DMF was added 17.1 g of EDCI/hydrochloride under ice-cooling. After stirring at room temperature for 18 hours, to the reaction mixture was added 200 mL of water at room temperature. After vigorous stirring at room temperature for 30 minutes, the precipitate was collected by filtration to obtain 19.3 g of methyl 4-(3-{4-[(cyanoacetyl)amino]phenyl}propyl)benzoate as a beige solid.

Preparation Example 5

(1) To a mixture of 54.0 g of methyl 4-(2-{4-[(cyanoacetyl)amino]phenyl}ethyl)benzoate, 50.0 mL of cyclohexanone, and 300 mL of toluene was added dropwise 15.0 mL of morpholine at room temperature. In a reaction apparatus to which a Dean-Stark type dehydration tube was attached, the reaction mixture was stirred at 120° C. for 3 hours. Subsequently, the reaction mixture was further heated to reflux and stirred for 1 hour. The reaction mixture was cooled to room temperature and then concentrated under reduced pressure. To the residue was further added 200 mL of diisopropyl ether, followed by stirring for 14 hours. The precipitated solid was collected by filtration to obtain 53.2 g of methyl 4-[2-(4-{[cyano(cyclohexylidene)acetyl]amino}phenyl)ethyl]benzoate as a beige solid. ESI+: 403

(2) To a mixture of 53.2 of methyl 4-[2-(4-{[cyano(cyclohexylidene)acetyl]amino}phenyl)ethyl]benzoate, 4.5 g of sulfur, and 80 mL of DMF was added dropwise 12.0 mL of morpholine at room temperature. The reaction mixture was stirred at 50° C. for 1 hour. To the reaction mixture was added saturated brine, followed by extraction with ethyl acetate, and then the organic layer was washed with water and brine. After drying over anhydrous sodium sulfate and filtration, the solvent was evaporated under reduced pressure, and to the obtained residue was added isopropanol, followed by suspending. The precipitated solid was collected by filtration to obtain 43.1 g of methyl 4-[2-(4-{[(2-amino-4,5,6,7-tetrahydro-1-benzothiophen-3-yl)carbonyl]amino}phenyl)ethyl]benzoate as a beige solid.

Preparation Example 6

A mixture of 43.0 g of methyl 4-[2-(4-{[(2-amino-4,5,6,7-tetrahydro-1-benzothiophen-3-yl)carbonyl]amino}phenyl)ethyl]benzoate, 14.0 mL of triethylamine, and 215 mL of dichloromethane was added dropwise to a mixture of 24.8 g of 3-(chlorosulfonyl)benzoyl chloride and 430 mL of dichloromethane under ice-cooling, followed by stirring for 2 hours at room temperature. The reaction mixture was concentrated under reduced pressure and the residue was washed with ethanol to obtain 59.5 g of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate as a yellow solid.

Preparation Example 7

(1) To a mixture of 19.3 g of methyl 4-(3-{4-[(cyanoacetyl)amino]phenyl}propyl)benzoate, 18 mL of cyclohexanone, and 100 mL of toluene was added dropwise 5.0 mL of morpholine at room temperature. In a reaction device in which a Dean-Stark type dehydration tube was installed, the reaction mixture was stirred for 8 hours under heating and refluxing. The reaction mixture was cooled to room temperature and then concentrated under reduced pressure. The obtained residue was purified by silica gel column chromatography (n-hexane-chloroform and ethyl acetate-chloroform) to obtain methyl 4-[3-(4-{[cyano(cyclohexylidene)acetyl]amino}phenyl)propyl]benzoate in the form of a reddish brown amorphous substance as a crude product. ESI+:417

(2) A mixture of methyl 4-[3-(4-{[cyano(cyclohexylidene)acetyl]amino}phenyl)propyl]benzoate which is the crude product obtained in (1), 2.0 g of sulfur, 5.0 mL of morpholine, and 10 mL of DMF was stirred at 50° C. for 1 hour. The reaction liquid was left to stand to cool, and then to the residue was added water, followed by extraction with ethyl acetate. The organic layer was washed with water and saturated brine, and then dried over anhydrous sodium sulfate. After filtration and then concentration under reduced pressure, the obtained residue was purified by silica gel column chromatography (ethyl acetate-chloroform) to obtain 21.7 g of methyl 4-[3-(4-{[(2-amino-4,5,6,7-tetrahydro-1-benzothiophen-3-yl)carbonyl]amino}phenyl)propyl]benzoate as a reddish brown amorphous substance.

Preparation Example 8

To a mixture of 3.34 g of methyl 4-[3-(4-{[(2-amino-4,5,6,7-tetrahydro-1-benzothiophen-3-yl)carbonyl]amino}phenyl)propyl]benzoate, 2.2 mL of triethylamine, and 40 mL of dichloromethane were added a mixture of 2.2 g of 3-(chlorosulfonyl)benzoyl chloride and 10 mL of dichloromethane under ice-cooling, followed by stirring at room temperature for 7 hours. The reaction mixture was concentrated under reduced pressure and the residue was suspended in ethanol. The precipitate was collected by filtration to obtain 1.42 g of methyl 4-[3-(4-{[(2-{[3-(chlorosulfonyl)benzoyl]amino}-4,5,6,7-tetrahydro-1-benzothiophen-3-yl)carbonyl]amino}phenyl)propyl]benzoate as a yellow solid.

Preparation Example 9

To a mixture of 3.35 g of cyclopropylamine, 1.0 mL of acetic acid, 9.34 g of sodium triacetoxyborohydride, and 30 mL of 1,2-dichloroethane was added dropwise 5.00 g of ethyl 4-oxocyclohexane carboxylate at room temperature. After stirring at room temperature for 14 hours, to the reaction mixture was added a saturated aqueous sodium hydrogen carbonate solution to quench the reaction. To the reaction mixture was added chloroform, followed by extraction and then the organic layer was dried over anhydrous sodium sulfate. After filtration, the solvent was evaporated under reduced pressure and the obtained residue was purified by silica gel column chromatography (aqueous ammonia-methanol-chloroform) to obtain 5.62 g of ethyl 4-(cyclopropylamino)cyclohexane carboxylate as a colorless oily substance.

Preparation Example 10

25.6 g of trans-4-aminocyclohexane carboxylic acid was suspended in 150 mL of methanol, and 15.7 mL of thionyl chloride was added dropwise thereto under ice-cooling.
After stirring at room temperature for 5 hours, the reaction mixture was concentrated under reduced pressure and the residue was suspended in diisopropyl ether. The precipitate was collected by filtration to obtain 34.0 g of methyl trans-4-aminocyclohexane carboxylate hydrochloride as a white solid.

Preparation Example 11

(1) A mixture of 1.30 g of methyl trans-4-aminocyclohexane carboxylate hydrochloride, 1.65 g of sodium acetate, 5.2 mL of acetone, 1.3 mL of acetic acid, and 13 mL of 1,2-dichloroethane was stirred at room temperature for 30 minutes, and then 4.27 g of sodium triacetoxyborohydride was added thereto, followed by stirring at room temperature for 2 hours. To the reaction mixture were added 4.64 g of potassium carbonate and 10 mL of water, followed by stirring at room temperature for 1 hour and concentrating under reduced pressure. The residue was purified by silica gel column chromatography (chloroform-methanol) to obtain a colorless oily substance. To the obtained oily substance were added 2.93 g of di-tert-butyl dicarbonate and 13 mL of 1,4-dioxane, followed by stirring at room temperature for 2 hours and then at 60° C. overnight. The reaction mixture was concentrated under reduced pressure and the obtained residue was purified by silica gel column chromatography (hexane-ethyl acetate) to obtain 1.46 g of methyl trans-4-[(tert-butoxycarbonyl)(isopropyl)amino]cyclohexane carboxylate as a colorless oily substance. ESI+: 300

(2) To a mixture of 1.8 g of methyl trans-4-[(tert-butoxycarbonyl)(isopropyl)amino]cyclohexane carboxylate and 20 mL of ethyl acetate were added 20 mL of a 4.0 M hydrogen chloride/ethyl acetate solution, followed by stirring at room temperature for 3 hours. The reaction mixture was concentrated under reduced pressure to obtain 1.18 g of methyl trans-4-(isopropylamino)cyclohexane carboxylate hydrochloride as a colorless solid.

Preparation Example 12

A mixture of 2.00 g of methyl 3-(bromomethyl)benzoate, 1.55 g of isopropylamine, and 10 mL of DMF was stirred at room temperature overnight. The reaction mixture was concentrated under reduced pressure and the obtained residue was purified by silica gel column chromatography (chloroform-methanol) to obtain 1.20 g of methyl 3-[(isopropylamino)methyl]benzoate as a colorless solid.

Preparation Example 13

To a mixture of 23.9 g of 3-(chlorosulfonyl)benzoyl chloride, 7.9 mL of pyridine, and 100 mL of dichloromethane was added dropwise 14 mL of 2-(trimethylsilyl)ethanol under ice-cooling, followed by stirring at room temperature for 2 hours. To the reaction mixture was added water, followed by extraction with chloroform, and the organic layer was concentrated under reduced pressure. The obtained residue was purified by silica gel column chromatography (hexane-ethyl acetate) to obtain 29.4 g of 2-(trimethylsilyl)ethyl 3-(chlorosulfonyl)benzoate as a colorless solid.

Preparation Example 14

A mixture of 604 mg of methyl trans-4-aminocyclohexane carboxylate hydrochloride, 0.90 mL of triethylamine, and 10 mL of dichloromethane was stirred at room temperature for 30 minutes, and 10 mL of pyridine and 1.00 g of 2-(trimethylsilyl)ethyl 3-(chlorosulfonyl)benzoate were added thereto in this order, followed by stirring at room temperature overnight. The reaction mixture was concentrated under reduced pressure, and to the residue was added an aqueous citric acid solution, followed by extraction with ethyl acetate. The organic layer was washed with saturated brine, dried over anhydrous sodium sulfate, and concentrated under reduced pressure. The obtained residue was purified by silica gel column chromatography (hexane-ethyl acetate) to obtain 1.27 g of 2-(trimethylsilyl)ethyl 3-{[trans-4-(methoxycarbonyl)cyclohexyl]sulfamoyl}benzoate as a colorless oily substance.

Preparation Example 15

A mixture of 450 mg of 2-(trimethylsilyl)ethyl 3-{[trans-4-(methoxycarbonyl)cyclohexyl]sulfamoyl}benzoate, 0.15 mL of ethyl iodide, 422 mg of potassium carbonate, and 4.5 mL of DMF was stirred at 65° C. overnight. To the reaction mixture was added water, followed by extraction with ethyl acetate. Then, the organic layer was washed with water and saturated brine in this order, dried over anhydrous sodium sulfate, and then concentrated under reduced pressure to obtain a colorless oily substance. To the obtained oily substance were added a solution of tetrabutyl ammonium fluoride (TBAF) in THF (1.0 M, 2.0 mL) and 4.5 mL of THF, followed by stirring at room temperature for 2 hours. To the reaction mixture was added 0.2 M hydrochloric acid, followed by extraction with ethyl acetate. The organic layer was washed with 0.2 M hydrochloric acid, water, and saturated brine in this order, dried over anhydrous sodium sulfate, and concentrated under reduced pressure to obtain 355 mg of 3-{ethyl[trans-4-(methoxycarbonyl)cyclohexyl]sulfamoyl}benzoic acid as a colorless solid.

Preparation Example 16

To a mixture of 1.00 g of 2-(trimethylsilyl)ethyl 3-{[trans-4-(methoxycarbonyl)cyclohexyl]sulfamoyl}benzoate and 10 mL of DMF were added 0.63 g of 2-bromoethylmethyl ether and 0.94 g of potassium carbonate at room temperature, followed by stirring at 60° C. overnight. The reaction mixture was cooled to room temperature, and then water was added thereto, followed by extraction with ethyl acetate. The organic layer was washed with water and saturated brine in this order, and dried over anhydrous sodium sulfate. The resultant was concentrated under reduced pressure, and to a mixture of the obtained residue and 10 mL of THF was added a solution of TBAF in THF (1.0 M, 4.0 mL), followed by stirring at room temperature for 3 hours. A solution of TBAF in THF (1.0 M, 2.0 mL) was further added thereto, followed by stirring at room temperature for 1.5 hours. The reaction mixture was diluted with ethyl acetate, and then washed with 0.2 M hydrochloric acid, water, and saturated brine in this order. The obtained organic layer was dried over anhydrous sodium sulfate, and then concentrated under reduced pressure to obtain 915 mg of 3-{[trans-4-(methoxycarbonyl)cyclohexyl](2-methoxyethyl)sulfamoyl}benzoic acid as a colorless amorphous solid.

Preparation Example 17

(1) A mixture of 734 mg of methyl trans-4-(isopropylamino)cyclohexane carboxylate hydrochloride, 0.90 mL of triethylamine, and 10 mL of dichloromethane was stirred at room temperature for 30 minutes, and 10 mL of pyridine and 1.00 g of 2-(trimethylsilyl)ethyl 3-(chlorosulfonyl)benzoate were added thereto in this order, followed by stirring at room temperature overnight. The reaction mixture was concentrated under reduced pressure, and to the residue was added an aqueous citric acid solution, followed by extraction with ethyl acetate. The organic layer was washed with saturated brine, then dried over anhydrous sodium sulfate, and concentrated under reduced pressure. The residue was purified by silica gel column chromatography (hexane-ethyl acetate) to obtain 311 mg of 2-(trimethylsilyl)ethyl 3-{isopropyl[trans-4-(methoxycarbonyl)cyclohexyl]sulfamoyl}benzoate as a pale yellow solid. ESI+: 484

(2) A mixture of 305 mg of 2-(trimethylsilyl)ethyl 3-{isopropyl[trans-4-(methoxycarbonyl)cyclohexyl]sulfamoyl}benzoate, a solution of TBAF in THF (1.0 M, 1.0 mL), and 3.0 mL of THF was stirred at room temperature for 2 hours. To the reaction mixture was added 0.2 M hydrochloric acid, followed by extraction with ethyl acetate. The organic layer was washed with 0.2 M hydrochloric acid, water, and saturated brine in this order, then dried over anhydrous sodium sulfate, and concentrated under reduced pressure to obtain 240 mg of 3-{isopropyl[trans-4-(methoxycarbonyl)cyclohexyl]sulfamoyl}benzoic acid as a colorless oil.

Preparation Example 18

(1) A mixture of 2.00 g of 2-(trimethylsilyl)ethyl 3-(chlorosulfonyl)benzoate, 1.2 mL of cyclopropylamine, and 20 mL of pyridine was stirred at room temperature overnight. The reaction mixture was concentrated under reduced pressure, and to the residue was added an aqueous citric acid solution, followed by extraction with ethyl acetate. The organic layer was washed with 1.0 M hydrochloric acid and saturated brine in this order, then dried over anhydrous sodium sulfate, and concentrated under reduced pressure to obtain 2.12 g of 2-(trimethylsilyl)ethyl 3-(cyclopropylsulfamoyl)benzoate as a pale yellow oily substance. EI: 341

(2) A mixture of 2.12 g of 2-(trimethylsilyl)ethyl 3-(cyclopropylsulfamoyl)benzoate, 1.45 g of ethyl 4-bromobutyrate, 2.57 g of potassium carbonate, and 21 mL of DMF was stirred at 80° C. overnight. To the reaction mixture was added water, followed by extraction with ethyl acetate. The organic layer was washed with water and saturated brine in this order, then dried over anhydrous sodium sulfate, and concentrated under reduced pressure. The residue was purified by silica gel column chromatography (hexane-ethyl acetate) to obtain 2.48 g of 2-(trimethylsilyl)ethyl 3-[cyclopropyl(4-ethoxy-4-oxobutyl)sulfamoyl]benzoate as a colorless oily substance. ESI+: 456

(3) A mixture of 2.48 g of 2-(trimethylsilyl)ethyl 3-[cyclopropyl(4-ethoxy-4-oxobutyl)sulfamoyl]benzoate, a solution of TBAF in THF (1.0 M, 10 mL), and 25 mL of THF was stirred at room temperature for 2 hours. To the reaction mixture was added 0.2 M hydrochloric acid, followed by extraction with ethyl acetate. The organic layer was washed with 0.2 M hydrochloric acid, water, saturated brine in this order, then dried over anhydrous sodium sulfate, and concentrated under reduced pressure to obtain 1.87 g of 3-[cyclopropyl(4-ethoxy-4-oxobutyl)sulfamoyl]benzoic acid as a colorless solid.

Preparation Example 19

(1) A mixture of 774 mg of ethyl 1-aminocyclopropane-1-carboxylate hydrochloride, 1.4 mL of triethylamine, and 15 mL of dichloromethane was stirred at room temperature for 30 minutes, and 15 mL of pyridine and 1.50 g of 2-(trimethylsilyl)ethyl 3-(chlorosulfonyl)benzoate were added thereto in this order, followed by stirring at room temperature overnight. The reaction mixture was concentrated under reduced pressure, and to the residue was added an aqueous citric acid solution, followed by extraction with ethyl acetate. The organic layer was washed with saturated brine, then dried over anhydrous sodium sulfate, and concentrated under reduced pressure. The obtained residue was purified by silica gel column chromatography (hexane-ethyl acetate) to obtain 1.80 g of 2-(trimethylsilyl)ethyl 3-{[1-(ethoxycarbonyl)cyclopropyl]sulfamoyl}benzoate as a pale yellow oily substance.

(2) A mixture of 450 mg of 2-(trimethylsilyl)ethyl 3-{[1-(ethoxycarbonyl)cyclopropyl]sulfamoyl}benzoate, 0.22 mL of isopropyl iodide, 451 mg of potassium carbonate, and 4.5 mL of DMF were stirred at 65° C. overnight. To the reaction mixture was added water, followed by extraction with ethyl acetate. Then, the organic layer was washed with water and saturated brine in this order, dried over anhydrous sodium sulfate, and then concentrated under reduced pressure to obtain a pale yellow oily substance. To the obtained oily substance were added a solution of TBAF in THF (1.0 M, 2.0 mL) and 4.5 mL of THF, followed by stirring at room temperature for 2 hours. To the reaction mixture was added 0.2 M hydrochloric acid, followed by extraction with ethyl acetate. The organic layer was washed with 0.2 M hydrochloric acid, water, and saturated brine in this order, and then dried over anhydrous sodium sulfate. The resultant was concentrated under reduced pressure to obtain 319 mg of 3-{[1-(ethoxycarbonyl)cyclopropyl](isopropyl)sulfamoyl}benzoic acid as a colorless oily substance.

Preparation Example 20

A mixture of 2.00 g of 3-(chlorosulfonyl)benzoic acid, 1.37 g of methyl 4-aminobenzoate, and 20 mL of pyridine was stirred at room temperature overnight, and then the reaction mixture was concentrated under reduced pressure. The obtained residue was purified by silica gel column chromatography (chloroform-methanol) to obtain 665 mg of 3-{[4-(methoxycarbonyl)phenyl]sulfamoyl}benzoic acid as a pink solid.

Preparation Example 21

(1) A mixture of 1.50 g of 2-(trimethylsilyl)ethyl 3-(chlorosulfonyl)benzoate, 772 mg of methyl 4-(methylamino)benzoate, and 15 mL of pyridine was stirred at room temperature overnight, and then the reaction mixture was concentrated under reduced pressure. The obtained residue was purified by silica gel column chromatography (hexane-ethyl acetate) to obtain 1.54 g of 2-(trimethylsilyl)ethyl 3-{[4-(methoxycarbonyl)phenyl](methyl)sulfamoyl}benzoate as a colorless oily substance. ESI+: 450

(2) A mixture of 1.5 g of 2-(trimethylsilyl)ethyl 3-{[4-(methoxycarbonyl)phenyl](methyl)sulfamoyl}benzoate, a solution of TBAF in THF (1.0 M, 7.0 mL), and 15 mL of THF was stirred at room temperature for 2 hours. To the reaction mixture was added 0.2 M hydrochloric acid, followed by extraction with ethyl acetate. The organic layer was washed with 0.2 M hydrochloric acid, water, and saturated brine in this order, then dried over anhydrous sodium sulfate, and concentrated under reduced pressure to obtain 1.11 g of 3-{[4-(methoxycarbonyl)phenyl](methyl)sulfamoyl}benzoic acid as a colorless solid.

Preparation Example 22

To a mixture of 1.04 g of 2-(trimethylsilyl)ethyl 3-(chlorosulfonyl)benzoate and 10 mL of pyridine was added 512 mg of methyl 4-aminobenzoate, followed by stirring at room temperature for 1 hour. To the reaction mixture was added a 10% aqueous citric acid solution, followed by extraction with ethyl acetate. The organic layer was washed with saturated brine and dried over anhydrous sodium sulfate. The solvent was evaporated under reduced pressure and the obtained residue was purified by silica gel column chromatography (hexane-ethyl acetate) to obtain 1.25 g of 2-(trimethylsilyl)ethyl 3-{[4-(methoxycarbonyl)phenyl]sulfamoyl}benzoate as a white solid.

Preparation Example 23

To a mixture of 2.09 g of 2-(trimethylsilyl)ethyl 3-(chlorosulfonyl)benzoate and 20 mL of methylene chloride were added 982 mg of methyl 2-aminobenzoate and 2.10 mL of pyridine under ice-cooling, followed by stirring at room temperature for 15 hours. To the reaction mixture was added a 10% aqueous citric acid solution, followed by extraction with ethyl acetate. The organic layer was washed with saturated brine and dried over anhydrous sodium sulfate. The solvent was evaporated under reduced pressure, and the obtained residue was purified by silica gel column chromatography (hexane-ethyl acetate) to obtain 2.61 g of methyl 2-{[(3-{[2-(trimethylsilyl)ethoxy]carbonyl}phenyl)sulfonyl]amino}benzoate as a colorless oily substance.

Preparation Example 24

To a mixture of 2.0 g of 2-(trimethylsilyl)ethyl 3-(chlorosulfonyl)benzoate and 40 mL of dichloromethane were added 5.0 mL of pyridine, 1.0 g of methyl 6-aminonicotinate, and 761 mg of N,N-dimethylpyridin-4-amine, followed by stirring at room temperature for 14 hours. The reaction mixture was concentrated under reduced pressure, and then to the residue was added a 10% aqueous citric acid solution, followed by extraction with ethyl acetate. The organic layer was washed with a saturated aqueous sodium hydrogen carbonate solution, and saturated brine in this order and dried over magnesium sulfate. The solvent was evaporated under reduced pressure, and then the obtained residue was purified by silica gel column chromatography (chloroform-ethyl acetate) to obtain 1.8 g of methyl 6-{[(3-{[2-(trimethylsilyl)ethoxy]carbonyl}phenyl)sulfonyl]amino}nicotinate as a colorless powder.

Preparation Example 25

(1) To a mixture of 320 mg of 2-(trimethylsilyl)ethyl 3-{[4-(methoxycarbonyl)phenyl]sulfamoyl}benzoate and 5 mL of acetonitrile were added 203 mg of potassium carbonate and 0.119 mL of iodoethane. After stirring at 70° C. for 5 hours, 102 mg of potassium carbonate and 0.059 mL of iodoethane were added thereto, followed by stirring at 70° C. for 10 hours. To the reaction mixture was added water, followed by extraction with ethyl acetate. The organic layer was washed with saturated brine and dried over anhydrous sodium sulfate. The solvent was evaporated under reduced pressure, and the obtained residue was purified by silica gel column chromatography (hexane-ethyl acetate) to obtain 334 mg of a 2-(trimethylsilyl)ethyl 3-{ethyl[4-(methoxycarbonyl)phenyl]sulfamoyl}benzoate as a colorless oily substance. ESI+: 464

(2) To a mixture of 330 mg of 2-(trimethylsilyl)ethyl 3-{ethyl[4-(methoxycarbonyl)phenyl]sulfamoyl}benzoate and 5.0 mL of THF was added a solution of TBAF in THF (1.0 M, 1.42 mL), followed by stirring at room temperature for 15 hours. To the reaction mixture was added a 0.1 M aqueous hydrochloric acid solution, followed by extraction with ethyl acetate. The organic layer was washed with a 0.1 M aqueous hydrochloric acid solution and a 10% aqueous citric acid solution, and dried over anhydrous sodium sulfate. The solvent was evaporated under reduced pressure to obtain 238 mg of 3-{ethyl[4-(methoxycarbonyl)phenyl]sulfamoyl}benzoic acid as a white solid.

Preparation Example 26

(1) To a mixture of 500 mg of methyl 6-{[(3-{[2-(trimethylsilyl)ethoxy]carbonyl}phenyl)sulfonyl]amino}nicotinate and 10 mL of DMF were added 0.300 mL of 1-iodopropane and 400 mg of potassium carbonate, followed by stirring at 80° C. for 5 hours. The reaction mixture was left to stand to cool and then water was added thereto, followed by extraction with ethyl acetate. The organic layer was washed with saturated brine, and then dried over magnesium sulfate. The solvent was evaporated under reduced pressure, and then the residue was purified by silica gel column chromatography (chloroform-ethyl acetate) to obtain 200 mg of a methyl 6-{propyl[(3-{[2-(trimethylsilyl)ethoxy]carbonyl}phenyl)sulfonyl]amino}nicotinate as a colorless oily substance. ESI+: 479

(2) To a mixture of 175 mg of methyl 6-{propyl[(3-{[2-(trimethylsilyl)ethoxy]carbonyl}phenyl)sulfonyl]amino}nicotinate and 5 mL of THF was added dropwise a solution of TBAF in THF (1 M, 0.750 mL), followed by stirring at room temperature for 4 hours. To the reaction mixture was added 0.1 M hydrochloric acid, followed by extraction with ethyl acetate. The organic layer was washed with saturated brine, and then dried over magnesium sulfate. The solvent was evaporated under reduced pressure and then dried under reduced pressure to obtain 110 mg of 3-{[5-(methoxycarbonyl)pyridin-2-yl](propyl)sulfamoyl}benzoic acid as a colorless powder.

Preparation Example 27

Under an argon atmosphere, to a mixed liquid of 1.06 g of 1-isopropylpiperidin-4-amine, 1.00 g of potassium carbonate, and 5.0 mL of DMF was added dropwise a mixture of 0.70 g of ethyl 4-bromobutyrate and 2.0 mL of DMF under ice-cooling, followed by washing with 3.0 mL of DMF. After stirring at room temperature for 96 hours, the reaction mixture was concentrated under reduced pressure. The obtained residue was purified by silica gel column chromatography (aqueous ammonia-methanol-chloroform) to obtain 0.47 g of ethyl 4-[(1-isopropylpiperidin-4-yl)amino]butyrate as a yellow oily substance.

Preparation Example 28

To a mixture of 4.76 g of 2-cyano-N-(4-methoxyphenyl)acetamide and 20 mL of DMF were added 2.45 g of cyclohexanone, 880 mg of sulfur, and 2.18 mL of morpholine, followed by stirring at 50° C. for 6 hours. The reaction mixture was concentrated under reduced pressure and the obtained residue was purified by silica gel column chromatography (hexane-ethyl acetate) to obtain 2.0 g of 2-amino-N-(4-methoxyphenyl)-4,5,6,7-tetrahydro-1-benzothiophene-3-carboxamide as a pale yellow solid.

Preparation Example 29

Under ice-cooling, to a mixture of 18.0 g of cyanoacetic acid and 25 mL of oxalyl chloride were added 0.07 mL of DMF and 10 mL of dichloromethane, followed by stirring at room temperature for 3 hours. The reaction mixture was concentrated under reduced pressure, and then to the residue was added toluene, followed by further concentrating under reduced pressure. This procedure was repeated and excess hydrogen chloride and oxalyl chloride were removed. A mixture of the obtained crude product and 50 mL of dichloromethane was added to a mixture of 80 mL of a 1 M aqueous sodium hydroxide solution, 300 mL of dichloromethane, and 14.3 g of 4-(pyridin-4-ylmethyl)aniline under ice-cooling. During mixing the reagent, a 1 M aqueous sodium hydroxide solution was added on time to adjust the reaction solution to be kept alkaline. After stirring at room temperature for 30 minutes, the organic layer was collected by separation and the aqueous layer was extracted with dichloromethane. The combined organic layer was dried over anhydrous sodium sulfate and then the solvent was evaporated under reduced pressure. The obtained residue was recrystallized from ethanol to obtain 10.2 g of 2-cyano-N-[4-(pyridin-4-ylmethyl)phenyl]acetamide as a pale yellow solid.

Preparation Example 30

To a mixture of 5.02 g of 2-cyano-N-[4-(pyridin-4-ylmethyl)phenyl]acetamide and 30 mL of DMF were added 2.0 g of cyclohexanone, 720 mg of sulfur, and 1.78 mL of morpholine at room temperature, followed by stirring at 50° C. overnight. The reaction mixture was concentrated under reduced pressure and the residue was suspended in ethanol. The precipitate was collected by filtration to obtain 1.19 g of 2-amino-N-[4-(pyridin-4-ylmethyl)phenyl]-4,5,6,7-tetrahydro-1-benzothiophene-3-carboxamide as a beige solid.

In the same manner as in the method of Preparation Example 9, the compound of Preparation Example 9-1 was prepared; in the same manner as in the method of Preparation Example 15, the compounds of Preparation Examples 15-1 and 15-2 were prepared; in the same manner as in the method of Preparation Example 18, the compound of Preparation Example 18-1 was prepared; in the same manner as in the method of Preparation Example 19, the compounds of Preparation Examples 19-1 to 19-3 were prepared; in the same manner as in the method of Preparation Example 22, the compound of Preparation Example 22-1 was prepared; in the same manner as in the method of Preparation Example 23, the compound of Preparation Example 23-1 was prepared; in the same manner as in the method of Preparation Example 25, the compounds of Preparation Examples 25-1 to 25-3 were prepared; in the same manner as in the method of Preparation Example 26, the compounds of Preparation Examples 26-1 to 26-3 were prepared; and in the same manner as in the method of Preparation Example 27, the compound of Preparation Example 27-1 was prepared by using corresponding starting materials, respectively. Further, the structures and the physicochemical data of the Preparation Example compounds are shown in Tables below.

Example 1

A mixture of 319 mg of 3-{ethyl[trans-4-(methoxycarbonyl)cyclohexyl]sulfamoyl}benzoic acid, 0.10 mL of oxalyl chloride, 2.5 mL of dichloromethane, and one drop of DMF was stirred at room temperature for 2 hours, and then the reaction mixture was concentrated under reduced pressure. A mixture of the obtained crude product and 2.5 mL of dichloromethane was added to a mixture of 0.050 mL of pyridine, 250 mg of methyl 4-[2-(4-{[(2-amino-4,5,6,7-tetrahydro-1-benzothiophen-3-yl)carbonyl]amino}phenyl)ethyl]benzoate, and 2.5 mL of dichloromethane, followed by stirring at room temperature overnight. The reaction mixture was purified by silica gel column chromatography (hexane-chloroform) to obtain 320 mg of methyl 4-(2-{4-[({2-[(3-{ethyl[trans-4-(methoxycarbonyl)cyclohexyl]sulfamoyl}benzoyl)amino]-4,5,6,7-tetrahydro-1-benzothiophen-3-yl}carbonyl)amino]phenyl}ethyl)benzoate as a yellow foamed solid.

Example 2

A mixture of 300 mg of methyl 4-(2-{4-[({2-[(3-{ethyl[trans-4-(methoxycarbonyl)cyclohexyl]sulfamoyl}benzoyl)amino]-4,5,6,7-tetrahydro-1-benzothiophen-3-yl}carbonyl)amino]phenyl}ethyl)benzoate, 1.5 mL of a 1.0 M aqueous sodium hydroxide solution, and 3.0 mL of ethanol was heated and refluxed overnight. The reaction mixture was concentrated under reduced pressure, and then to the obtained residue were added water, 300 mg of citric acid, and dichloromethane in this order, and the precipitate was collected by filtration. For the filtrate, the organic layer was separated and evaporated under reduced pressure. The firstly collected solid and the concentrate of the filtrate were mixed and the mixture was purified by silica gel column chromatography (chloroform-methanol). The crude product was washed with diethyl ether to obtain 203 mg of 4-{2-[4-({[2-({3-[(trans-4-carboxycyclohexyl)(ethyl)sulfamoyl]benzoyl}amino)-4,5,6,7-tetrahydro-1-benzothiophen-3-yl]carbonyl}amino)phenyl]ethyl}benzoic acid as a pale yellow crystal.

Example 3

A mixture of 300 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 298 mg of ethyl 4-(cyclopropylamino)cyclohexane carboxylate, and 3.0 mL of dichloromethane was stirred at room temperature overnight. The reaction mixture was concentrated under reduced pressure, and then the residue was purified by silica gel column chromatography (chloroform only) to obtain 314 mg of methyl 4-(2-{4-[({2-[(3-{cyclopropyl[4-(ethoxycarbonyl)cyclohexyl]sulfamoyl}benzoyl)amino]-4,5,6,7-tetrahydro-1-benzothiophen-3-yl}carbonyl)amino]phenyl}ethyl)benzoate as a yellow powder solid.

Examples 4 and 5

A mixture of 300 mg of methyl 4-(2-{4-[({2-[(3-{cyclopropyl[4-(ethoxycarbonyl)cyclohexyl]sulfamoyl}benzoyl)amino]-4,5,6,7-tetrahydro-1-benzothiophen-3-yl}carbonyl)amino]phenyl}ethyl)benzoate, 1.0 mL of a 1.0 M aqueous sodium hydroxide solution, and 3.0 mL of ethanol was heated and refluxed for 3 days. The reaction mixture was concentrated under reduced pressure and the residue was neutralized with 1.0 M hydrochloric acid, and then the precipitate was collected by filtration. The obtained solid was purified by silica gel column chromatography (chloroform-methanol) to obtain 4-{2-[4-({[2-({3-[(trans-4-carboxycyclohexyl)(cyclopropyl)sulfamoyl]benzoyl}amino)-4,5,6,7-tetrahydro-1-benzothiophen-3-yl]carbonyl}amino)phenyl]ethyl}benzoic acid (high polarity product) and 4-{2-[4-({[2-({3-[(cis-4-carboxycyclohexyl)(cyclopropyl)sulfamoyl]benzoyl}amino)-4,5,6,7-tetrahydro-1-benzothiophen-3-yl]carbonyl}amino) phenyl]ethyl}benzoic acid (low polarity product). The products were each suspended in ethyl acetate-hexane to obtain 114 mg of 4-{2-[4-({[2-({3-[(trans-4-carboxycyclohexyl)(cyclopropyl)sulfamoyl]benzoyl}amino)-4,5,6,7-tetrahydro-1-benzothiophen-3-yl]carbonyl}amino)phenyl]ethyl}benzoic acid (Example 4) and 56 mg of 4-{2-[4-({[2-({3-[(cis-4-carboxycyclohexyl)(cyclopropyl)sulfamoyl]benzoyl}amino)-4,5,6,7-tetrahydro-1-benzothiophen-3-yl]carbonyl}amino)phenyl]ethyl}benzoic acid (Example 5), respectively, as colorless crystals.

Example 6

A mixture of 250 mg of methyl 4-[2-(4-{[(2-{[3-(cyclopropylsulfamoyl)benzoyl]amino}-4,5,6,7-tetrahydro-1-benzothiophen-3-yl)carbonyl]amino}phenyl)ethyl]benzoate, 95 mg of bromoethyl acetate, 105 mg of potassium carbonate, and 2.5 mL of DMF was stirred at 80° C. overnight. To the reaction mixture was added an aqueous citric acid solution, followed by extraction with ethyl acetate. The organic layer was washed with water and saturated brine in this order, dried over anhydrous sodium sulfate, and then concentrated under reduced pressure. The residue was purified by silica gel column chromatography (hexane-chloroform) to obtain 218 mg of methyl 4-{2-[4-({[2-({3-[cyclopropyl(2-ethoxy-2-oxoethyl)sulfamoyl]benzoyl}amino)-4,5,6,7-tetrahydro-1-benzothiophen-3-yl]carbonyl}amino)phenyl]ethyl}benzoate as a yellow solid.

Example 7

A mixture of 250 mg of methyl 4-[2-(4-{[(2-{[3-(cyclopropylsulfamoyl)benzoyl]amino}-4,5,6,7-tetrahydro-1-benzothiophen-3-yl)carbonyl]amino}phenyl)ethyl]benzoate, 111 mg of methyl 5-bromopentanoate, 105 mg of potassium carbonate, and 2.5 mL of DMF was stirred at 80° C. overnight. Further, 42 mg of tetrabutyl ammonium iodide was added thereto, followed by stirring at 100° C. for 3 hours. In addition, 370 mg of methyl 5-bromopentanoate, 140 mg of tetrabutyl ammonium iodide, and 262 mg of potassium carbonate were added thereto, followed by stirring at 100° C. overnight. To the reaction mixture was added an aqueous citric acid solution, followed by extraction with ethyl acetate. The organic layer was washed with water and saturated brine in this order, dried over anhydrous sodium sulfate, and then concentrated under reduced pressure. The residue was purified by silica gel column chromatography (hexane-chloroform) to obtain 213 mg of methyl 4-{2-[4-({[2-({3-[cyclopropyl(5-methoxy-5-oxopentyl)sulfamoyl]benzoyl}amino)-4,5,6,7-tetrahydro-1-benzothiophen-3-yl]carbonyl}amino)phenyl]ethyl}benzoate as a yellow solid.

Example 8

A mixture of 200 mg of methyl 4-{2-[4-({[2-({3-[(4-ethoxy-4-oxobutyl)sulfamoyl]benzoyl}amino)-4,5,6,7-tetrahydro-1-benzothiophen-3-yl]carbonyl}amino)phenyl] ethyl}benzoate, 0.059 mL of ethyl iodide, 113 mg of potassium carbonate, and 2.0 mL of DMF was stirred at 60° C. overnight. To the reaction mixture was added an aqueous citric acid solution, followed by extraction with ethyl acetate. The organic layer was washed with water and saturated brine in this order, dried over anhydrous sodium sulfate, and then concentrated under reduced pressure. The obtained residue was purified by silica gel column chromatography (hexane-chloroform) to obtain 137 mg of methyl 4-{2-[4-({[2-({3-[(4-ethoxy-4-oxobutyl)(ethyl)sulfamoyl]benzoyl}amino)-4,5,6,7-tetrahydro-1-benzothiophen-3-yl]carbonyl}amino)phenyl]ethyl}benzoate as a yellow solid.

Example 9

A mixture of 250 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 125 mg of tert-butyl 3-(methylamino)propanoate, and 2.5 mL of dichloromethane was stirred at room temperature overnight. The reaction mixture was concentrated under reduced pressure and the obtained residue was purified by silica gel column chromatography (hexane-chloroform) to obtain 209 mg of methyl 4-{2-[4-({[2-({3-[(3-tert-butoxy-3-oxopropyl)(methyl)sulfamoyl]benzoyl}amino)-4,5,6,7-tetrahydro-1-benzothiophen-3-yl]carbonyl}amino)phenyl] ethyl}benzoate as a pale yellow foamed solid.

Example 10

A mixture of 200 mg of methyl 4-{2-[4-({[2-({3-[(3-tert-butoxy-3-oxopropyl)(methyl)sulfamoyl]benzoyl}amino)-4,5,6,7-tetrahydro-1-benzothiophen-3-yl]carbonyl}amino)phenyl]ethyl}benzoate, 2.0 mL of trifluoroacetic acid, and 2.0 mL of dichloromethane was stirred at room temperature for 4 hours. The reaction mixture was concentrated under reduced pressure, and to the obtained crude product were added 0.50 mL of a 5.0 M aqueous sodium hydroxide solution and 2.0 mL of ethanol, followed by heating and refluxing overnight. The reaction mixture was concentrated under reduced pressure and to the obtained residue were added water and citric acid (500 mg), followed by extraction with dichloromethane. The organic layer was concentrated under reduced pressure and the obtained residue was purified by silica gel column chromatography (chloroform-methanol). The crude product was washed with ethyl acetate to obtain 135 mg of 4-{2-[4-({[2-({3-[(2-carboxyethyl)(methyl)sulfamoyl]benzoyl}amino)-4,5,6,7-tetrahydro-1-benzothiophen-3-yl]carbonyl}amino)phenyl]ethyl}benzoic acid as a colorless crystal.

Example 11

A mixture of 3.00 g of 3-[cyclopropyl(4-ethoxy-4-oxobutyl)sulfamoyl]benzoic acid, 0.70 mL of oxalyl chloride, 33 mL of dichloromethane, and one drop of DMF was stirred at room temperature for 2 hours, and the reaction mixture was concentrated under reduced pressure. A mixture of the obtained crude product and 33 mL of dichloromethane was added to a mixture of 0.70 mL of pyridine, 3.33 g of methyl 4-[2-(4-{[(2-amino-4,5,6,7-tetrahydro-1-benzothiophen-3-yl)carbonyl]amino}phenyl)ethyl]benzoate, and 33 mL of dichloromethane, followed by stirring at room temperature for 2 hours. The reaction mixture was purified by silica gel column chromatography (hexane-chloroform) and column chromatography (ethyl acetate) using NH silica gel in this order. The obtained solid was washed with ethanol to obtain 4.82 g of methyl 4-{2-[4-({[2-({3-[cyclopropyl(4-ethoxy-4-oxobutyl)sulfamoyl]benzoyl}amino)-4,5,6,7-tetrahydro-1-benzothiophen-3-yl]carbonyl}amino)phenyl] ethyl}benzoate as a pale yellow solid.

Example 12

(1) A mixture of 4.82 g of methyl 4-{2-[4-({[2-({3-[cyclopropyl(4-ethoxy-4-oxobutyl)sulfamoyl]benzoyl}amino)-4,5,6,7-tetrahydro-1-benzothiophen-3-yl]carbonyl}amino)phenyl]ethyl}benzoate, 20 mL of a 1.0 M aqueous sodium hydroxide, and 50 mL of ethanol was heated and refluxed overnight. The reaction mixture was concentrated under reduced pressure and the residue was purified by ODS column chromatography (acetonitrile-water). To the crude product were added 1.0 M hydrochloric acid and dichloromethane in this order, and the precipitate was collected by filtration. To the obtained solid was added a 1.0 M aqueous sodium hydroxide solution for dissolution, followed by purifying by ODS column chromatography (acetonitrile-water). The product was lyophilized to obtain 1.86 g of sodium salt of 4-{2-[4-({[2-({3-[(3-carboxypropyl)(cyclopropyl)sulfamoyl]benzoyl}amino)-4,5,6,7-tetrahydro-1-benzothiophen-3-yl]carbonyl}amino)phenyl]ethyl}benzoic acid as a yellow powder solid. ESI+: 730

(2) To a mixture of 927 mg of sodium salt of 4-{2-[4-({[2-({3-[(3-carboxypropyl)(cyclopropyl)sulfamoyl]benzoyl}amino)-4,5,6,7-tetrahydro-1-benzothiophen-3-yl]carbonyl}amino)phenyl]ethyl}benzoic acid obtained in (1) and 9.3 mL of water was added 3.0 mL of 1.0 M hydrochloric acid, followed by stirring at room temperature for 1 hour. To the reaction mixture was added 9.3 mL of dichloromethane, and then the crystal was collected by filtration. The obtained crystal was washed with ethanol to obtain a colorless crystal. 168 mg of the obtained crystal was stirred in 16 mL of acetonitrile for 20 hours under heating and refluxing to obtain 158 mg of 4-{2-[4-({[2-({3-[(3-carboxypropyl)(cyclopropyl)sulfamoyl]benzoyl}amino)-4,5,6,7-tetrahydro-1-benzothiophen-3-yl]carbonyl}amino)phenyl]ethyl}benzoic acid as a colorless crystal.

Example 13

(1) A mixture of 600 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 390 mg of ethyl 1-aminocyclopropane carboxylate hydrochloride, 0.27 mL of triethylamine, and 6.0 mL of dichloromethane was stirred at room temperature overnight, and then the reaction mixture was concentrated under reduced pressure. The obtained residue was purified by silica gel column chromatography (hexane-chloroform) to obtain 523 mg of methyl 4-(2-{4-[({2-[(3-{[1-(ethoxycarbonyl)cyclopropyl]sulfamoyl}benzoyl)amino]-4,5,6,7-tetrahydro-1-benzothiophen-3-yl}carbonyl)amino]phenyl}ethyl)benzoate as a pale yellow solid. ESI+: 730

(2) A mixture of 250 mg of methyl 4-(2-{4-[({2-[(3-{[1-(ethoxycarbonyl)cyclopropyl]sulfamoyl}benzoyl)amino]-4,5,6,7-tetrahydro-1-benzothiophen-3-yl}carbonyl)amino]phenyl}ethyl)benzoate, 0.081 mL of ethyl iodide, 142 mg of potassium carbonate, and 2.5 mL of DMF was stirred at 60° C. overnight. To the reaction mixture was added an aqueous citric acid solution, followed by extraction with ethyl acetate. The organic layer was washed with water and saturated brine in this order, dried over anhydrous sodium sulfate, and then evaporated under reduced pressure. The obtained residue was purified by silica gel column chromatography (hexane-chloroform) to obtain 243 mg of methyl 4-(2-{4-[({2-[(3-{[1-(ethoxycarbonyl)cyclopropyl](ethyl)sulfamoyl}benzoyl)amino]-4,5,6,7-tetrahydro-1-benzothiophen-3-yl}carbonyl)amino]phenyl}ethyl)benzoate as a yellow solid.

Example 14

A mixture of 237 mg of methyl 4-(2-{4-[({2-[(3-{[1-(ethoxycarbonyl)cyclopropyl](ethyl)sulfamoyl}benzoyl)amino]-4,5,6,7-tetrahydro-1-benzothiophen-3-yl}carbonyl)amino]phenyl}ethyl)benzoate, 0.5 mL of a 5.0 M aqueous sodium hydroxide solution, and 2.4 mL of ethanol was heated and refluxed overnight. The reaction mixture was concentrated under reduced pressure, and to the residue were added water, citric acid, dichloromethane, and THF in this order. The organic layer was separated and then concentrated under reduced pressure, and the residue was purified by silica gel column chromatography (chloroform-methanol). The obtained crude product was washed with diethyl ether to obtain 142 mg of 4-{2-[4-({[2-({3-[(1-carboxycyclopropyl)(ethyl)sulfamoyl]benzoyl}amino)-4,5,6,7-tetrahydro-1-benzothiophen-3-yl]carbonyl}amino)phenyl]ethyl}benzoic acid as a pale yellow crystal.

Example 15

A mixture of 307 mg of 3-{[1-(ethoxycarbonyl)cyclopropyl](isopropyl)sulfamoyl}benzoic acid, 0.10 mL of oxalyl chloride, 2.5 mL of dichloromethane, and one drop of DMF was stirred at room temperature for 2 hours, and then the reaction mixture was concentrated under reduced pressure. A mixture of the obtained crude product and 2.5 mL of dichloromethane was added to a mixture of 0.050 mL of pyridine, 250 mg of methyl 4-[2-(4-{[(2-amino-4,5,6,7-tetrahydro-1-benzothiophen-3-yl)carbonyl]amino}phenyl)ethyl]benzoate, and 2.5 mL of methylene chloride, followed by stirring at room temperature overnight. The reaction mixture was purified by silica gel column chromatography (hexane-chloroform) to obtain 279 mg of methyl 4-(2-{4-[({2-[(3-{[1-(ethoxycarbonyl)cyclopropyl](isopropyl)sulfamoyl}benzoyl)amino]-4,5,6,7-tetrahydro-1-benzothiophen-3-yl}carbonyl)amino]phenyl}ethyl)benzoate as a yellow foamed solid.

Example 16

A mixture of 290 mg of methyl 4-(2-{4-[({2-[(3-{[1-(ethoxycarbonyl)cyclopropyl](isopropyl)sulfamoyl}benzoyl)amino]-4,5,6,7-tetrahydro-1-benzothiophen-3-yl}carbonyl)amino]phenyl}ethyl)benzoate, 1.5 mL of a 1.0 M aqueous sodium hydroxide solution, and 2.9 mL of ethanol was heated and refluxed overnight. The reaction mixture was concentrated under reduced pressure, and to the residue were added water, citric acid, dichloromethane, and THF in this order. The organic layer was separated and then concentrated under reduced pressure, and the residue was purified by silica gel column chromatography (chloroform-methanol). The crude purified product thus obtained was washed with diethyl ether to obtain 169 mg of 4-(2-{4-[({2-[(3-{[1-(ethoxycarbonyl)cyclopropyl](isopropyl)sulfamoyl}benzoyl)amino]-4,5,6,7-tetrahydro-1-benzothiophen-3-yl}carbonyl)amino]phenyl}ethyl)benzoic acid as a pale yellow solid.

Example 17

A mixture of 137 mg of 4-(2-{4-[({2-[(3-{[1-(ethoxycarbonyl)cyclopropyl](isopropyl)sulfamoyl}benzoyl)amino]-4,5,6,7-tetrahydro-1-benzothiophen-3-yl}carbonyl)amino]phenyl}ethyl)benzoic acid, 0.5 mL of a 5.0 M aqueous sodium hydroxide, and 1.4 mL of ethanol was heated and refluxed overnight. The reaction mixture was concentrated under reduced pressure, and to the residue were added water, citric acid, dichloromethane, and THF in this order. The organic layer was separated and then concentrated under reduced pressure, and the residue was purified by silica gel column chromatography (chloroform-methanol). The obtained crude product was washed with diethyl ether to obtain 74 mg of 4-{2-[4-({[2-({3-[(1-carboxycyclopropyl)(isopropyl)sulfamoyl]benzoyl}amino)-4,5,6,7-tetrahydro-1-benzothiophen-3-yl]carbonyl}amino)phenyl]ethyl}benzoic acid as a pale yellow crystal.

Example 18

To a mixture of 100 mg of methyl 4-[2-(4-{[(2-amino-4,5,6,7-tetrahydro-1-benzothiophen-3-yl)carbonyl]amino}phenyl)ethyl]benzoate and 2 mL of DMF were added 105 mg of 3-{[5-(methoxycarbonyl)pyridin-2-yl](propyl)sulfamoyl}benzoic acid, 110 mg of HATU, and 0.060 mL of N-ethyl diisopropylamine, followed by stirring at room temperature for 5 hours. To the reaction mixture was added water, followed by extraction with ethyl acetate. The organic layer was washed with saturated brine and then dried over anhydrous magnesium sulfate. The solvent was evaporated under reduced pressure and the residue was purified by silica gel column chromatography (hexane-ethyl acetate) to obtain 110 mg of methyl 6-[{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}(propyl)amino]nicotinate as a pale brown powder.

Example 19

(1) A mixture of 347 mg of 3-{[4-(methoxycarbonyl)phenyl]sulfamoyl}benzoic acid, 0.090 mL of oxalyl chloride, 3.0 mL of dichloromethane, and one drop of DMF was stirred at room temperature for 2 hours, and then the reaction mixture was concentrated under reduced pressure. A mixture of the obtained crude product and 3.0 mL of dichloromethane was added to a mixture of 0.071 mL of pyridine, 300 mg of methyl 4-[2-(4-{[(2-amino-4,5,6,7-tetrahydro-1-benzothiophen-3-yl)carbonyl]amino}phenyl)ethyl]benzoate, and 2.5 mL of dichloromethane, followed by stirring at room temperature overnight. The reaction mixture was purified by silica gel column chromatography (hexane-chloroform) to obtain 505 mg of methyl 4-({[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}amino)benzoate as a yellow foamed solid. ESI+: 752

(2) A mixture of 350 mg of methyl 4-({[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}amino)benzoate, 0.070 mL of isopropyl iodide, 193 mg of potassium carbonate, and 3.5 mL of DMF was stirred at 80° C. overnight. Further, 0.14 mL of isopropyl iodide was added thereto, followed by further stirring at 80° C. overnight. To the reaction mixture was added an aqueous citric acid solution, followed by extraction with ethyl acetate. The organic layer was washed with water and saturated brine in this order, then dried over anhydrous sodium sulfate, and concentrated under reduced pressure. The obtained residue was purified by silica gel column chromatography (hexane-chloroform) to obtain 264 mg of methyl 4-(isopropyl{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}amino)benzoate as a pale yellow solid.

Example 20

To a mixture of 238 mg of 3-{ethyl[4-(methoxycarbonyl)phenyl]sulfamoyl}benzoic acid and 5.0 mL of methylene chloride was added one drop of DMF, and then 0.075 mL of oxalyl chloride was added thereto under ice-cooling. After stirring at room temperature for 1 hour, the reaction mixture was concentrated under reduced pressure. To a mixture of the obtained residue and 5.0 mL of methylene chloride were added 0.053 mL of pyridine and 190 mg of methyl 4-[2-(4-{[(2-amino-4,5,6,7-tetrahydro-1-benzothiophen-3-yl)carbonyl]amino}phenyl)ethyl]benzoate, followed by stirring at room temperature for 1 hour. To the reaction mixture was added water, followed by extraction with ethyl acetate. The organic layer was washed with saturated brine and dried over anhydrous sodium sulfate. The solvent was evaporated under reduced pressure, and the obtained residue was purified by silica gel column chromatography (hexane-ethyl acetate). To the obtained yellow amorphous substance was added ethanol, followed by suspending, and the precipitate was collected by filtration to obtain 282 mg of methyl 4-(ethyl{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}amino)benzoate as a yellowish-white solid.

Example 21

To a mixture of 275 mg of methyl 4-(ethyl{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}amino)benzoate and 5.0 mL of methanol was added 2.0 mL of a 1 M aqueous sodium hydroxide solution, followed by stirring at 60° C. for 15 hours. The reaction mixture was concentrated under reduced pressure, then to the residue was added 1 M hydrochloric acid, and the precipitate was collected by filtration. The obtained yellowish-white solid was solidified with methanol and the precipitate was collected by filtration to obtain 248 mg of 4-{[(3-{[3-({4-[2-(4-carboxyphenyl)ethyl]phenyl}carbamoyl)-4,5,6,7-tetrahydro-1-benzothiophen-2-yl]carbamoyl}phenyl)sulfonyl](ethyl)amino}benzoic acid as yellowish-white crystal.

Example 22

To a mixture of 332 mg of 3-{ethyl[trans-4-(methoxycarbonyl)cyclohexyl]sulfamoyl}benzoic acid, one drop of DMF, and 3 mL of dichloromethane was added 0.11 mL of oxalyl chloride under ice-cooling, followed by stirring at room temperature for 4 hours. The reaction mixture was concentrated under reduced pressure, and then to a mixture of the obtained crude product and 3 mL of dichloromethane were added 0.11 mL of pyridine and 300 mg of methyl 4-[3-(4-{[(2-amino-4,5,6,7-tetrahydro-1-benzothiophen-3-yl)carbonyl]amino}phenyl)propyl]benzoate, followed by stirring at room temperature overnight. The reaction mixture was concentrated under reduced pressure, and then the obtained residue was purified by silica gel column chromatography (hexane-ethyl acetate and hexane-chloroform) to obtain 241 mg of methyl 4-(3-{4-[({2-[(3-{ethyl[trans-4-(methoxycarbonyl)cyclohexyl]sulfamoyl}benzoyl)amino]-4,5,6,7-tetrahydro-1-benzothiophen-3-yl}carbonyl)amino]phenyl}propyl)benzoate as a yellow amorphous solid.

Example 23

To a mixture of 230 mg of methyl 4-(3-{4-[({2-[(3-{ethyl[trans-4-(methoxycarbonyl)cyclohexyl]sulfamoyl}benzoyl)amino]-4,5,6,7-tetrahydro-1-benzothiophen-3-yl}carbonyl)amino]phenyl}propyl)benzoate, 2 mL of methanol, and 2 mL of THF was added 2 mL of a 1 M aqueous NaOH solution, followed by stirring at 60° C. for 2 days. The reaction mixture was cooled and then concentrated under reduced pressure. The obtained residue was diluted with water and then neutralized with 1 M hydrochloric acid. To the reaction mixture was added 0.5 mL of THF and the precipitate was collected by filtration. The obtained solid was suspended in 10 mL of ethanol, and then the precipitate was collected by filtration to obtain 147 mg of 4-{3-[4-({[2-({3-[(trans-4-carboxycyclohexyl)(ethyl)sulfamoyl]benzoyl}amino)-4,5,6,7-tetrahydro-1-benzothiophen-3-yl]carbonyl}amino)phenyl]propyl}benzoic acid as a beige crystal.

Example 24

A mixture of 300 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 247 mg of 2-methyl-pyrrolidine-2-carboxylic bromohydride, 0.17 mL of triethylamine, and 3.0 mL of dichloromethane was stirred at room temperature overnight. The reaction mixture was concentrated under reduced pressure and the residue was purified by silica gel column chromatography (methanol-chloroform) to obtain 164 mg of 1-{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}-2-methylproline as a yellow powder solid.

Example 25

A mixture of 160 mg of 1-{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}-2-methylproline, 1.0 mL of a 1.0 M aqueous sodium hydroxide solution, and 1.6 mL of methanol was heated and refluxed overnight. The reaction mixture was concentrated under reduced pressure and the residue was neutralized with 1.0 M hydrochloric acid. The precipitate was collected by filtration to obtain 133 mg of 1-[(3-{[3-({4-[2-(4-carboxyphenyl)ethyl]phenyl}carbamoyl)-4,5,6,7-tetrahydro-1-benzothiophen-2-yl]carbamoyl}phenyl)sulfonyl]-2-methylproline as a pale yellow solid.

Example 26

A mixture of 300 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 181 mg of 1-acetylpiperazine, and 3.0 mL of dichloromethane was stirred at room temperature overnight, and then the reaction mixture was concentrated under reduced pressure. The obtained residue was washed with ethanol and water in this order to obtain 305 mg of methyl 4-{2-[4-({[2-({3-[(4-acetylpiperazin-1-yl)sulfonyl]benzoyl}amino)-4,5,6,7-tetrahydro-1-benzothiophen-3-yl]carbonyl}amino)phenyl]ethyl}benzoate as a pale yellow solid.

Example 27

A mixture of 300 mg of methyl 4-{2-[4-({[2-({3-[(4-acetylpiperazin-1-yl)sulfonyl]benzoyl}amino)-4,5,6,7-tetrahydro-1-benzothiophen-3-yl]carbonyl}amino)phenyl]ethyl}benzoate, 1.5 mL of a 1.0 M aqueous sodium hydroxide solution, and 3.0 mL of ethanol was heated and refluxed overnight. The reaction mixture was concentrated under reduced pressure and the residue was neutralized with 1.0 M hydrochloric acid. Then, the precipitate was collected by filtration and the obtained solid was purified by silica gel column chromatography (methanol-chloroform) to obtain 116 mg of 4-{2-[4-({[2-({3-[(4-acetylpiperazin-1-yl)sulfonyl]benzoyl}amino)-4,5,6,7-tetrahydro-1-benzothiophen-3-yl]carbonyl}amino)phenyl]ethyl}benzoic acid as a colorless crystal.

Example 28

A mixture of 250 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 83 mg of 3-(methylamino)propane-1,2-diol, and 2.5 mL of dichloromethane was stirred at room temperature overnight. The reaction mixture was concentrated under reduced pressure and the residue was purified by silica gel column chromatography (hexane-chloroform) to obtain 241 mg of methyl 4-{2-[4-({[2-({3-[(2,3-dihydroxypropyl)(methyl)sulfamoyl]benzoyl}amino)-4,5,6,7-tetrahydro-1-benzothiophen-3-yl]carbonyl}amino)phenyl]ethyl}benzoate as a pale yellow foamed solid.

Example 29

A mixture of 230 mg of methyl 4-{2-[4-({[2-({3-[(2,3-dihydroxypropyl)(methyl)sulfamoyl]benzoyl}amino)-4,5,6,7-tetrahydro-1-benzothiophen-3-yl]carbonyl}amino)phenyl]ethyl}benzoate, 1.5 mL of a 1.0 M aqueous sodium hydroxide solution, and 2.3 mL of ethanol was heated and refluxed overnight. The reaction mixture was concentrated under reduced pressure, and to the residue were added water, citric acid, and dichloromethane in this order. The organic layer was separated and concentrated under reduced pressure. The obtained residue was solidified with THF-hexane to obtain 180 mg of 4-{2-[4-({[2-({3-[(2,3-dihydroxypropyl)(methyl)sulfamoyl]benzoyl}amino)-4,5,6,7-tetrahydro-1-benzothiophen-3-yl]carbonyl}amino)phenyl]ethyl}benzoic acid as a colorless solid.

Example 30

A mixture of 250 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 153 mg of N-methyl-D-glucamine, and 2.5 mL of dichloromethane was stirred at room temperature overnight. The reaction mixture was concentrated under reduced pressure and the residue was washed with water to obtain 256 mg of 1-deoxy-1-[{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}(methyl)amino]-D-glucitol as a yellow solid.

Example 31

A mixture of 250 mg of 1-deoxy-1-[{[3-({3-[(4-{2-[4-(methoxycarbonyl)phenyl]ethyl}phenyl)carbamoyl]-4,5,6,7-tetrahydro-1-benzothiophen-2-yl}carbamoyl)phenyl]sulfonyl}(methyl)amino]-D-glucitol, 1.5 mL of a 1.0 M aqueous sodium hydroxide solution, and 2.5 mL of ethanol was heated and refluxed overnight. The reaction mixture was concentrated under reduced pressure and the residue was purified by ODS silica gel column chromatography (acetonitrile-water). The product was lyophilized to obtain 33 mg of sodium 1-{[(3-{[3-({4-[2-(4-carboxylatophenyl)ethyl]phenyl}carbamoyl)-4,5,6,7-tetrahydro-1-benzothiophen-2-yl]carbamoyl}phenyl)sulfonyl](methyl)amino}-1-deoxy-D-glucitol as a yellow foamed solid.

Example 32

A mixture of 1.00 g of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 0.22 mL of cyclopropylamine, and 10 mL of dichloromethane was stirred at room temperature for 2 hours. The reaction mixture was purified by silica gel column chromatography (hexane-chloroform) to obtain 850 mg of methyl 4-[2-(4-{[(2-{[3-(cyclopropylsulfamoyl)benzoyl]amino}-4,5,6,7-tetrahydro-1-benzothiophen-3-yl)carbonyl]amino}phenyl)ethyl]benzoate as a pale yellow solid.

Example 33

A mixture of 600 mg of methyl 4-[2-(4-{[(2-{[3-(chlorosulfonyl)benzoyl]amino}-4,5,6,7-tetrahydro-1-benzothiophen-3-yl)carbonyl]amino}phenyl)ethyl]benzoate, 394 mg of ethyl 4-aminobutyrate hydrochloride, 0.27 mL of triethylamine, and 6.0 mL of dichloromethane was stirred at room temperature for 2 hours. The reaction mixture was purified by silica gel column chromatography (hexane-chloroform) to obtain 442 mg of methyl 4-{2-[4-({[2-({3-[(4-ethoxy-4-oxobutyl)sulfamoyl]benzoyl}amino)-4,5,6,7-tetrahydro-1-benzothiophen-3-yl]carbonyl}amino)phenyl]ethyl}benzoate as a pale yellow solid.

Example 34

A mixture of 208 mg of methyl 4-{2-[4-({[2-({3-[cyclopropyl(5-methoxy-5-oxopentyl)sulfamoyl]benzoyl}amino)-4,5,6,7-tetrahydro-1-benzothiophen-3-yl]carbonyl}amino)phenyl]ethyl}benzoate, 1.5 mL of a 1.0 M aqueous sodium hydroxide solution, and 2.1 mL of ethanol was heated and refluxed overnight. The reaction mixture was concentrated under reduced pressure, and then to the obtained residue were added water, 300 mg of citric acid, dichloromethane, and THF in this order, and the organic layer was separated and concentrated under reduced pressure. The obtained residue was purified by silica gel column chromatography (chloroform-methanol). The crude product was washed with diethyl ether to obtain 163 mg of 4-{2-[4-({[2-({3-[(4-carboxybutyl)(cyclopropyl)sulfamoyl]benzoyl}amino)-4,5,6,7-tetrahydro-1-benzothiophen-3-yl]carbonyl}amino)phenyl]ethyl}benzoic acid as a colorless crystal.

Example 35

A mixture of 10.6 mg of 2-amino-N-(4-methoxyphenyl)-4,5,6,7-tetrahydro-1-benzothiophene-3-carboxamide, 10.9 mg of 3-(4-acetyl-piperazine-1-sulfonyl)benzoic acid, 16.0 mg of HATU, 0.012 mL of N,N-diisopropylethylamine, and 1 mL of DMA was stirred at room temperature overnight. The reaction mixture was separated by the addition of chloroform and water, and then the organic layer was concentrated under reduced pressure. The obtained residue was purified by preparative high performance liquid chromatography (methanol-0.1% aqueous formic acid solution) to obtain 5.2 mg of 2-({3-[(4-acetylpiperazin-1-yl)sulfonyl]benzoyl}amino)-N-(4-methoxyphenyl)-4,5,6,7-tetrahydro-1-benzothiophene-3-carboxamide.

Example 36

To a mixture of 9.1 mg of 2-amino-N-[4-(pyridin-4-ylmethyl)phenyl]-4,5,6,7-tetrahydro-1-benzothiophene-3-carboxamide, 8.1 mg of 3-(morpholine-4-sulfonyl)benzoic acid, 0.016 mL of N,N-diisopropylethylamine, and 0.5 mL of DMF was added a mixture of 11.4 mg of HATU and 0.1 mL of DMF, followed by stirring at 60° C. overnight. The reaction mixture was separated by the addition of chloroform and water, and then the organic layer was concentrated under reduced pressure. The obtained residue was purified by preparative high performance liquid chromatography (methanol-0.1% aqueous formic acid solution) to obtain 8.9 mg of 2-{[3-(morpholin-4-ylsulfonyl)benzoyl]amino}-N-[4-(pyridin-4-ylmethyl)phenyl]-4,5,6,7-tetrahydro-1-benzothiophene-3-carboxamide.

In the same manner as in the methods of Examples 1 to 36, the compounds of Examples 37 to 153 were prepared. The structures, the physicochemical data, and the preparation methods of the Example compounds are shown in Tables below.

TABLE 3

| Ex | Structure | Syn |
|----|-----------|-----|
| 1  | 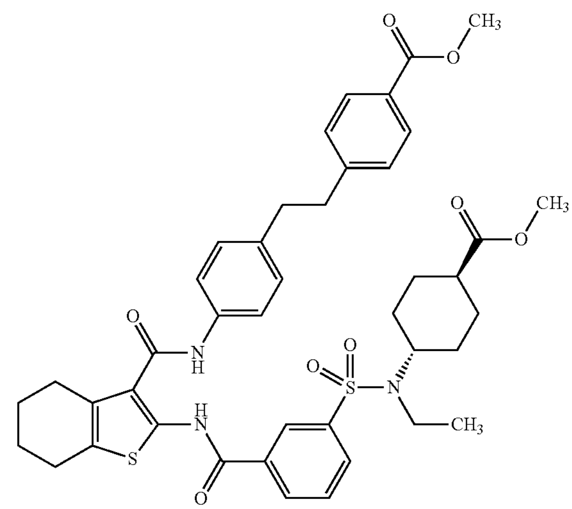 [SMILES: CCN([C@H]1CC[C@H](C(=O)OC)CC1)S(=O)(=O)c1cccc(C(=O)Nc2sc3c(c2C(=O)Nc2ccc(CCc4ccc(C(=O)OC)cc4)cc2)CCCC3)c1]          | 1   |
| 2  | 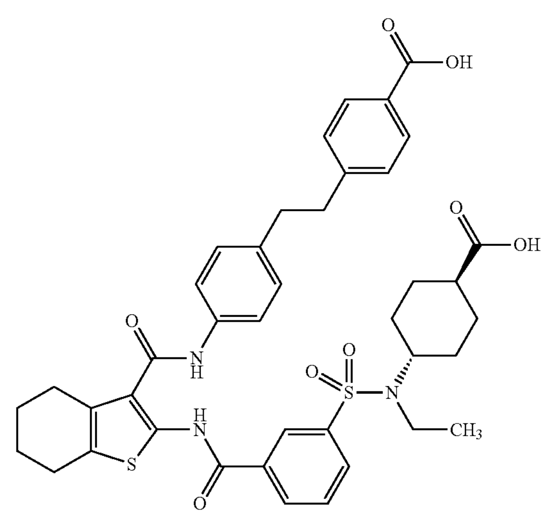 [SMILES: CCN([C@H]1CC[C@H](C(=O)O)CC1)S(=O)(=O)c1cccc(C(=O)Nc2sc3c(c2C(=O)Nc2ccc(CCc4ccc(C(=O)O)cc4)cc2)CCCC3)c1]          | 2   |

TABLE 3-continued
| Ex | Structure | Syn |
|---|---|---|
| 3 | 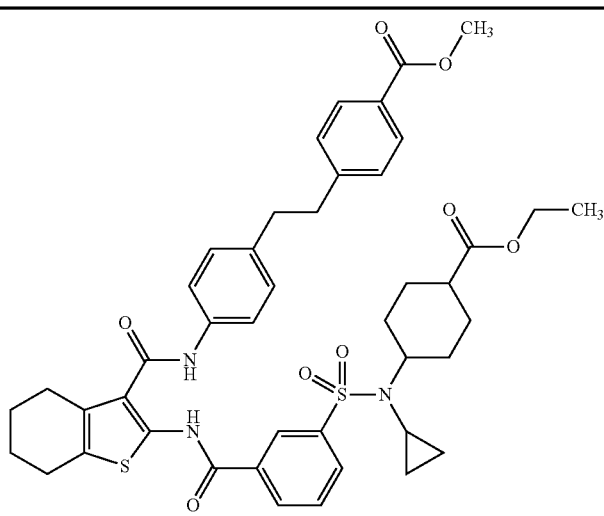 | 3 |
TABLE 4
| Ex | Structure | Syn |
|---|---|---|
| 4 | 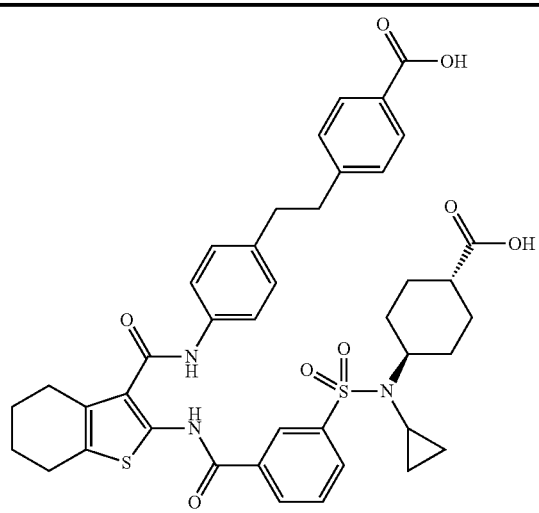 | 4 |
| 5 | 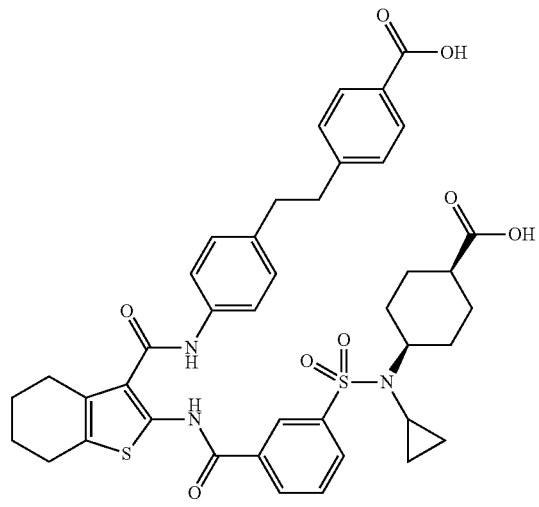 [SMILES: O=C(O)c1ccc(CCc2ccc(NC(=O)c3c(NC(=O)c4cccc(S(=O)(=O)N(C5CC5)[C@H]5CC[C@@H](C(=O)O)CC5)c4)sc4c3CCCC4)cc2)cc1] | 5 |

TABLE 4-continued

| Ex | Structure | Syn |
|---|---|---|
| 6 | 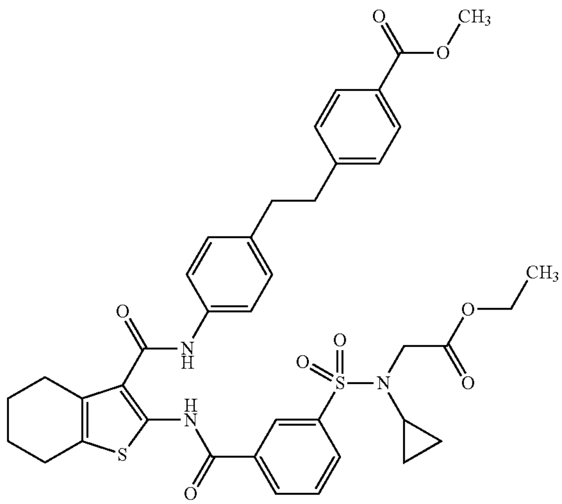 [SMILES: CCOC(=O)CN(C1CC1)S(=O)(=O)c1cccc(C(=O)Nc2sc3c(c2C(=O)Nc2ccc(CCc4ccc(C(=O)OC)cc4)cc2)CCCC3)c1] | 6 |

TABLE 5

| Ex | Structure | Syn |
|---|---|---|
| 7 | 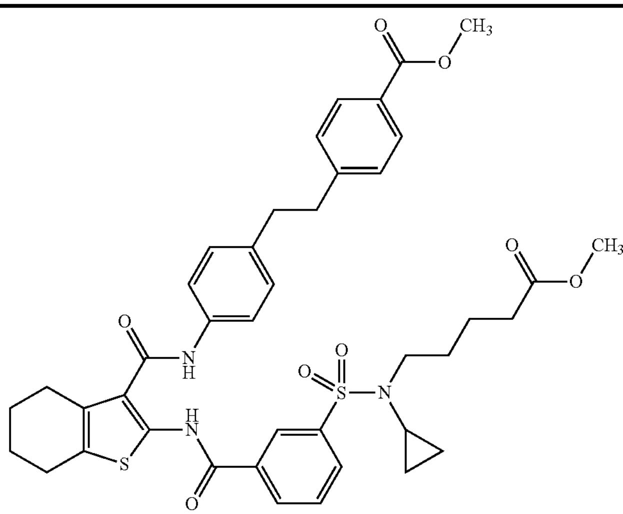 | 7 |
| 8 | 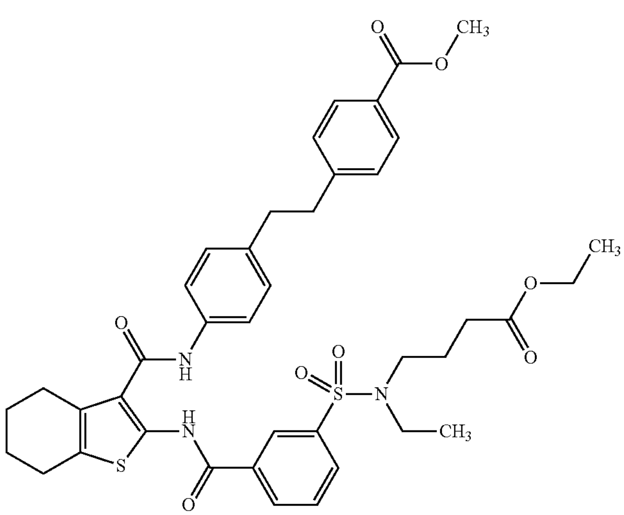 [SMILES: CCOC(=O)CCCN(CC)S(=O)(=O)c1cccc(C(=O)Nc2sc3c(c2C(=O)Nc2ccc(CCc4ccc(C(=O)OC)cc4)cc2)CCCC3)c1] | 8 |

TABLE 5-continued

| Ex | Structure | Syn |
|----|-----------|-----|
| 9  | 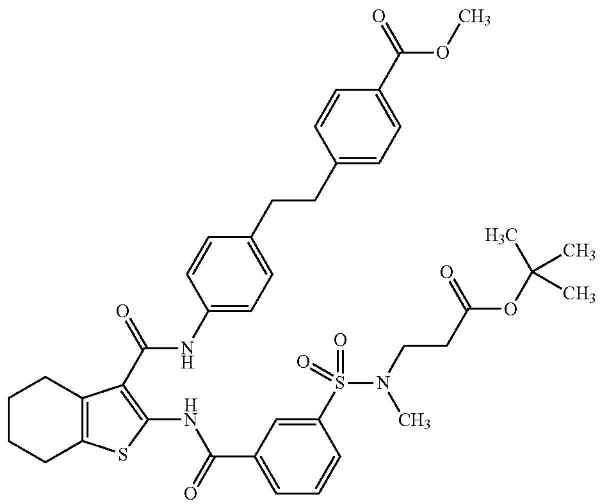 [SMILES: COC(=O)c1ccc(CCc2ccc(NC(=O)c3c(NC(=O)c4cccc(S(=O)(=O)N(C)CCC(=O)OC(C)(C)C)c4)sc4c3CCCC4)cc2)cc1]          | 9   |

TABLE 6

| Ex | Structure | Syn |
|----|-----------|-----|
| 10 | 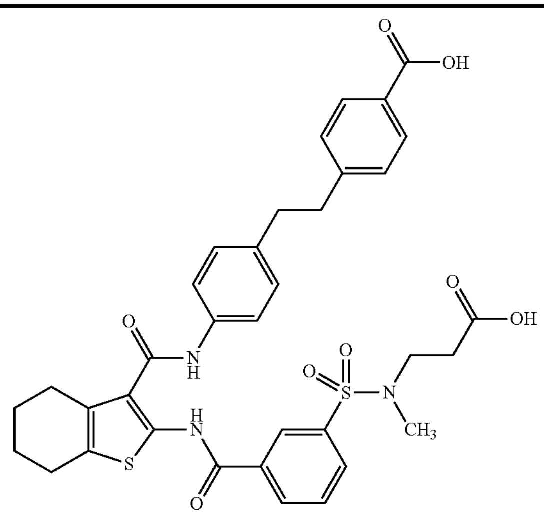          | 10  |
| 11 | 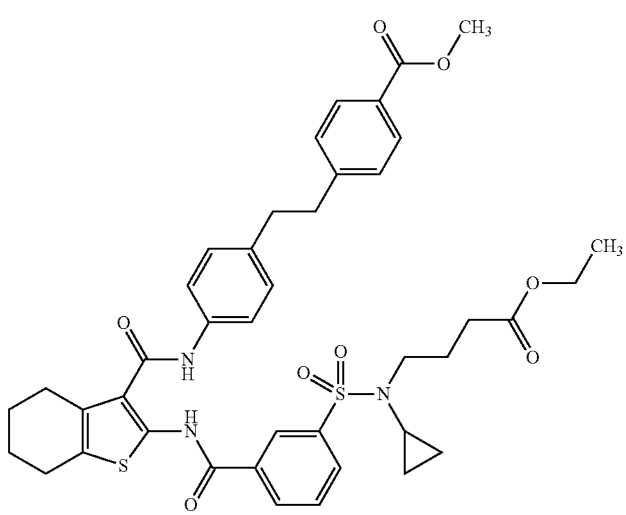 [SMILES: CCOC(=O)CCCN(C1CC1)S(=O)(=O)c1cccc(C(=O)Nc2sc3c(c2C(=O)Nc2ccc(CCc4ccc(C(=O)OC)cc4)cc2)CCCC3)c1]          | 11  |

TABLE 6-continued

| Ex | Structure | Syn |
|----|-----------|-----|
| 12 | 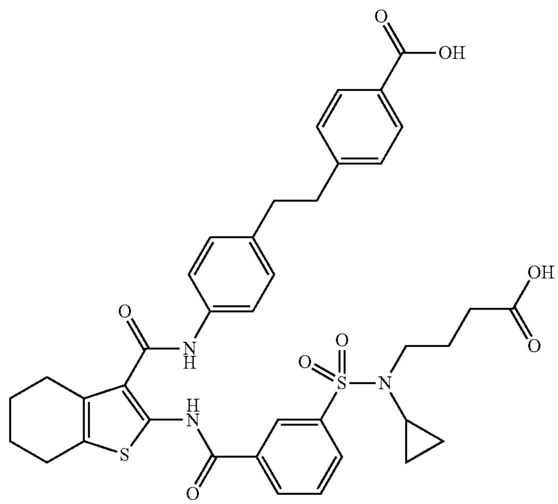 [SMILES: O=C(O)CCCN(C1CC1)S(=O)(=O)c1cccc(C(=O)Nc2sc3c(c2C(=O)Nc2ccc(CCc4ccc(C(=O)O)cc4)cc2)CCCC3)c1] | 12 |

TABLE 7

| Ex | Structure | Syn |
|----|-----------|-----|
| 13 | 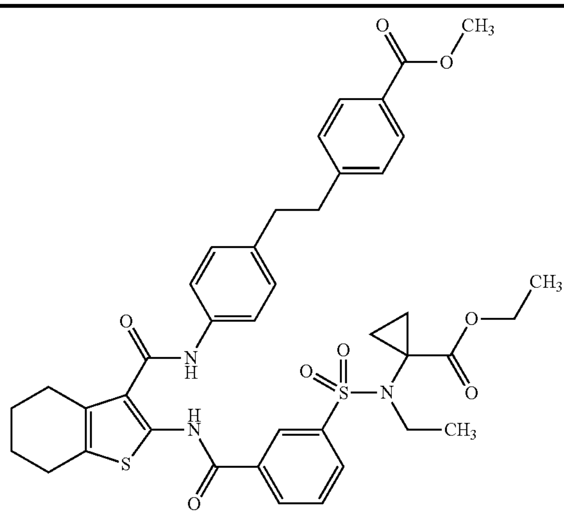 | 13 |
| 14 | 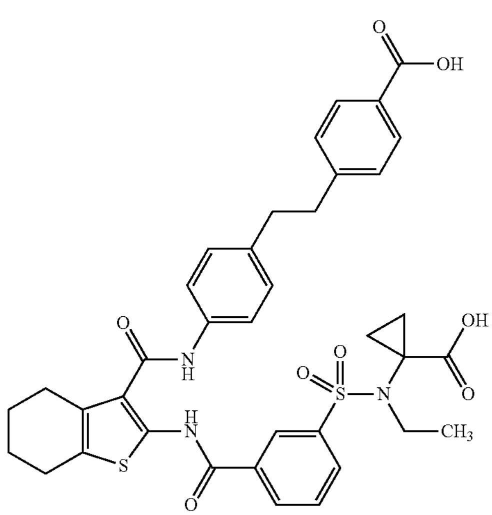 [SMILES: CCN(C1(C(=O)O)CC1)S(=O)(=O)c1cccc(C(=O)Nc2sc3c(c2C(=O)Nc2ccc(CCc4ccc(C(=O)O)cc4)cc2)CCCC3)c1] | 14 |

TABLE 7-continued

| Ex | Structure | Syn |
|---|---|---|
| 15 | 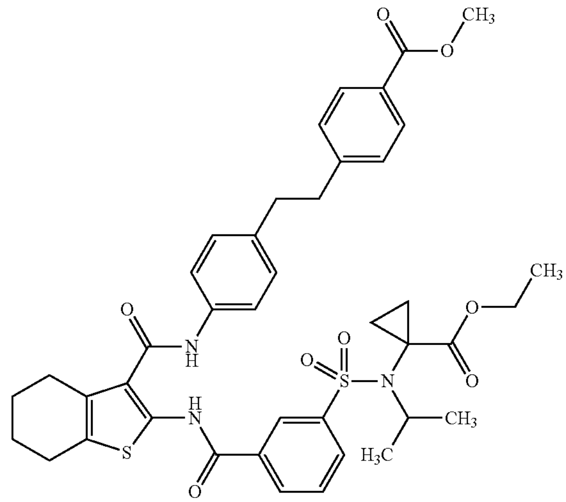 [SMILES: CCOC(=O)C1(N(C(C)C)S(=O)(=O)c2cccc(C(=O)Nc3sc4c(c3C(=O)Nc3ccc(CCc5ccc(C(=O)OC)cc5)cc3)CCCC4)c2)CC1] | 15 |

TABLE 8

| Ex | Structure | Syn |
|---|---|---|
| 16 | 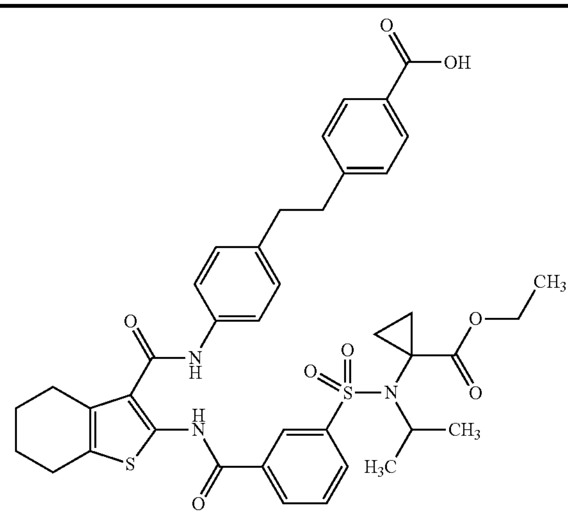 | 16 |
| 17 | 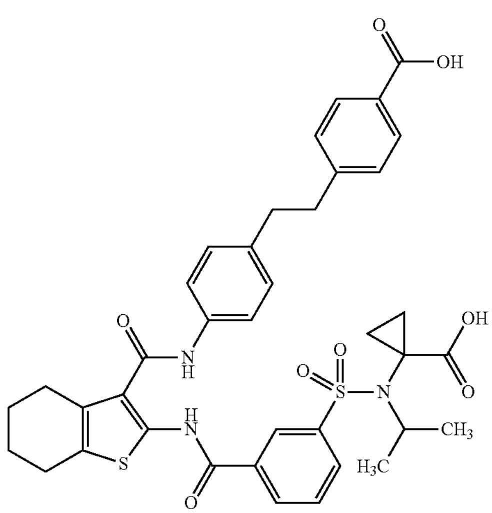 [SMILES: CC(C)N(C1(C(=O)O)CC1)S(=O)(=O)c1cccc(C(=O)Nc2sc3c(c2C(=O)Nc2ccc(CCc4ccc(C(=O)O)cc4)cc2)CCCC3)c1] | 17 |

TABLE 8-continued
| Ex | Structure | Syn |
|----|-----------|-----|
| 18 | 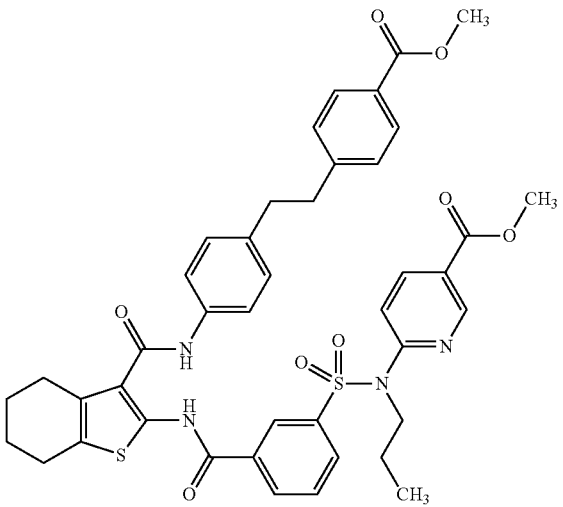 [SMILES: CCCN(c1ccc(C(=O)OC)cn1)S(=O)(=O)c1cccc(C(=O)Nc2sc3c(c2C(=O)Nc2ccc(CCc4ccc(C(=O)OC)cc4)cc2)CCCC3)c1] | 18 |
TABLE 9
| Ex | Structure | Syn |
|----|-----------|-----|
| 19 | 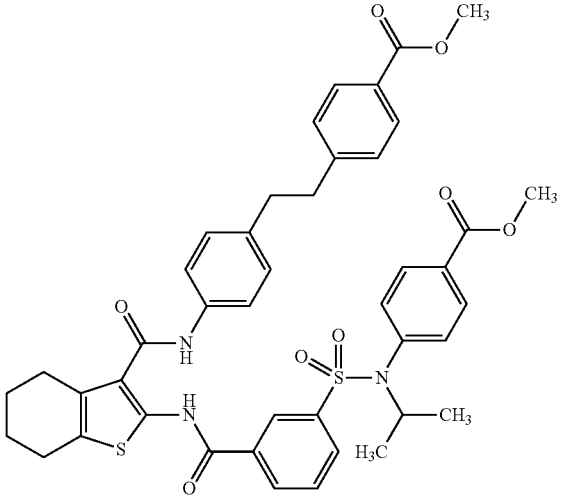 [SMILES: COC(=O)c1ccc(CCc2ccc(NC(=O)c3c(NC(=O)c4cccc(S(=O)(=O)N(c5ccc(C(=O)OC)cc5)C(C)C)c4)sc4c3CCCC4)cc2)cc1] | 19 |
| 20 | 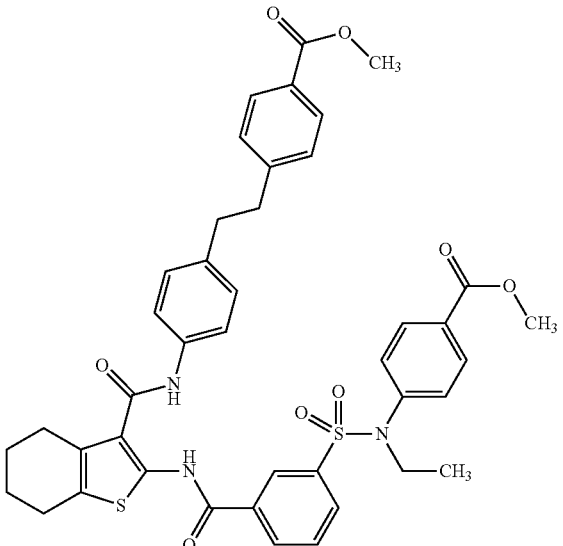 | 20 |

TABLE 10
| Ex | Structure | Syn |
|---|---|---|
| 21 | 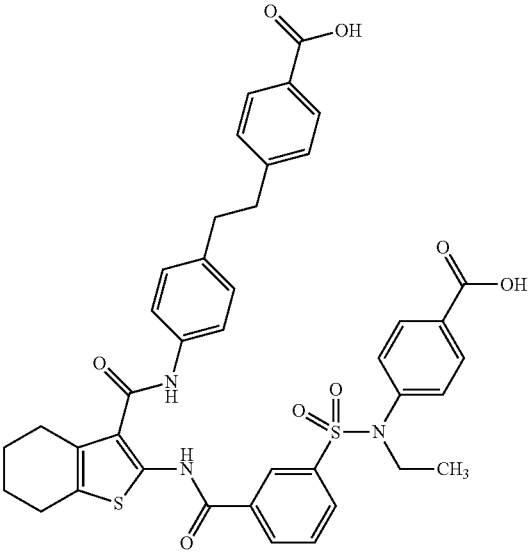 [SMILES: CCN(c1ccc(C(=O)O)cc1)S(=O)(=O)c1cccc(C(=O)Nc2sc3c(c2C(=O)Nc2ccc(CCc4ccc(C(=O)O)cc4)cc2)CCCC3)c1] | 21 |
| 22 | 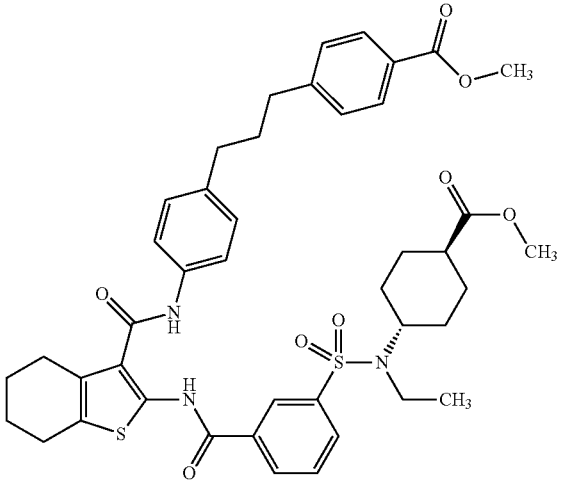 [SMILES: CCN([C@H]1CC[C@H](C(=O)OC)CC1)S(=O)(=O)c1cccc(C(=O)Nc2sc3c(c2C(=O)Nc2ccc(CCCc4ccc(C(=O)OC)cc4)cc2)CCCC3)c1] | 22 |
| 23 | 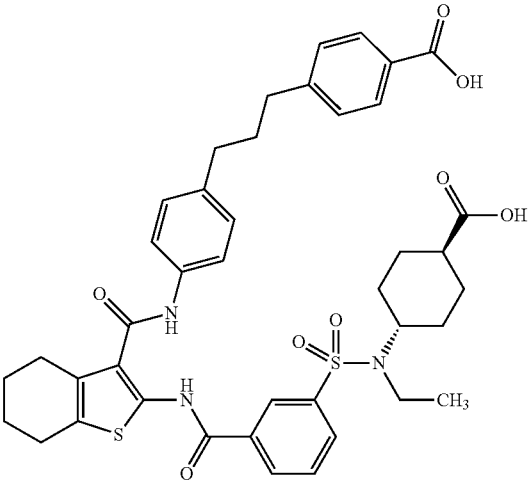 [SMILES: CCN([C@H]1CC[C@H](C(=O)O)CC1)S(=O)(=O)c1cccc(C(=O)Nc2sc3c(c2C(=O)Nc2ccc(CCCc4ccc(C(=O)O)cc4)cc2)CCCC3)c1] | 23 |

TABLE 11
| Ex | Structure | Syn |
|----|-----------|-----|
| 24 | 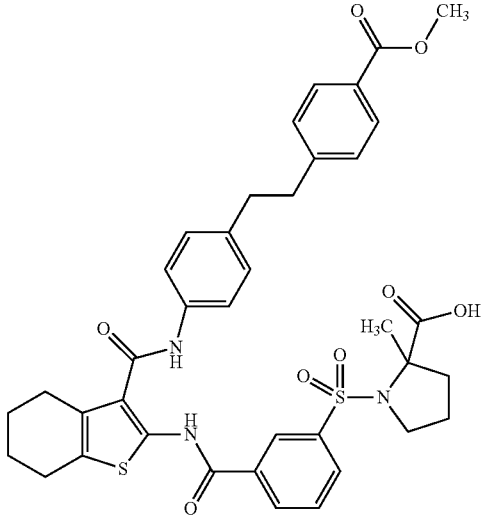 [SMILES: COC(=O)c1ccc(CCc2ccc(NC(=O)c3c(NC(=O)c4cccc(S(=O)(=O)N5CCCC5(C)C(=O)O)c4)sc4c3CCCC4)cc2)cc1] | 24 |
| 25 | 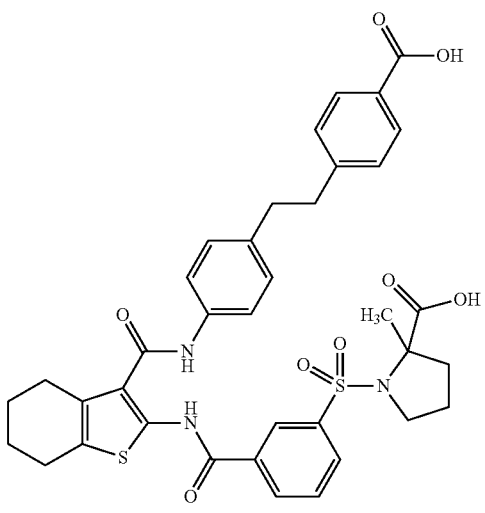 [SMILES: CC1(C(=O)O)CCCN1S(=O)(=O)c1cccc(C(=O)Nc2sc3c(c2C(=O)Nc2ccc(CCc4ccc(C(=O)O)cc4)cc2)CCCC3)c1] | 25 |
| 26 | 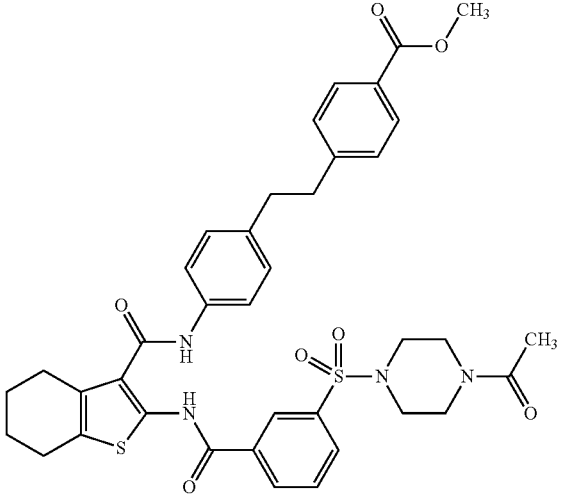 [SMILES: COC(=O)c1ccc(CCc2ccc(NC(=O)c3c(NC(=O)c4cccc(S(=O)(=O)N5CCN(C(C)=O)CC5)c4)sc4c3CCCC4)cc2)cc1] | 26 |

TABLE 12

| Ex | Structure | Syn |
|---|---|---|
| 27 | 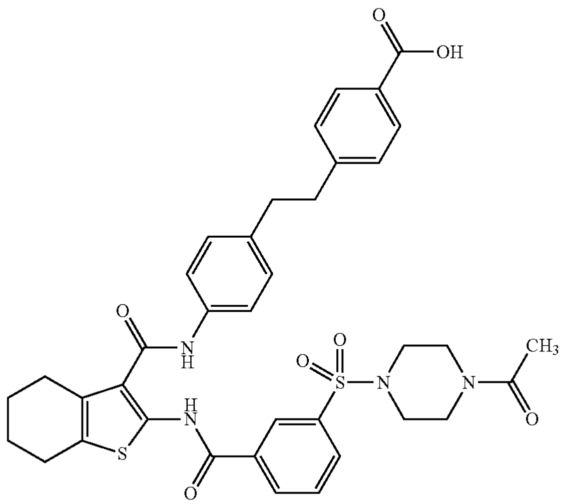 [SMILES: CC(=O)N1CCN(S(=O)(=O)c2cccc(C(=O)Nc3sc4c(c3C(=O)Nc3ccc(CCc5ccc(C(=O)O)cc5)cc3)CCCC4)c2)CC1] | 27 |
| 28 | 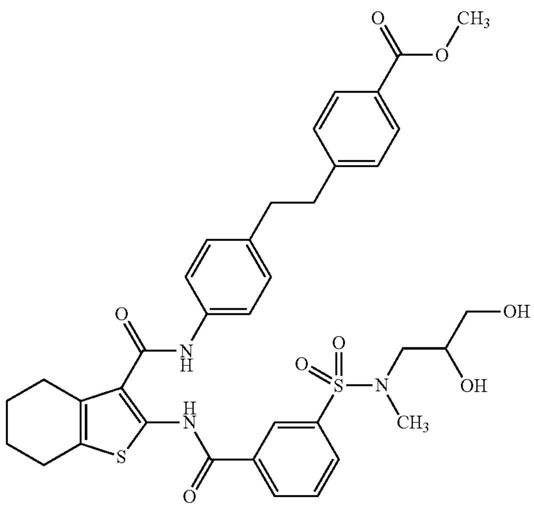 [SMILES: COC(=O)c1ccc(CCc2ccc(NC(=O)c3c(NC(=O)c4cccc(S(=O)(=O)N(C)CC(O)CO)c4)sc4c3CCCC4)cc2)cc1] | 28 |
| 29 | 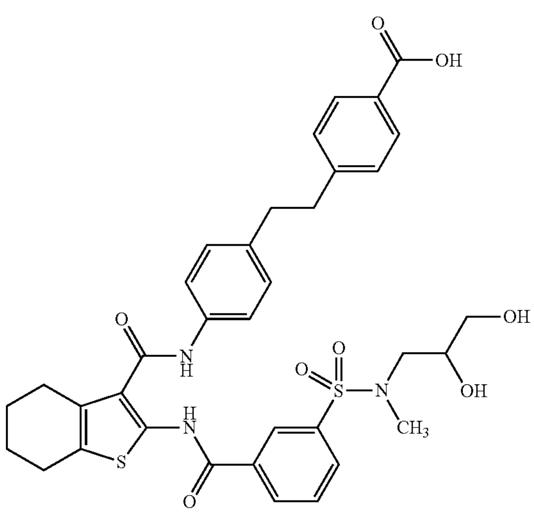 [SMILES: CN(CC(O)CO)S(=O)(=O)c1cccc(C(=O)Nc2sc3c(c2C(=O)Nc2ccc(CCc4ccc(C(=O)O)cc4)cc2)CCCC3)c1] | 29 |

TABLE 13
| Ex | Structure | Syn |
|---|---|---|
| 30 | 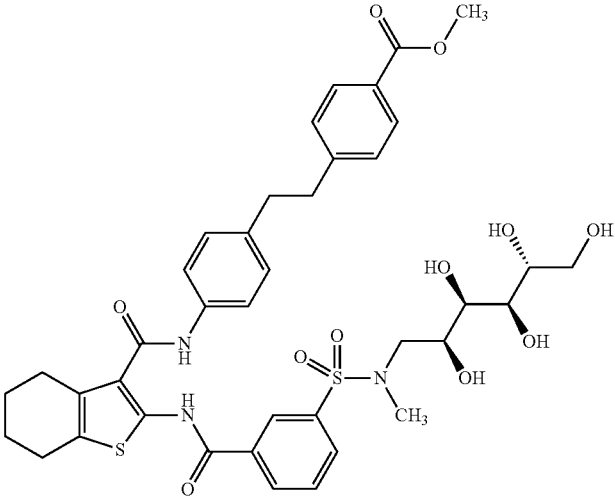 [SMILES: COC(=O)c1ccc(CCc2ccc(NC(=O)c3c(NC(=O)c4cccc(S(=O)(=O)N(C)C[C@H](O)[C@@H](O)[C@H](O)[C@H](O)CO)c4)sc4c3CCCC4)cc2)cc1] | 30 |
| 31 | 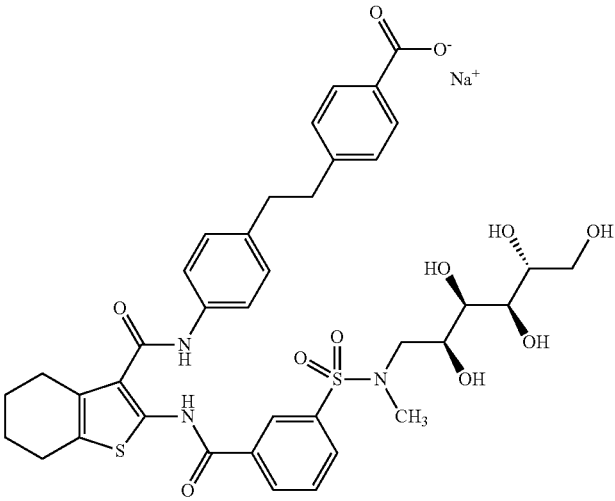 [SMILES: CN(C[C@H](O)[C@@H](O)[C@H](O)[C@H](O)CO)S(=O)(=O)c1cccc(C(=O)Nc2sc3c(c2C(=O)Nc2ccc(CCc4ccc(C(=O)[O-])cc4)cc2)CCCC3)c1 ; [Na+]] | 31 |
| 32 | 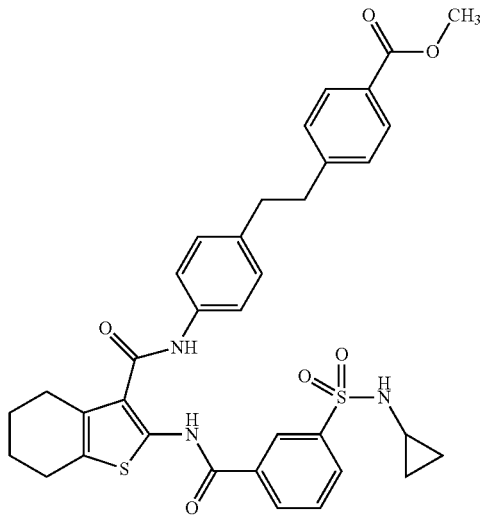 [SMILES: COC(=O)c1ccc(CCc2ccc(NC(=O)c3c(NC(=O)c4cccc(S(=O)(=O)NC5CC5)c4)sc4c3CCCC4)cc2)cc1] | 32 |

TABLE 14
| Ex | Structure | Syn |
|---|---|---|
| 33 | 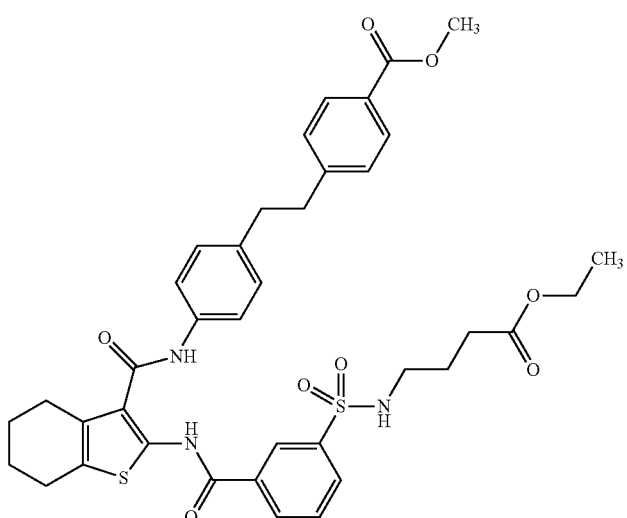 | 33 |
| 34 | 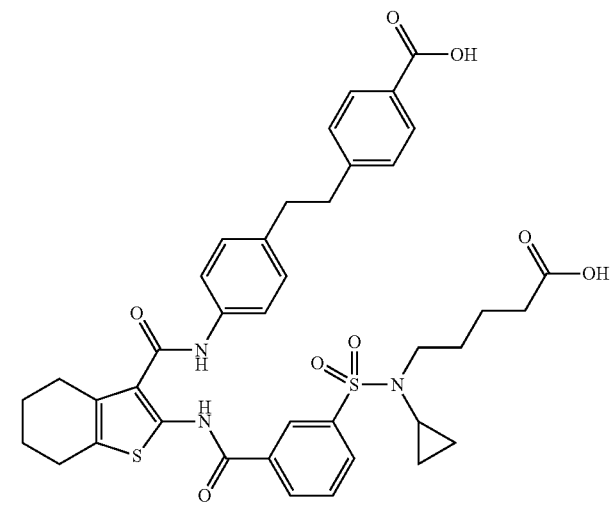 [SMILES: O=C(O)CCCCN(C1CC1)S(=O)(=O)c1cccc(C(=O)Nc2sc3c(c2C(=O)Nc2ccc(CCc4ccc(C(=O)O)cc4)cc2)CCCC3)c1] | 34 |
| 35 | 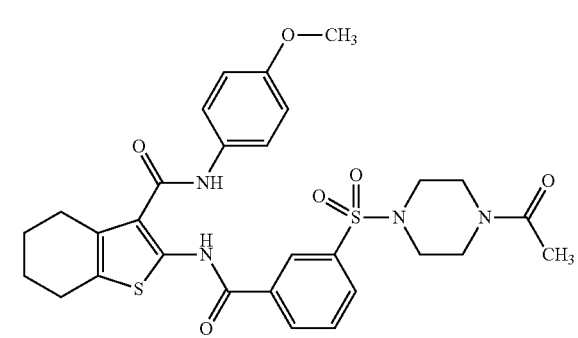 [SMILES: COc1ccc(NC(=O)c2c(NC(=O)c3cccc(S(=O)(=O)N4CCN(C(C)=O)CC4)c3)sc3c2CCCC3)cc1] | 35 |

TABLE 15

| Ex | Structure | Syn |
|----|-----------|-----|
| 36 | 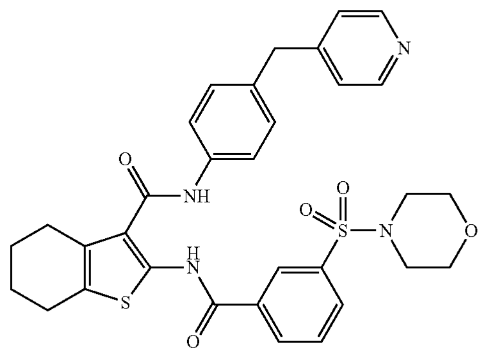 [SMILES: O=C(Nc1sc2c(c1C(=O)Nc1ccc(Cc3ccncc3)cc1)CCCC2)c1cccc(S(=O)(=O)N2CCOCC2)c1] | 36 |
| 37 | 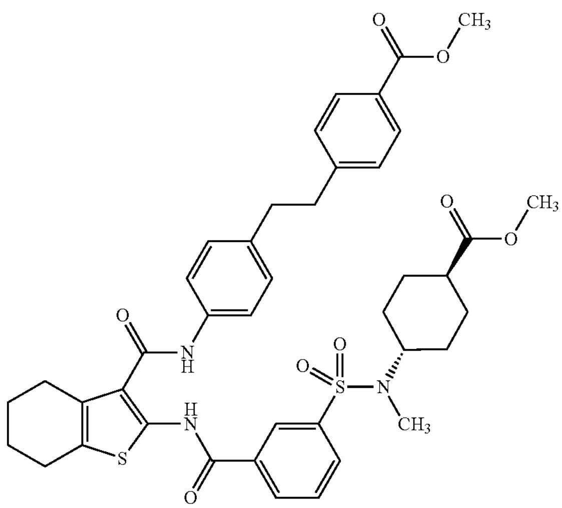 [SMILES: COC(=O)c1ccc(CCc2ccc(NC(=O)c3c(NC(=O)c4cccc(S(=O)(=O)N(C)[C@H]5CC[C@H](C(=O)OC)CC5)c4)sc4c3CCCC4)cc2)cc1] | 1 |
| 38 | 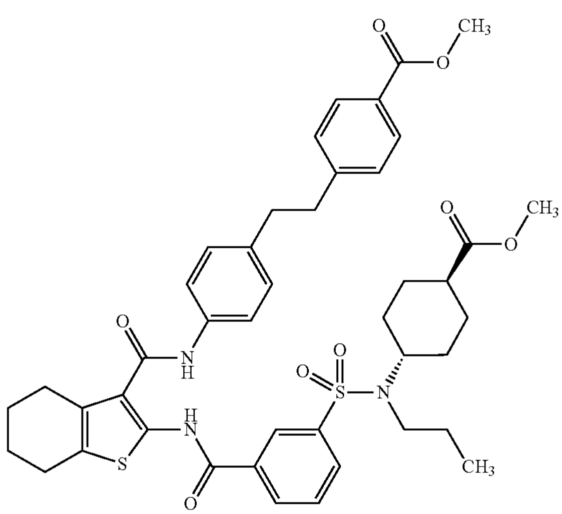 [SMILES: CCCN([C@H]1CC[C@H](C(=O)OC)CC1)S(=O)(=O)c1cccc(C(=O)Nc2sc3c(c2C(=O)Nc2ccc(CCc4ccc(C(=O)OC)cc4)cc2)CCCC3)c1] | 1 |

TABLE 16
| Ex | Structure | Syn |
|---|---|---|
| 39 | 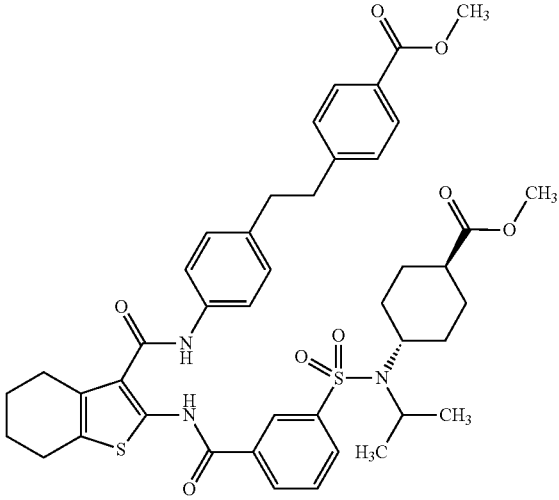 [SMILES: COC(=O)c1ccc(CCc2ccc(NC(=O)c3c(NC(=O)c4cccc(S(=O)(=O)N(C(C)C)[C@H]5CC[C@H](C(=O)OC)CC5)c4)sc4c3CCCC4)cc2)cc1] | 1 |
| 40 | 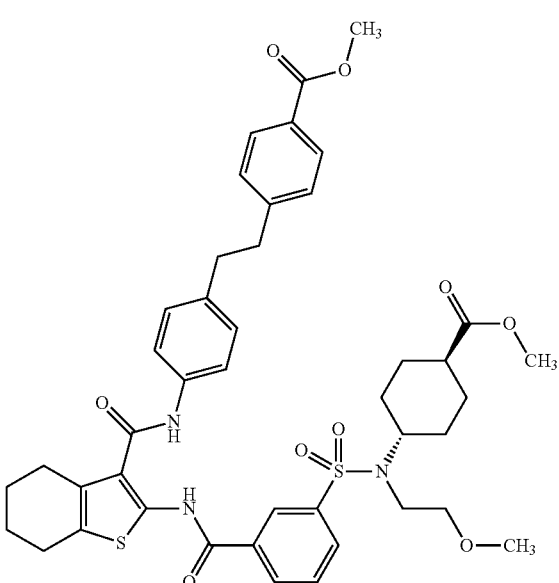 | 1 |

TABLE 17

| Ex | Structure | Syn |
|----|-----------|-----|
| 41 | 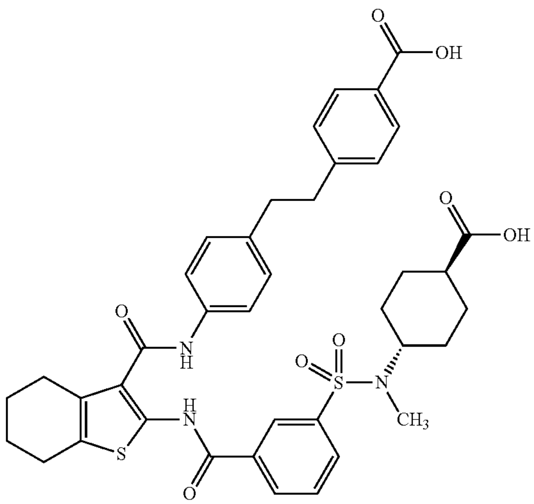 [SMILES: CN([C@H]1CC[C@H](C(=O)O)CC1)S(=O)(=O)c1cccc(C(=O)Nc2sc3c(c2C(=O)Nc2ccc(CCc4ccc(C(=O)O)cc4)cc2)CCCC3)c1] | 2 |
| 42 | 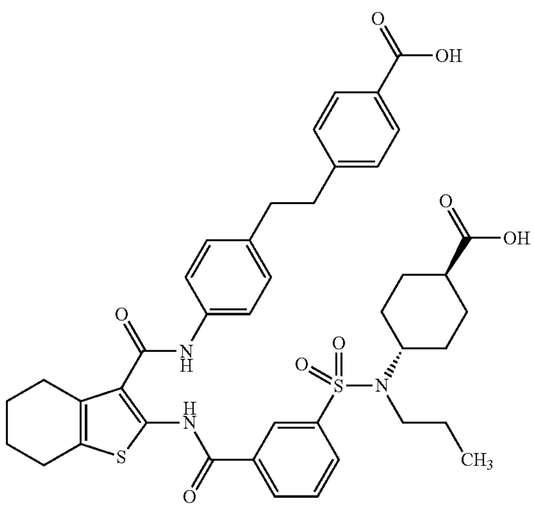 [SMILES: CCCN([C@H]1CC[C@H](C(=O)O)CC1)S(=O)(=O)c1cccc(C(=O)Nc2sc3c(c2C(=O)Nc2ccc(CCc4ccc(C(=O)O)cc4)cc2)CCCC3)c1] | 2 |
| 43 | 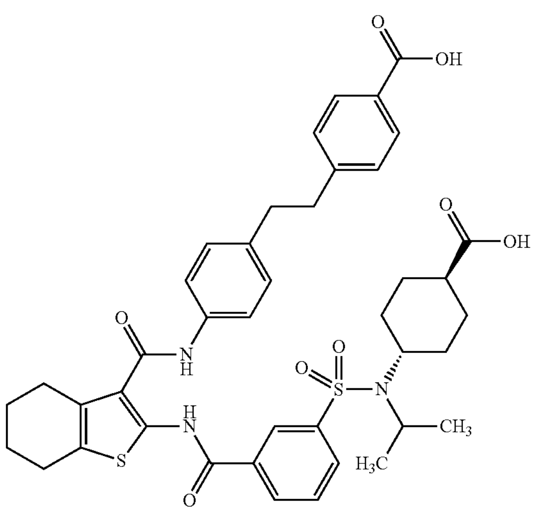 [SMILES: CC(C)N([C@H]1CC[C@H](C(=O)O)CC1)S(=O)(=O)c1cccc(C(=O)Nc2sc3c(c2C(=O)Nc2ccc(CCc4ccc(C(=O)O)cc4)cc2)CCCC3)c1] | 2 |

TABLE 18

| Ex | Structure | Syn |
|---|---|---|
| 44 | 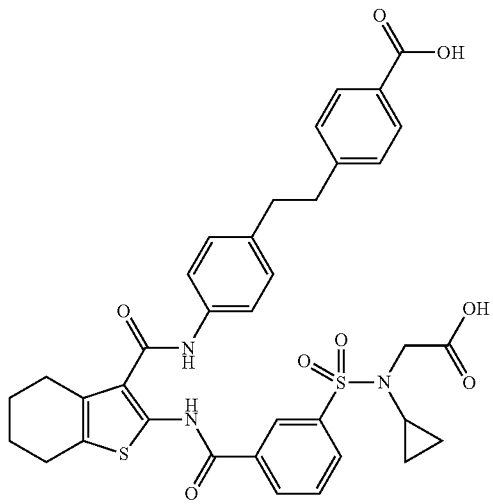 [SMILES: O=C(O)CN(C1CC1)S(=O)(=O)c1cccc(C(=O)Nc2sc3c(c2C(=O)Nc2ccc(CCc4ccc(C(=O)O)cc4)cc2)CCCC3)c1] | 2 |
| 45 | 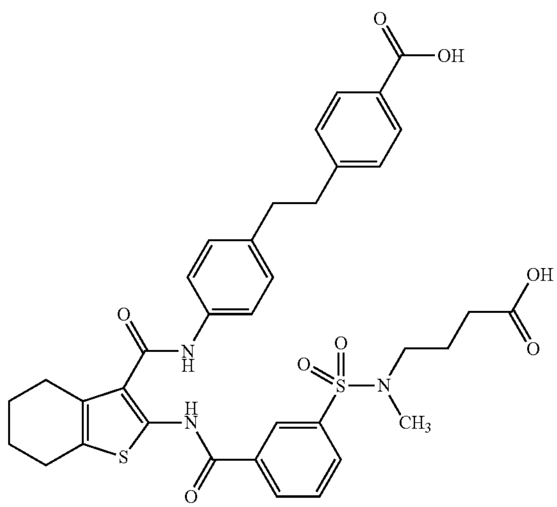 [SMILES: CN(CCCC(=O)O)S(=O)(=O)c1cccc(C(=O)Nc2sc3c(c2C(=O)Nc2ccc(CCc4ccc(C(=O)O)cc4)cc2)CCCC3)c1] | 2 |
| 46 | 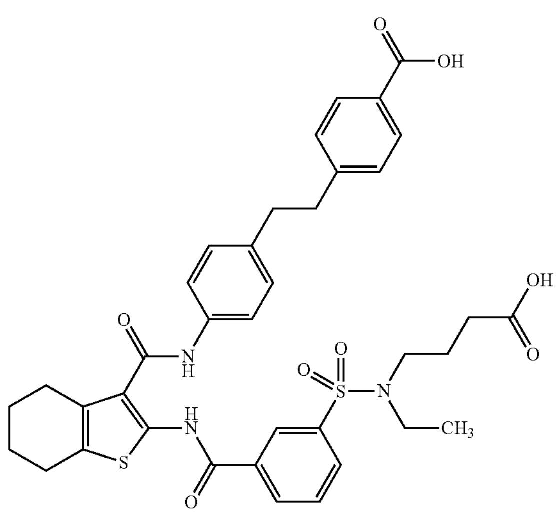 [SMILES: CCN(CCCC(=O)O)S(=O)(=O)c1cccc(C(=O)Nc2sc3c(c2C(=O)Nc2ccc(CCc4ccc(C(=O)O)cc4)cc2)CCCC3)c1] | 2 |

TABLE 19

| Ex | Structure | Syn |
|---|---|---|
| 47 | 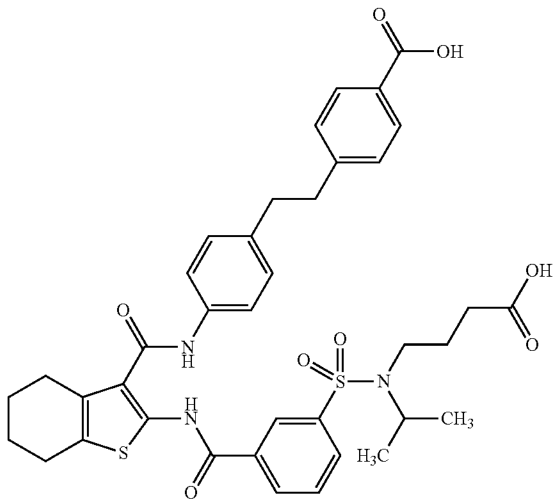 [SMILES: CC(C)N(CCCC(=O)O)S(=O)(=O)c1cccc(C(=O)Nc2sc3c(c2C(=O)Nc2ccc(CCc4ccc(C(=O)O)cc4)cc2)CCCC3)c1] | 2 |
| 48 | 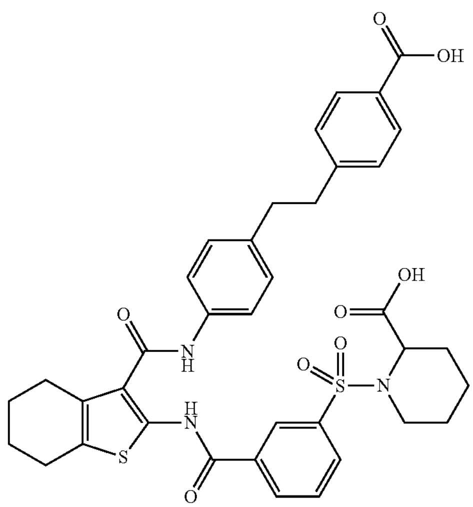 [SMILES: O=C(O)c1ccc(CCc2ccc(NC(=O)c3c(NC(=O)c4cccc(S(=O)(=O)N5CCCCC5C(=O)O)c4)sc4c3CCCC4)cc2)cc1] | 2 |
| 49 | 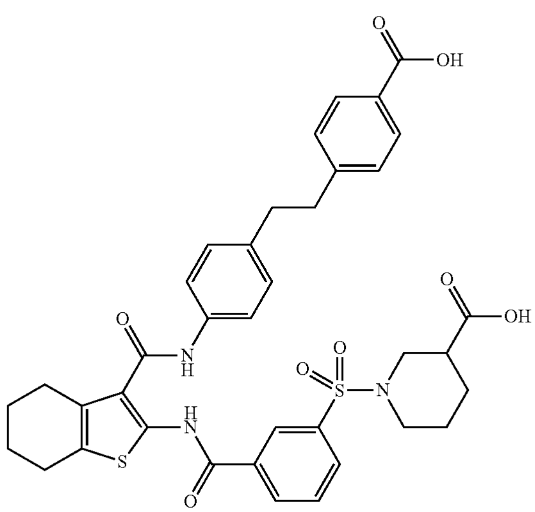 [SMILES: O=C(O)c1ccc(CCc2ccc(NC(=O)c3c(NC(=O)c4cccc(S(=O)(=O)N5CCCC(C(=O)O)C5)c4)sc4c3CCCC4)cc2)cc1] | 2 |

TABLE 20
| Ex | Structure | Syn |
|---|---|---|
| 50 | 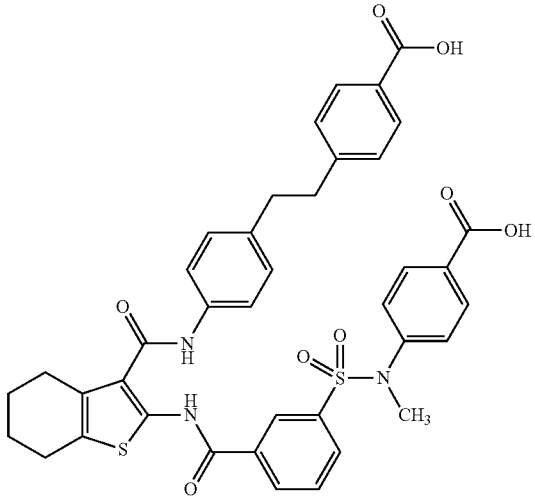 [SMILES: CN(c1ccc(C(=O)O)cc1)S(=O)(=O)c1cccc(C(=O)Nc2sc3c(c2C(=O)Nc2ccc(CCc4ccc(C(=O)O)cc4)cc2)CCCC3)c1] | 2 |
| 51 | 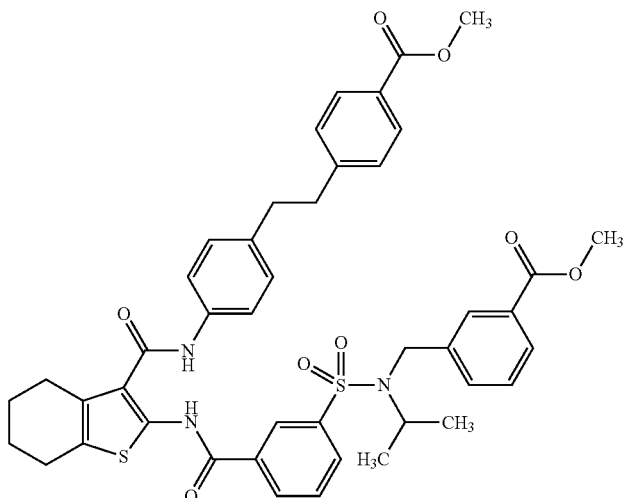 | 3 |
| 52 | 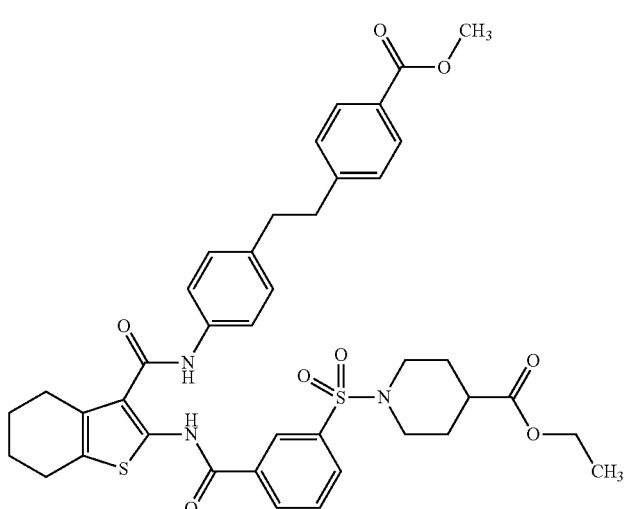 | 3 |

TABLE 21

| Ex | Structure | Syn |
|----|-----------|-----|
| 53 | 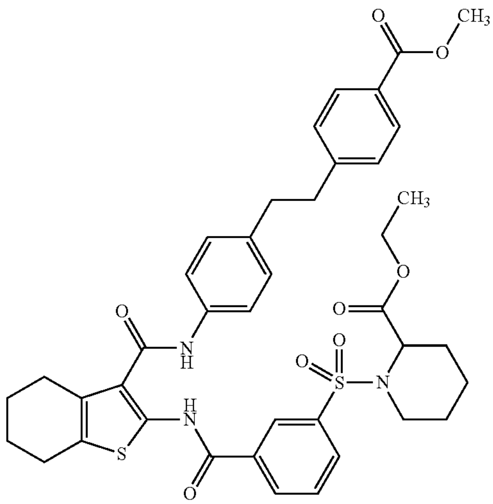 [SMILES: CCOC(=O)C1CCCCN1S(=O)(=O)c1cccc(C(=O)Nc2sc3c(c2C(=O)Nc2ccc(CCc4ccc(C(=O)OC)cc4)cc2)CCCC3)c1] | 3 |
| 54 | 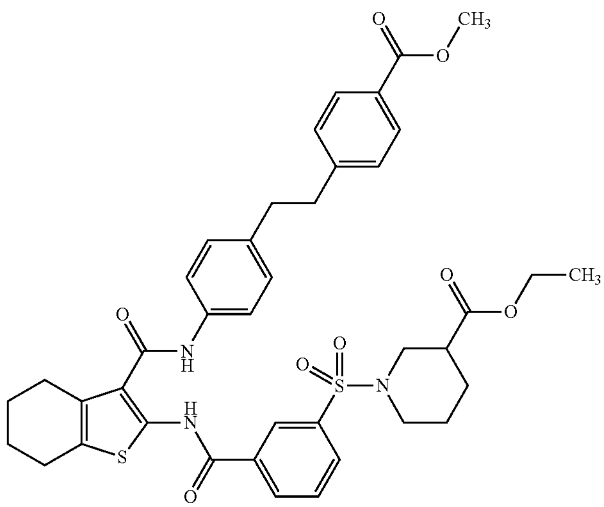 [SMILES: CCOC(=O)C1CCCN(S(=O)(=O)c2cccc(C(=O)Nc3sc4c(c3C(=O)Nc3ccc(CCc5ccc(C(=O)OC)cc5)cc3)CCCC4)c2)C1] | 3 |
| 55 | 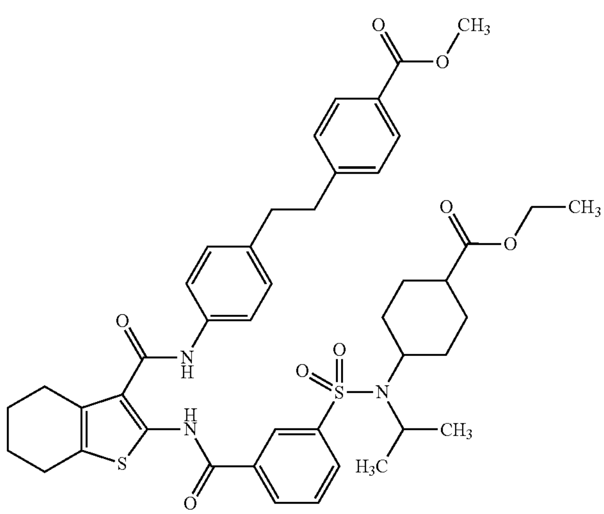 [SMILES: CCOC(=O)C1CCC(N(C(C)C)S(=O)(=O)c2cccc(C(=O)Nc3sc4c(c3C(=O)Nc3ccc(CCc5ccc(C(=O)OC)cc5)cc3)CCCC4)c2)CC1] | 3 |

TABLE 22

| Ex | Structure | Syn |
|----|-----------|-----|
| 56 | (structure) | 3 |
| 57 | (structure) | 3 |

TABLE 23
| Ex | Structure | Syn |
|---|---|---|
| 58 | 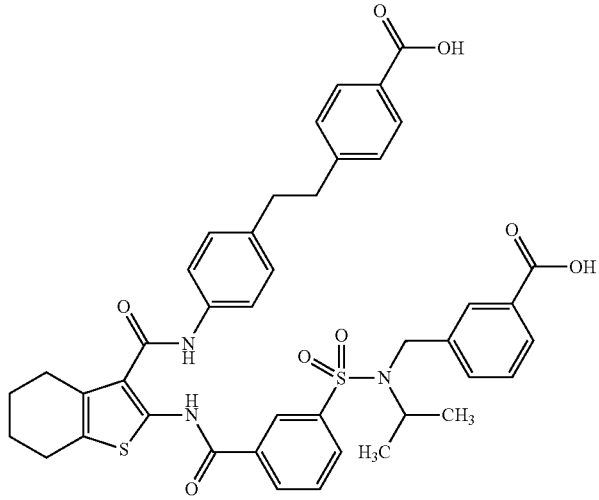 [SMILES: CC(C)N(Cc1cccc(C(=O)O)c1)S(=O)(=O)c1cccc(C(=O)Nc2sc3c(c2C(=O)Nc2ccc(CCc4ccc(C(=O)O)cc4)cc2)CCCC3)c1] | 4 |
| 59 | 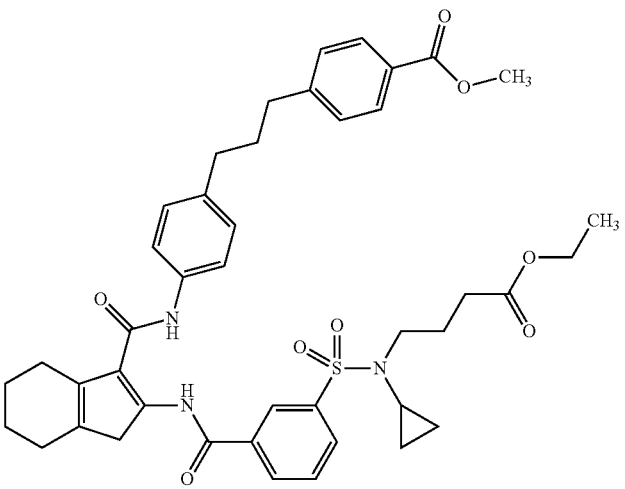 [SMILES: CCOC(=O)CCCN(C1CC1)S(=O)(=O)c1cccc(C(=O)NC2=C(C(=O)Nc3ccc(CCCc4ccc(C(=O)OC)cc4)cc3)C3=C(CCCC3)C2)c1] | 6 |
| 60 | 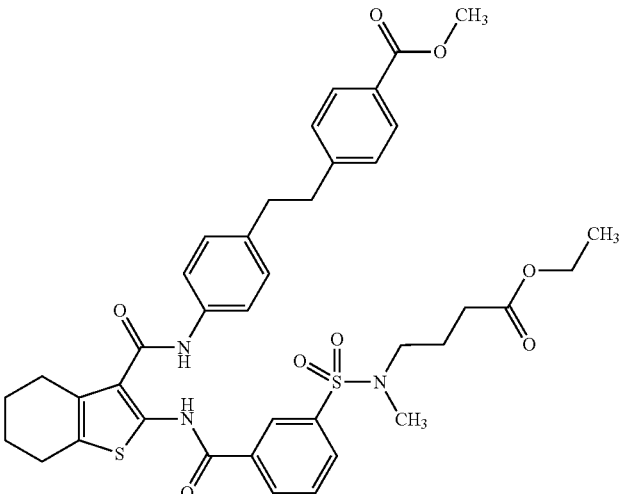 | 8 |

TABLE 24

| Ex | Structure | Syn |
|---|---|---|
| 61 | (structure) | 9 |
| 62 | (structure) | 10 |
| 63 | (structure) | 11 |

TABLE 25

| Ex | Structure | Syn |
|---|---|---|
| 64 | 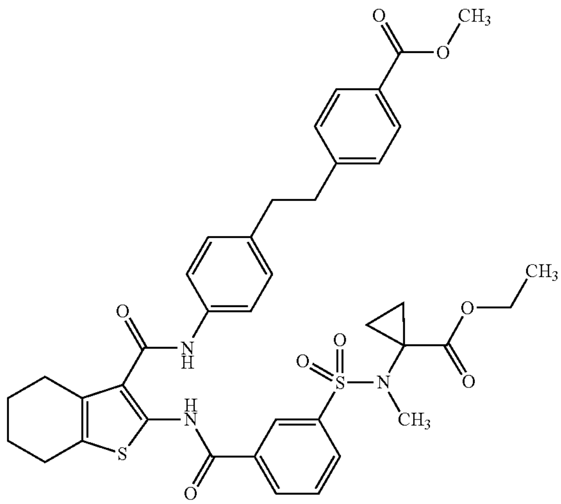 [SMILES: CCOC(=O)C1(N(C)S(=O)(=O)c2cccc(C(=O)Nc3sc4c(c3C(=O)Nc3ccc(CCc5ccc(C(=O)OC)cc5)cc3)CCCC4)c2)CC1] | 13 |
| 65 | 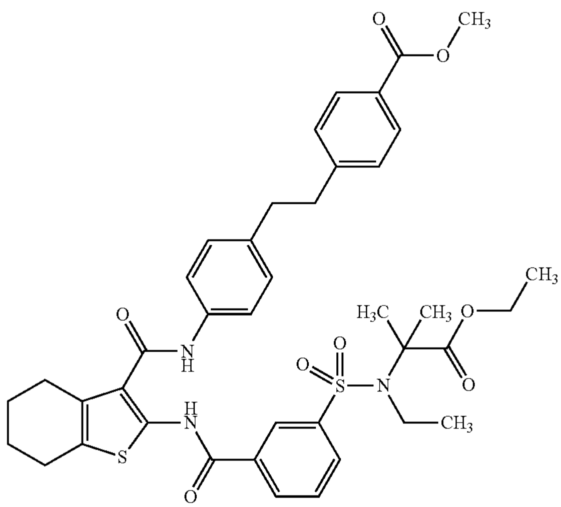 [SMILES: CCOC(=O)C(C)(C)N(CC)S(=O)(=O)c1cccc(C(=O)Nc2sc3c(c2C(=O)Nc2ccc(CCc4ccc(C(=O)OC)cc4)cc2)CCCC3)c1] | 13 |
| 66 | 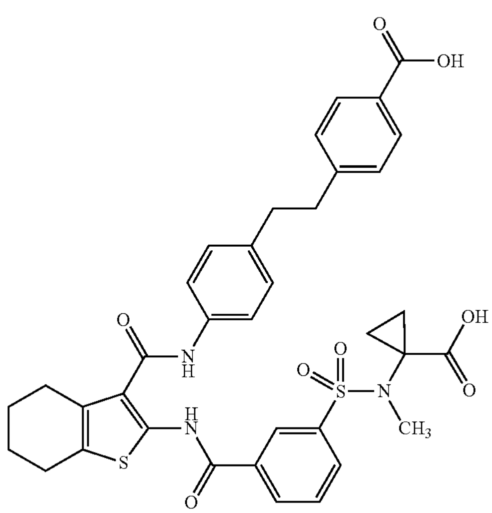 [SMILES: CN(C1(C(=O)O)CC1)S(=O)(=O)c1cccc(C(=O)Nc2sc3c(c2C(=O)Nc2ccc(CCc4ccc(C(=O)O)cc4)cc2)CCCC3)c1] | 14 |

TABLE 26

| Ex | Structure | Syn |
|---|---|---|
| 67 | 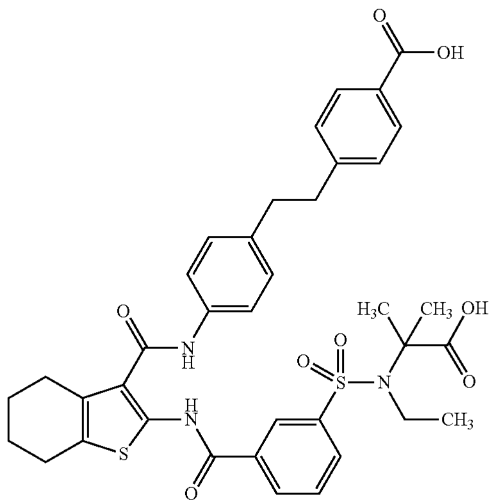 [SMILES: CCN(C(C)(C)C(=O)O)S(=O)(=O)c1cccc(C(=O)Nc2sc3c(c2C(=O)Nc2ccc(CCc4ccc(C(=O)O)cc4)cc2)CCCC3)c1] | 14 |
| 68 | 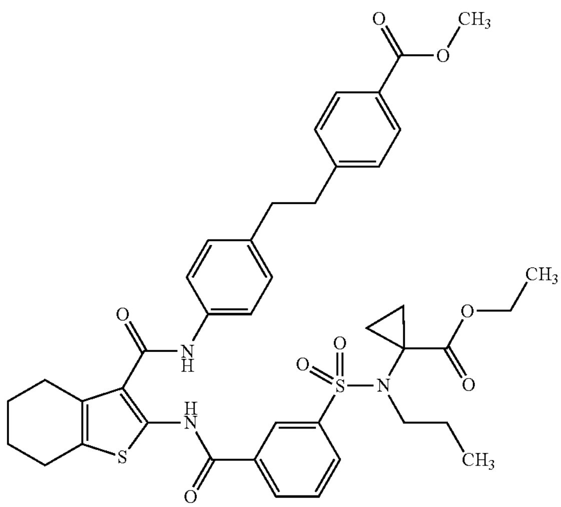 [SMILES: CCCN(C1(C(=O)OCC)CC1)S(=O)(=O)c1cccc(C(=O)Nc2sc3c(c2C(=O)Nc2ccc(CCc4ccc(C(=O)OC)cc4)cc2)CCCC3)c1] | 15 |
| 69 | 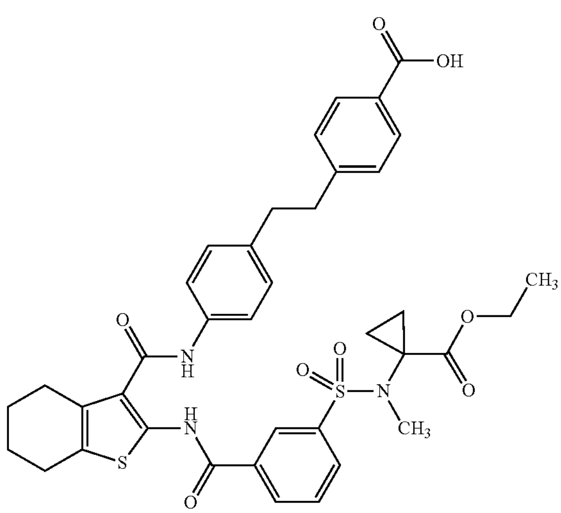 [SMILES: CCOC(=O)C1(N(C)S(=O)(=O)c2cccc(C(=O)Nc3sc4c(c3C(=O)Nc3ccc(CCc5ccc(C(=O)O)cc5)cc3)CCCC4)c2)CC1] | 16 |

TABLE 27

| Ex | Structure | Syn |
|---|---|---|
| 70 | 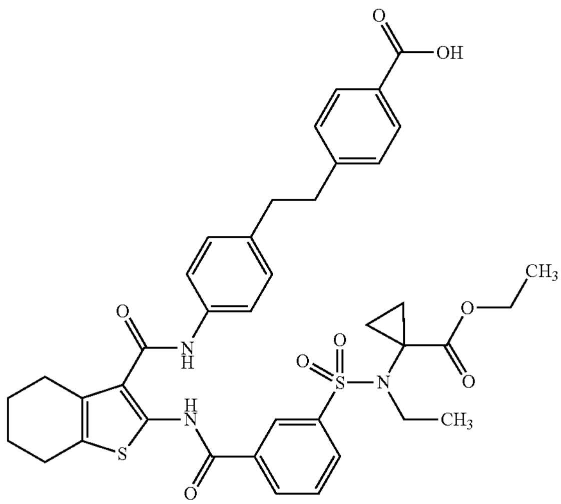 [SMILES: CCOC(=O)C1(N(CC)S(=O)(=O)c2cccc(C(=O)Nc3sc4c(c3C(=O)Nc3ccc(CCc5ccc(C(=O)O)cc5)cc3)CCCC4)c2)CC1] | 16 |
| 71 | 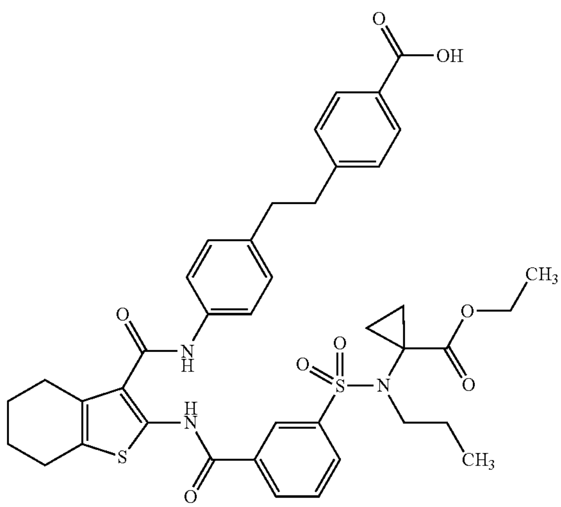 [SMILES: CCCN(C1(C(=O)OCC)CC1)S(=O)(=O)c1cccc(C(=O)Nc2sc3c(c2C(=O)Nc2ccc(CCc4ccc(C(=O)O)cc4)cc2)CCCC3)c1] | 16 |
| 72 | 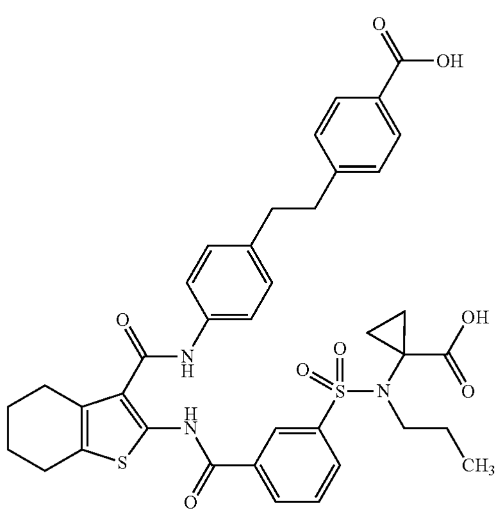 [SMILES: CCCN(C1(C(=O)O)CC1)S(=O)(=O)c1cccc(C(=O)Nc2sc3c(c2C(=O)Nc2ccc(CCc4ccc(C(=O)O)cc4)cc2)CCCC3)c1] | 17 |

TABLE 28
| Ex | Structure | Syn |
|---|---|---|
| 73 | 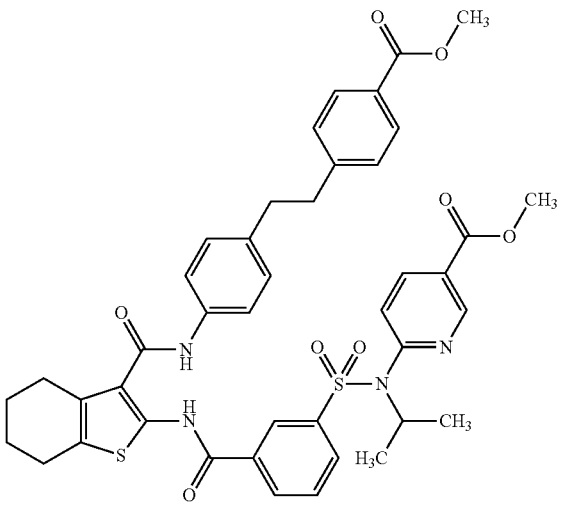 [SMILES: COC(=O)c1ccc(CCc2ccc(NC(=O)c3c(NC(=O)c4cccc(S(=O)(=O)N(c5ccc(C(=O)OC)cn5)C(C)C)c4)sc4c3CCCC4)cc2)cc1] | 18 |
| 74 | 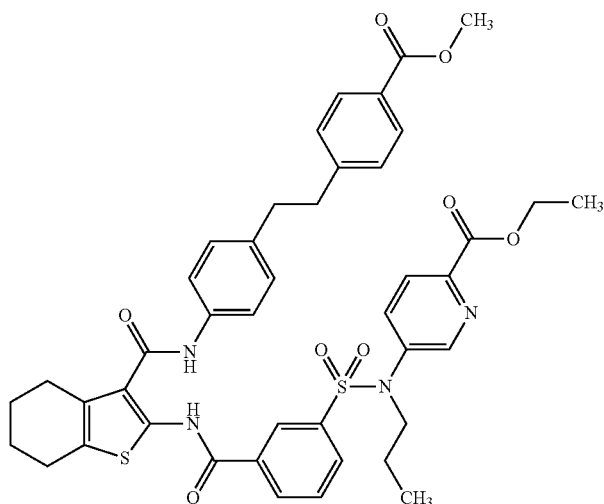 | 18 |

TABLE 29

| Ex | Structure | Syn |
|----|-----------|-----|
| 75 | 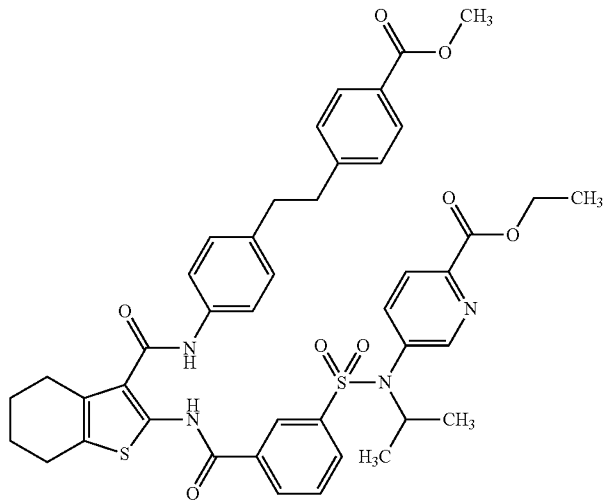 [SMILES: CCOC(=O)c1ccc(N(C(C)C)S(=O)(=O)c2cccc(C(=O)Nc3sc4c(c3C(=O)Nc3ccc(CCc5ccc(C(=O)OC)cc5)cc3)CCCC4)c2)cn1] | 18 |
| 76 | 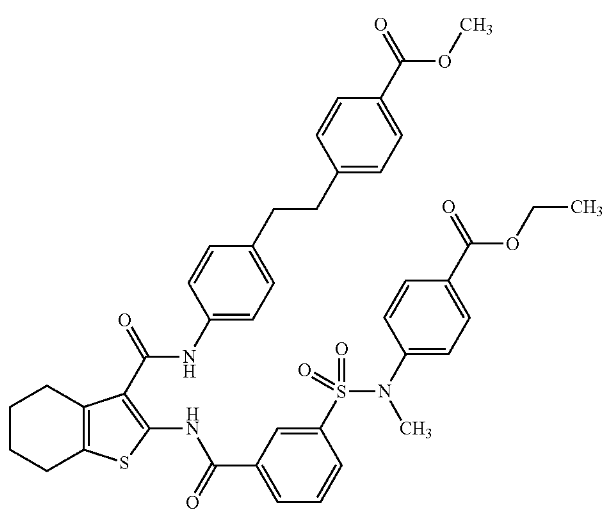 [SMILES: CCOC(=O)c1ccc(N(C)S(=O)(=O)c2cccc(C(=O)Nc3sc4c(c3C(=O)Nc3ccc(CCc5ccc(C(=O)OC)cc5)cc3)CCCC4)c2)cc1] | 20 |

TABLE 30
| Ex | Structure | Syn |
|---|---|---|
| 77 | 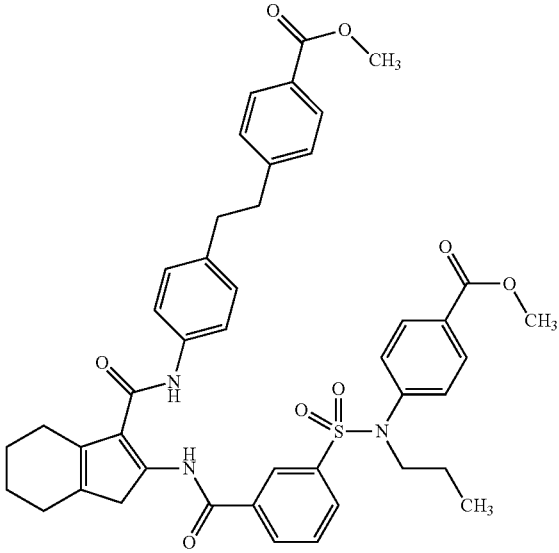 [SMILES: CCCN(c1ccc(C(=O)OC)cc1)S(=O)(=O)c1cccc(C(=O)NC2=C(C(=O)Nc3ccc(CCc4ccc(C(=O)OC)cc4)cc3)C3=C(CCCC3)C2)c1] | 20 |
| 78 | 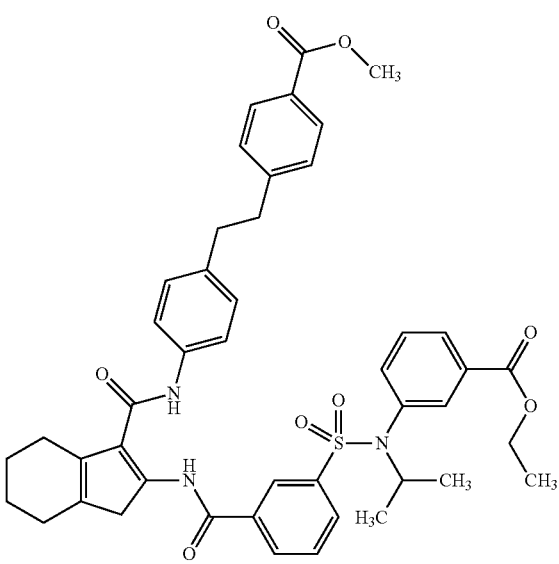 [SMILES: CCOC(=O)c1cccc(N(C(C)C)S(=O)(=O)c2cccc(C(=O)NC3=C(C(=O)Nc4ccc(CCc5ccc(C(=O)OC)cc5)cc4)C4=C(CCCC4)C3)c2)c1] | 20 |

TABLE 31
| Ex | Structure | Syn |
|---|---|---|
| 79 | 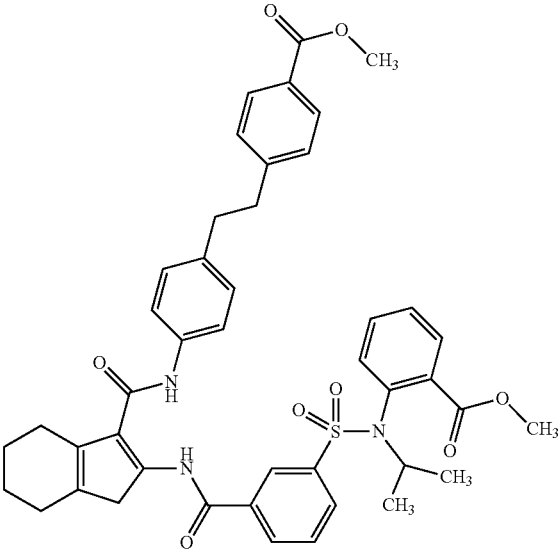 [SMILES: COC(=O)c1ccc(CCc2ccc(NC(=O)C3=C(NC(=O)c4cccc(S(=O)(=O)N(c5ccccc5C(=O)OC)C(C)C)c4)CC4=C3CCCC4)cc2)cc1] | 20 |
| 80 | 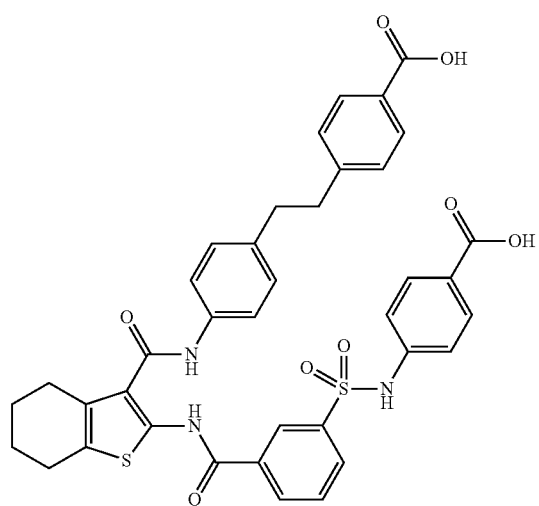 [SMILES: O=C(O)c1ccc(CCc2ccc(NC(=O)c3c(NC(=O)c4cccc(S(=O)(=O)Nc5ccc(C(=O)O)cc5)c4)sc4c3CCCC4)cc2)cc1] | 21 |

TABLE 32
| Ex | Structure | Syn |
|----|-----------|-----|
| 81 | 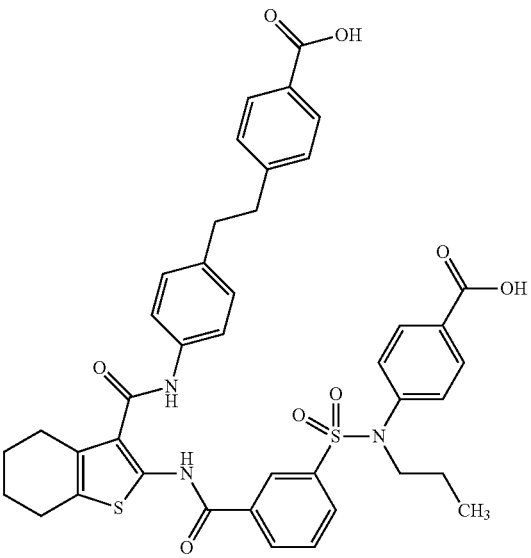 [SMILES: CCCN(c1ccc(C(=O)O)cc1)S(=O)(=O)c1cccc(C(=O)Nc2sc3c(c2C(=O)Nc2ccc(CCc4ccc(C(=O)O)cc4)cc2)CCCC3)c1] | 21 |
| 82 | 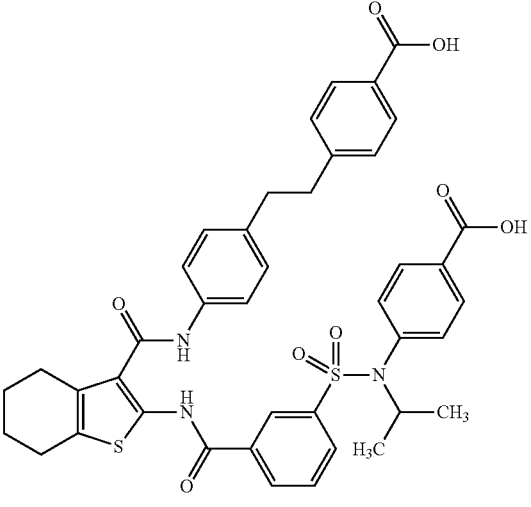 [SMILES: CC(C)N(c1ccc(C(=O)O)cc1)S(=O)(=O)c1cccc(C(=O)Nc2sc3c(c2C(=O)Nc2ccc(CCc4ccc(C(=O)O)cc4)cc2)CCCC3)c1] | 21 |

TABLE 33
| Ex | Structure | Syn |
|---|---|---|
| 83 | 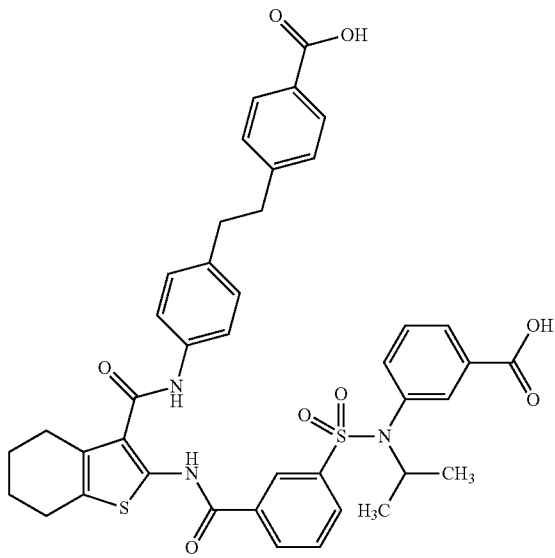 [SMILES: CC(C)N(c1cccc(C(=O)O)c1)S(=O)(=O)c1cccc(C(=O)Nc2sc3c(c2C(=O)Nc2ccc(CCc4ccc(C(=O)O)cc4)cc2)CCCC3)c1] | 21 |
| 84 | 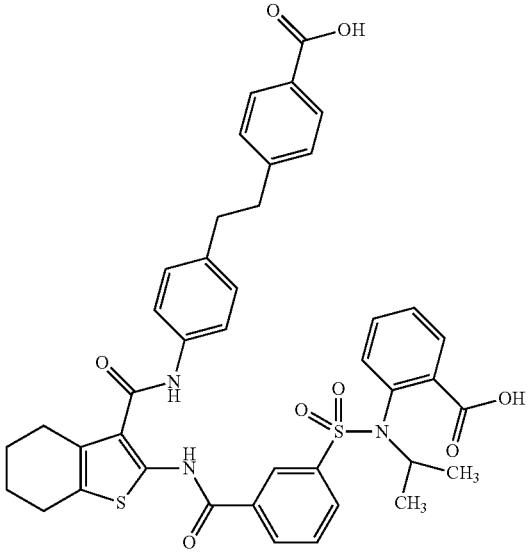 [SMILES: CC(C)N(c1ccccc1C(=O)O)S(=O)(=O)c1cccc(C(=O)Nc2sc3c(c2C(=O)Nc2ccc(CCc4ccc(C(=O)O)cc4)cc2)CCCC3)c1] | 21 |

TABLE 34
| Ex | Structure | Syn |
|---|---|---|
| 85 | 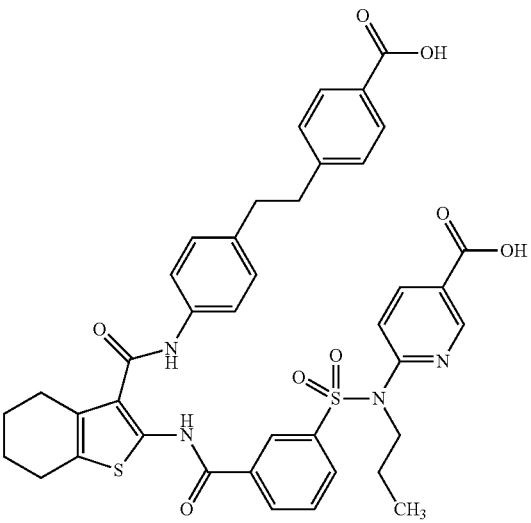 [SMILES: CCCN(c1ccc(C(=O)O)cn1)S(=O)(=O)c1cccc(C(=O)Nc2sc3c(c2C(=O)Nc2ccc(CCc4ccc(C(=O)O)cc4)cc2)CCCC3)c1] | 21 |
| 86 | 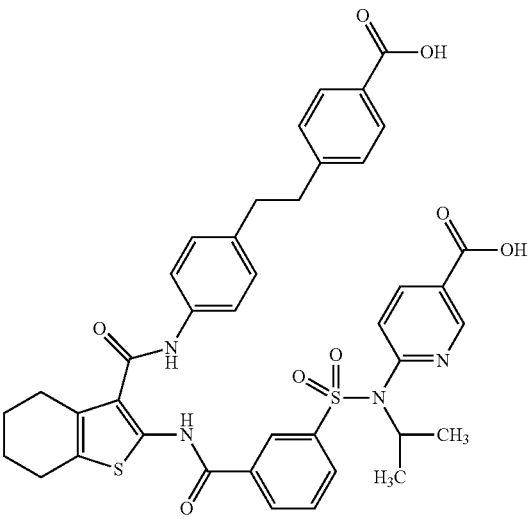 [SMILES: CC(C)N(c1ccc(C(=O)O)cn1)S(=O)(=O)c1cccc(C(=O)Nc2sc3c(c2C(=O)Nc2ccc(CCc4ccc(C(=O)O)cc4)cc2)CCCC3)c1] | 21 |

TABLE 35
| Ex | Structure | Syn |
|----|-----------|-----|
| 87 | 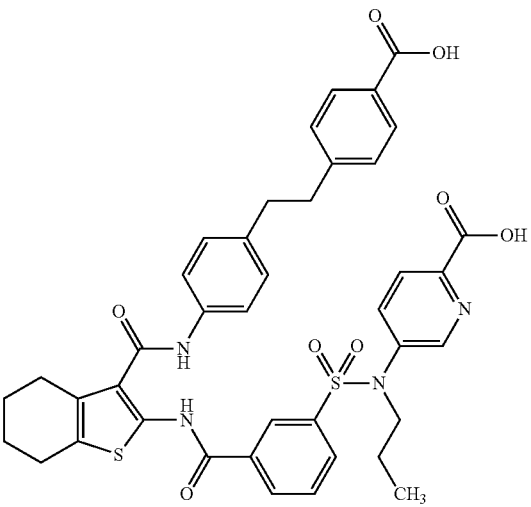 [SMILES: CCCN(c1ccc(C(=O)O)nc1)S(=O)(=O)c1cccc(C(=O)Nc2sc3c(c2C(=O)Nc2ccc(CCc4ccc(C(=O)O)cc4)cc2)CCCC3)c1] | 21 |
| 88 | 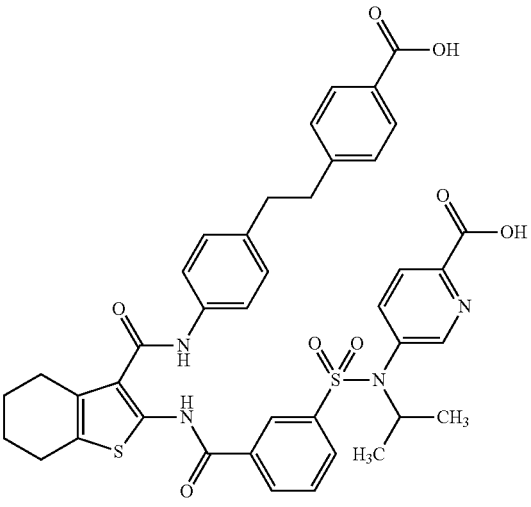 [SMILES: CC(C)N(c1ccc(C(=O)O)nc1)S(=O)(=O)c1cccc(C(=O)Nc2sc3c(c2C(=O)Nc2ccc(CCc4ccc(C(=O)O)cc4)cc2)CCCC3)c1] | 21 |

TABLE 36
| Ex | Structure | Syn |
|---|---|---|
| 89 | 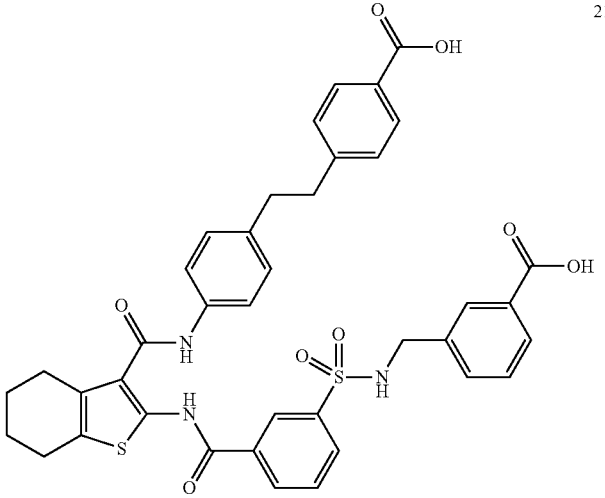 | 21 |
| 90 | 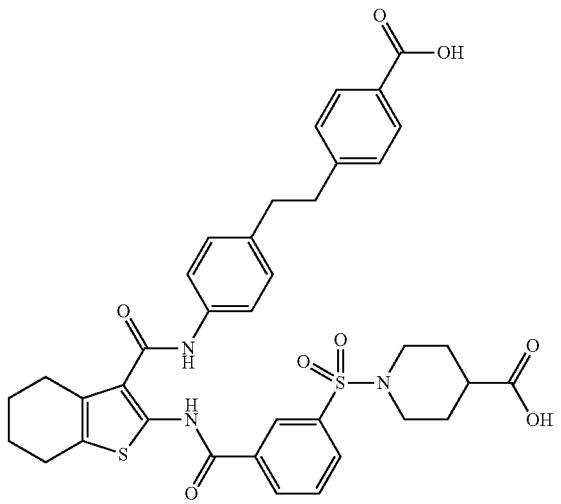 [SMILES: O=C(O)c1ccc(CCc2ccc(NC(=O)c3c(NC(=O)c4cccc(S(=O)(=O)N5CCC(C(=O)O)CC5)c4)sc4c3CCCC4)cc2)cc1] | 21 |

TABLE 37
| Ex | Structure | Syn |
|----|-----------|-----|
| 91 | 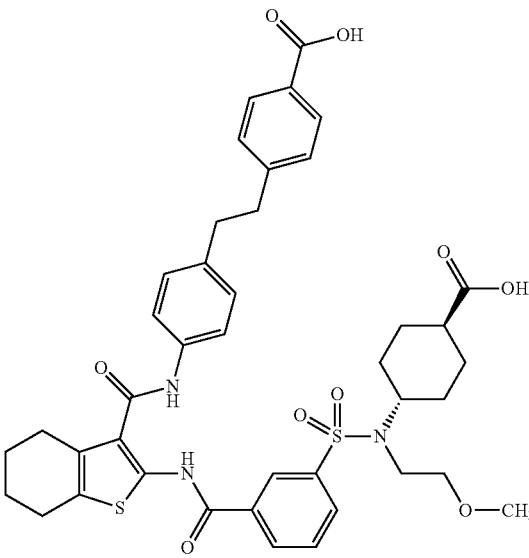 | 21 |
| 92 | 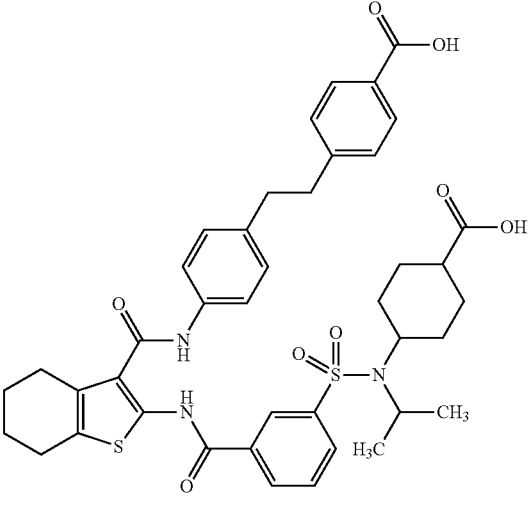 [SMILES: CC(C)N(C1CCC(C(=O)O)CC1)S(=O)(=O)c1cccc(C(=O)Nc2sc3c(c2C(=O)Nc2ccc(CCc4ccc(C(=O)O)cc4)cc2)CCCC3)c1] | 21 |

TABLE 38

| Ex | Structure | Syn |
|---|---|---|
| 93 | (structure) | 21 |
| 94 | (structure) | 21 |

TABLE 39

| Ex | Structure | Syn |
|---|---|---|
| 95 | 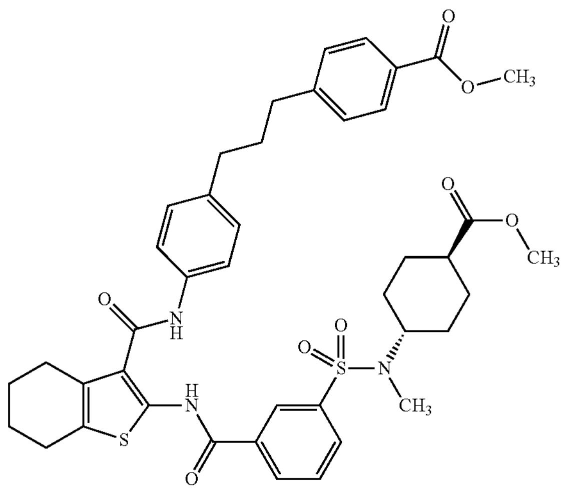 [SMILES: COC(=O)c1ccc(CCCc2ccc(NC(=O)c3c(NC(=O)c4cccc(S(=O)(=O)N(C)[C@H]5CC[C@H](C(=O)OC)CC5)c4)sc4c3CCCC4)cc2)cc1] | 22 |
| 96 | 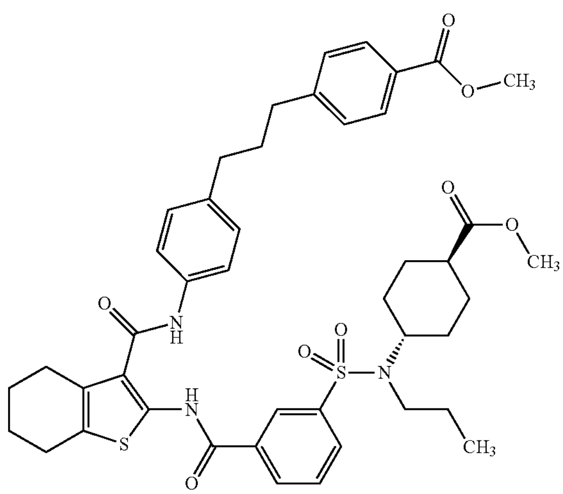 [SMILES: CCCN([C@H]1CC[C@H](C(=O)OC)CC1)S(=O)(=O)c1cccc(C(=O)Nc2sc3c(c2C(=O)Nc2ccc(CCCc4ccc(C(=O)OC)cc4)cc2)CCCC3)c1] | 22 |
| 97 | 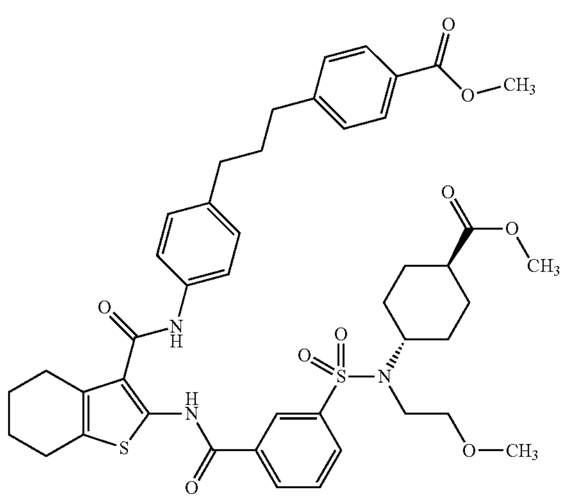 [SMILES: COCCN([C@H]1CC[C@H](C(=O)OC)CC1)S(=O)(=O)c1cccc(C(=O)Nc2sc3c(c2C(=O)Nc2ccc(CCCc4ccc(C(=O)OC)cc4)cc2)CCCC3)c1] | 22 |

TABLE 40
| Ex | Structure | Syn |
|---|---|---|
| 98 | 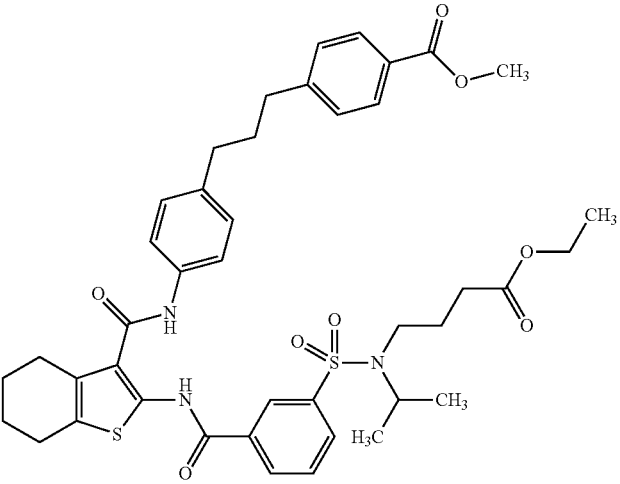 [SMILES: CCOC(=O)CCCN(C(C)C)S(=O)(=O)c1cccc(C(=O)Nc2sc3c(c2C(=O)Nc2ccc(CCCc4ccc(C(=O)OC)cc4)cc2)CCCC3)c1] | 22 |
| 99 | 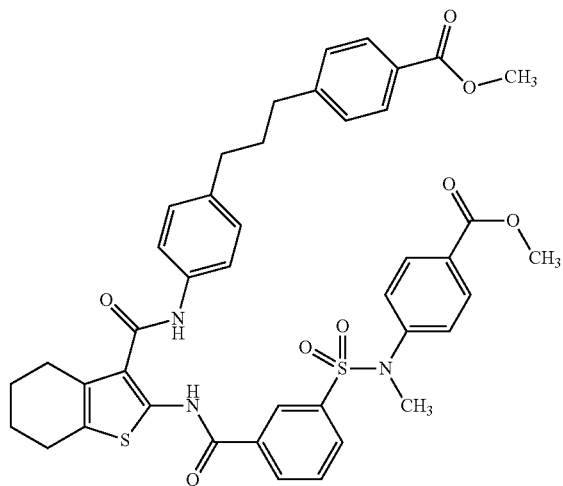 [SMILES: COC(=O)c1ccc(CCCc2ccc(NC(=O)c3c(NC(=O)c4cccc(S(=O)(=O)N(C)c5ccc(C(=O)OC)cc5)c4)sc4c3CCCC4)cc2)cc1] | 22 |
| 100 | 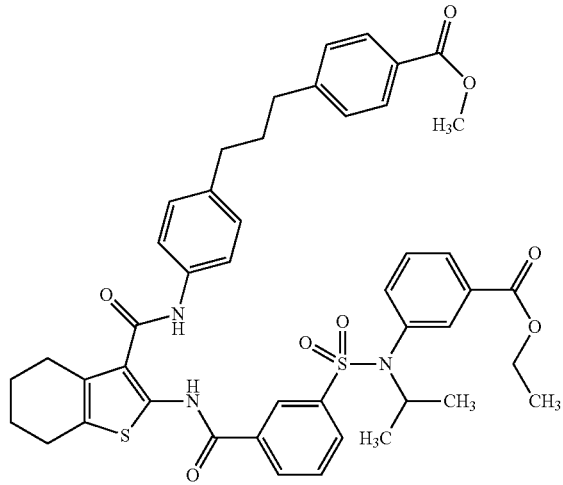 [SMILES: CCOC(=O)c1cccc(N(C(C)C)S(=O)(=O)c2cccc(C(=O)Nc3sc4c(c3C(=O)Nc3ccc(CCCc5ccc(C(=O)OC)cc5)cc3)CCCC4)c2)c1] | 22 |

TABLE 41

| Ex | Structure | Syn |
|---|---|---|
| 101 | 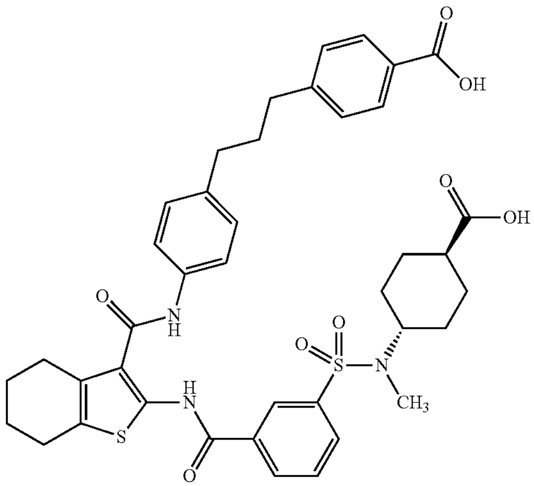 [SMILES: CN([C@H]1CC[C@H](C(=O)O)CC1)S(=O)(=O)c1cccc(C(=O)Nc2sc3c(c2C(=O)Nc2ccc(CCCc4ccc(C(=O)O)cc4)cc2)CCCC3)c1] | 23 |
| 102 | 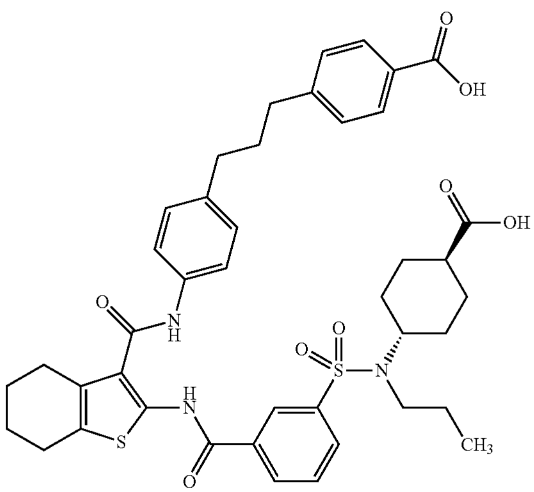 [SMILES: CCCN([C@H]1CC[C@H](C(=O)O)CC1)S(=O)(=O)c1cccc(C(=O)Nc2sc3c(c2C(=O)Nc2ccc(CCCc4ccc(C(=O)O)cc4)cc2)CCCC3)c1] | 23 |
| 103 | 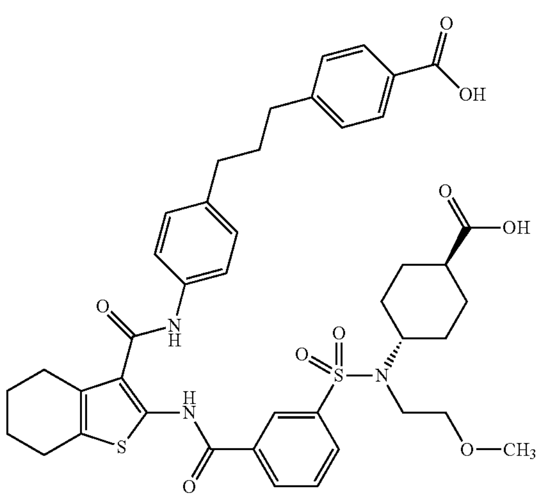 [SMILES: COCCN([C@H]1CC[C@H](C(=O)O)CC1)S(=O)(=O)c1cccc(C(=O)Nc2sc3c(c2C(=O)Nc2ccc(CCCc4ccc(C(=O)O)cc4)cc2)CCCC3)c1] | 23 |

TABLE 42

| Ex | Structure | Syn |
|---|---|---|
| 104 | 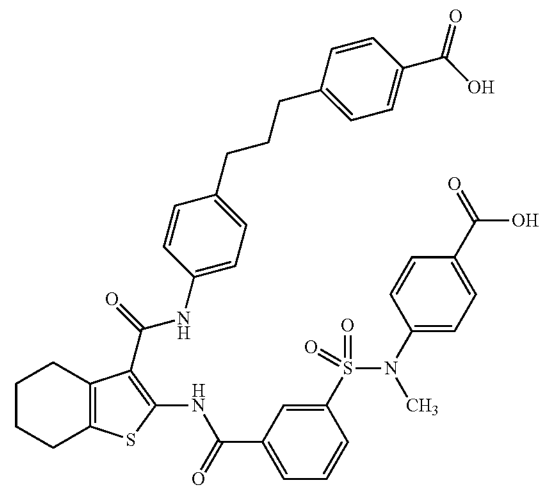 [SMILES: CN(c1ccc(C(=O)O)cc1)S(=O)(=O)c1cccc(C(=O)Nc2sc3c(c2C(=O)Nc2ccc(CCCc4ccc(C(=O)O)cc4)cc2)CCCC3)c1] | 23 |
| 105 | 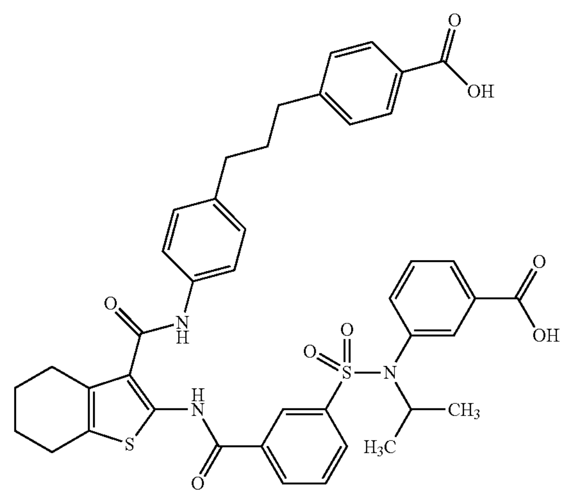 [SMILES: CC(C)N(c1cccc(C(=O)O)c1)S(=O)(=O)c1cccc(C(=O)Nc2sc3c(c2C(=O)Nc2ccc(CCCc4ccc(C(=O)O)cc4)cc2)CCCC3)c1] | 23 |
| 106 | 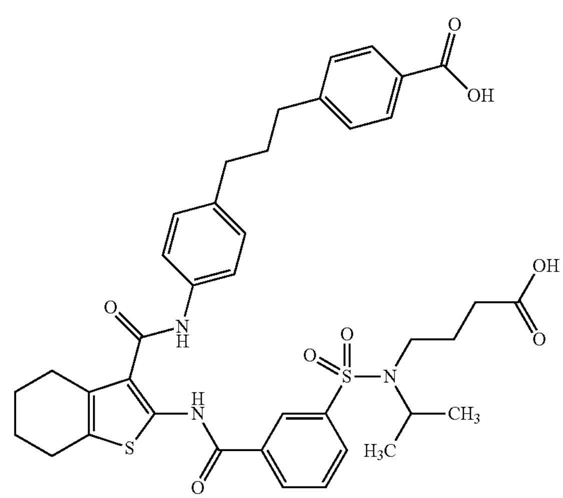 [SMILES: CC(C)N(CCCC(=O)O)S(=O)(=O)c1cccc(C(=O)Nc2sc3c(c2C(=O)Nc2ccc(CCCc4ccc(C(=O)O)cc4)cc2)CCCC3)c1] | 23 |

TABLE 43

| Ex | Structure | Syn |
|---|---|---|
| 107 | 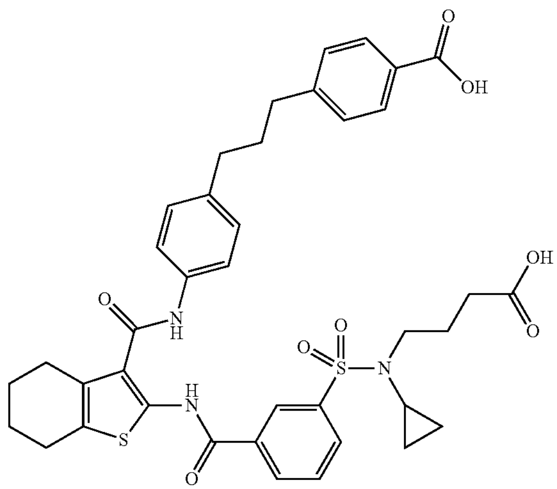 [SMILES: O=C(O)CCCN(C1CC1)S(=O)(=O)c1cccc(C(=O)Nc2sc3c(c2C(=O)Nc2ccc(CCCc4ccc(C(=O)O)cc4)cc2)CCCC3)c1] | 23 |
| 108 | 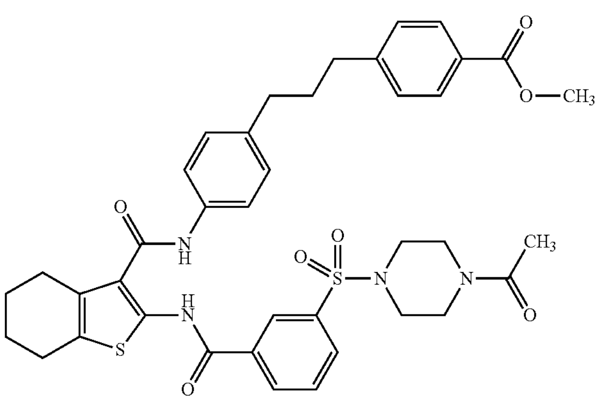 [SMILES: COC(=O)c1ccc(CCCc2ccc(NC(=O)c3c(NC(=O)c4cccc(S(=O)(=O)N5CCN(C(C)=O)CC5)c4)sc4c3CCCC4)cc2)cc1] | 26 |
| 109 | 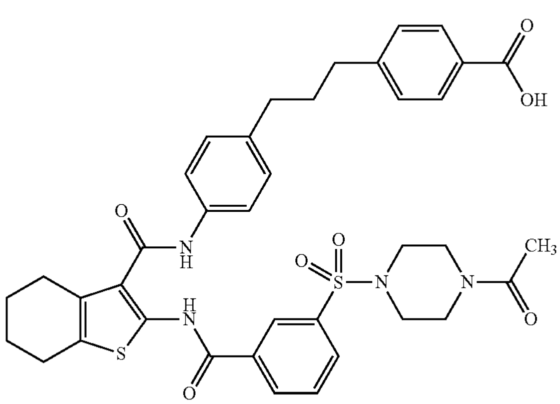 [SMILES: CC(=O)N1CCN(S(=O)(=O)c2cccc(C(=O)Nc3sc4c(c3C(=O)Nc3ccc(CCCc5ccc(C(=O)O)cc5)cc3)CCCC4)c2)CC1] | 27 |

TABLE 44
| Ex | Structure | Syn |
|---|---|---|
| 110 | 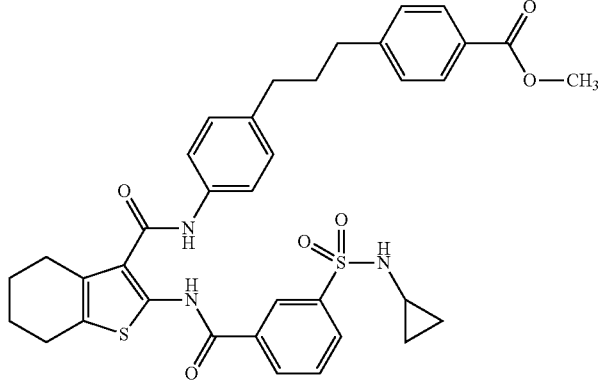 [SMILES: COC(=O)c1ccc(CCCc2ccc(NC(=O)c3c(NC(=O)c4cccc(S(=O)(=O)NC5CC5)c4)sc4c3CCCC4)cc2)cc1] | 32 |
| 111 | 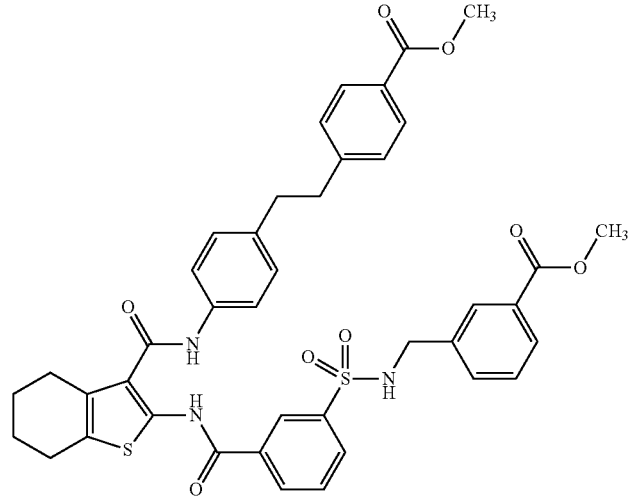 [SMILES: COC(=O)c1ccc(CCc2ccc(NC(=O)c3c(NC(=O)c4cccc(S(=O)(=O)NCc5cccc(C(=O)OC)c5)c4)sc4c3CCCC4)cc2)cc1] | 33 |
| 112 | 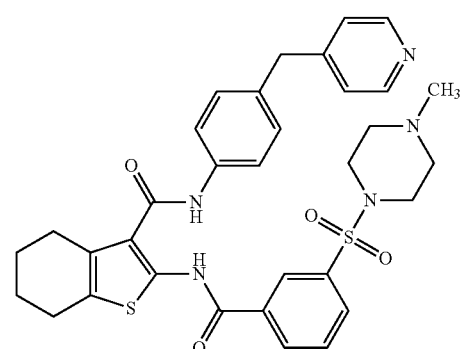 | 36 |

TABLE 45

| Ex | Structure | Syn |
|---|---|---|
| 113 | 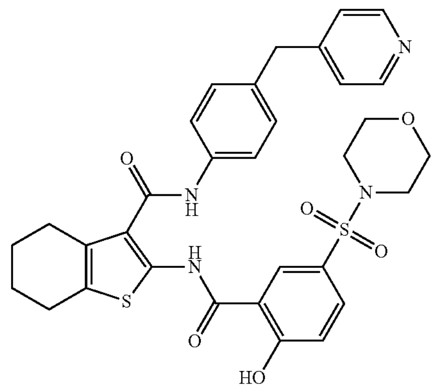 [SMILES: O=C(Nc1sc2c(c1C(=O)Nc1ccc(Cc3ccncc3)cc1)CCCC2)c1cc(S(=O)(=O)N2CCOCC2)ccc1O] | 36 |
| 114 | 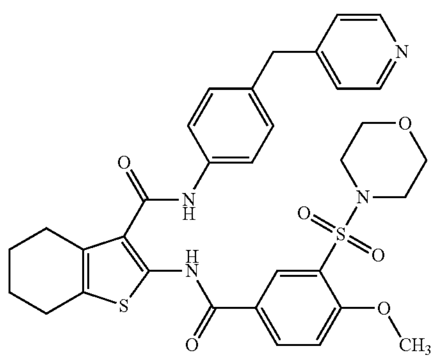 [SMILES: COc1ccc(C(=O)Nc2sc3c(c2C(=O)Nc2ccc(Cc4ccncc4)cc2)CCCC3)cc1S(=O)(=O)N1CCOCC1] | 36 |
| 115 | 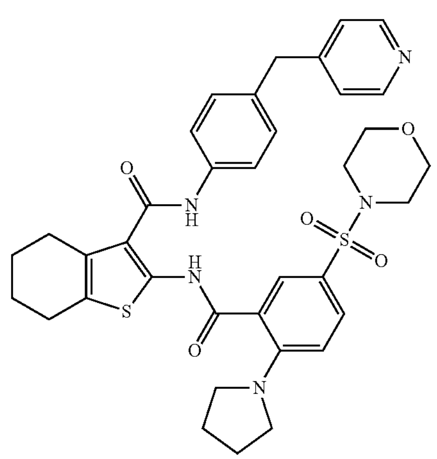 [SMILES: O=C(Nc1sc2c(c1C(=O)Nc1ccc(Cc3ccncc3)cc1)CCCC2)c1cc(S(=O)(=O)N2CCOCC2)ccc1N1CCCC1] | 36 |

TABLE 46

| Ex | Structure | Syn |
|---|---|---|
| 116 | 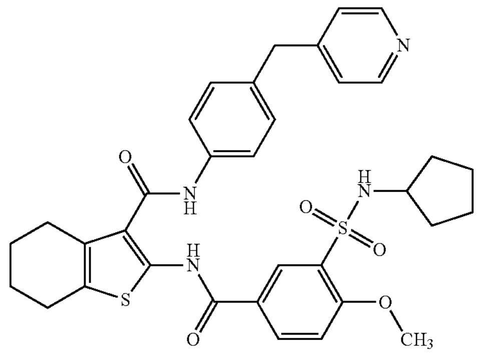 [SMILES: COc1ccc(C(=O)Nc2sc3c(c2C(=O)Nc2ccc(Cc4ccncc4)cc2)CCCC3)cc1S(=O)(=O)NC1CCCC1] | 36 |
| 117 | 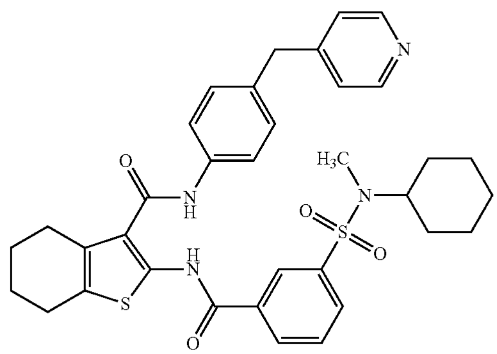 [SMILES: CN(C1CCCCC1)S(=O)(=O)c1cccc(C(=O)Nc2sc3c(c2C(=O)Nc2ccc(Cc4ccncc4)cc2)CCCC3)c1] | 36 |
| 118 | 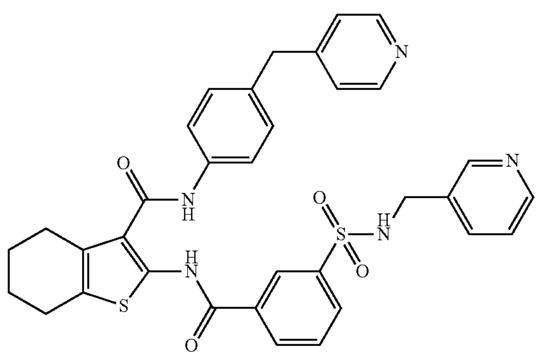 [SMILES: O=C(Nc1sc2c(c1C(=O)Nc1ccc(Cc3ccncc3)cc1)CCCC2)c1cccc(S(=O)(=O)NCc2cccnc2)c1] | 36 |
| 119 | 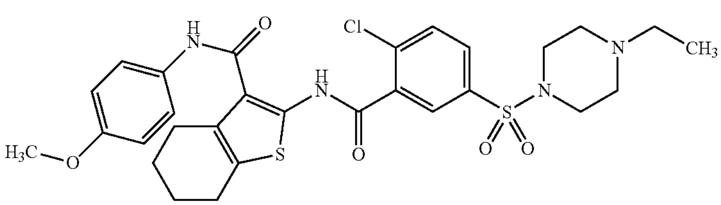 [SMILES: CCN1CCN(S(=O)(=O)c2ccc(Cl)c(C(=O)Nc3sc4c(c3C(=O)Nc3ccc(OC)cc3)CCCC4)c2)CC1] | 35 |

TABLE 47

| Ex | Structure | Syn |
|---|---|---|
| 120 | 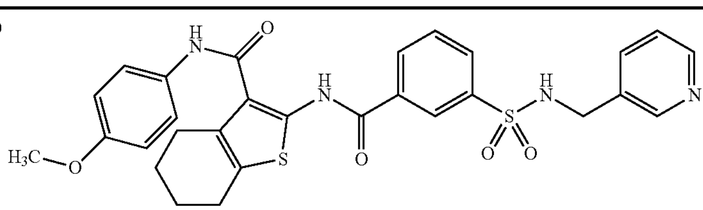 | 35 |

TABLE 47-continued

| Ex | Structure | Syn |
|---|---|---|
| 121 | 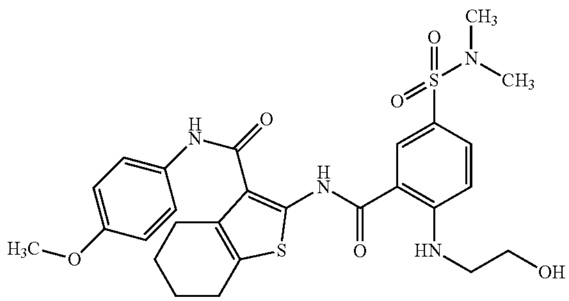 [SMILES: COc1ccc(NC(=O)c2c(NC(=O)c3cc(S(=O)(=O)N(C)C)ccc3NCCO)sc3c2CCCC3)cc1] | 35 |
| 122 | 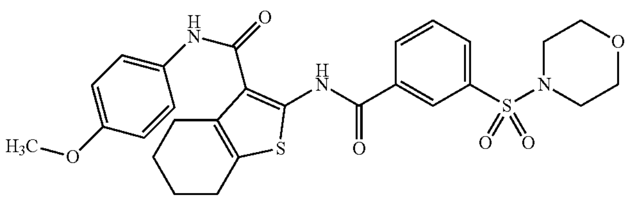 [SMILES: COc1ccc(NC(=O)c2c(NC(=O)c3cccc(S(=O)(=O)N4CCOCC4)c3)sc3c2CCCC3)cc1] | 35 |
| 123 | 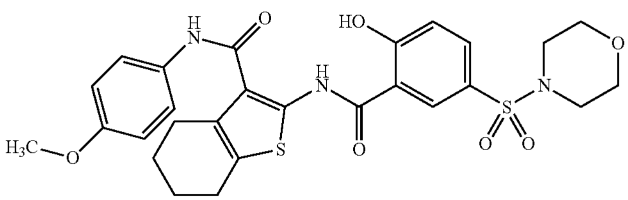 [SMILES: COc1ccc(NC(=O)c2c(NC(=O)c3cc(S(=O)(=O)N4CCOCC4)ccc3O)sc3c2CCCC3)cc1] | 35 |
| 124 | 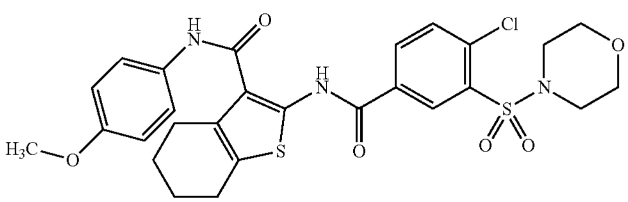 | 35 |

TABLE 48

| Ex | Structure | Syn |
|---|---|---|
| 125 | 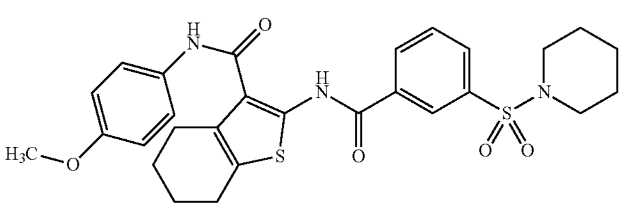 [SMILES: COc1ccc(NC(=O)c2c(NC(=O)c3cccc(S(=O)(=O)N4CCCCC4)c3)sc3c2CCCC3)cc1] | 35 |
| 126 | 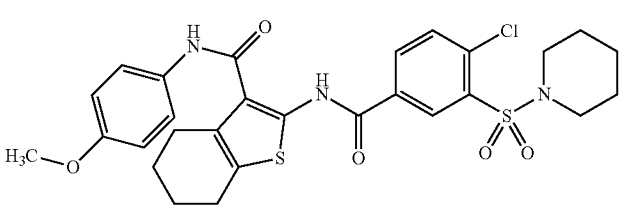 [SMILES: COc1ccc(NC(=O)c2c(NC(=O)c3ccc(Cl)c(S(=O)(=O)N4CCCCC4)c3)sc3c2CCCC3)cc1] | 35 |

TABLE 48-continued

| Ex | Structure | Syn |
|---|---|---|
| 127 | 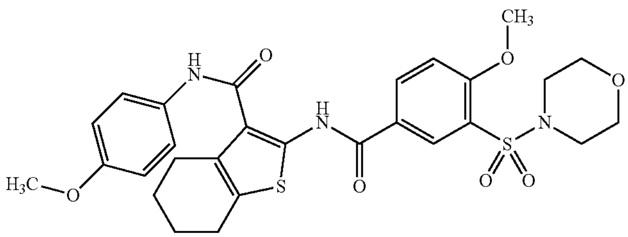 [SMILES: COc1ccc(NC(=O)c2c(NC(=O)c3ccc(OC)c(S(=O)(=O)N4CCOCC4)c3)sc3c2CCCC3)cc1] | 35 |
| 128 | 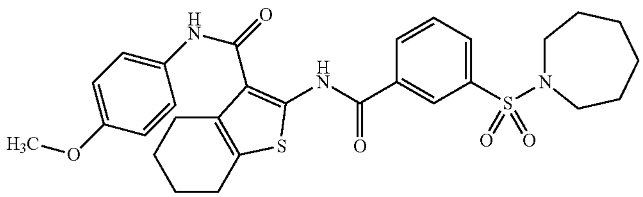 [SMILES: COc1ccc(NC(=O)c2c(NC(=O)c3cccc(S(=O)(=O)N4CCCCCC4)c3)sc3c2CCCC3)cc1] | 35 |
| 129 | 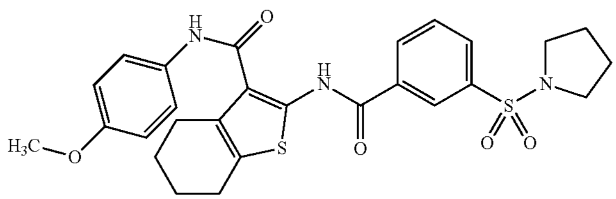 [SMILES: COc1ccc(NC(=O)c2c(NC(=O)c3cccc(S(=O)(=O)N4CCCC4)c3)sc3c2CCCC3)cc1] | 35 |

TABLE 49

| Ex | Structure | Syn |
|---|---|---|
| 130 | 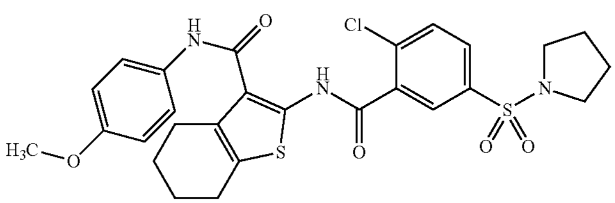 [SMILES: COc1ccc(NC(=O)c2c(NC(=O)c3cc(S(=O)(=O)N4CCCC4)ccc3Cl)sc3c2CCCC3)cc1] | 35 |
| 131 | 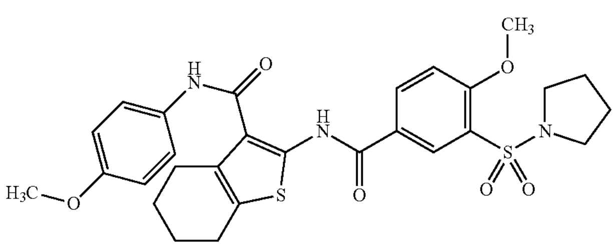 [SMILES: COc1ccc(NC(=O)c2c(NC(=O)c3ccc(OC)c(S(=O)(=O)N4CCCC4)c3)sc3c2CCCC3)cc1] | 35 |
| 132 | 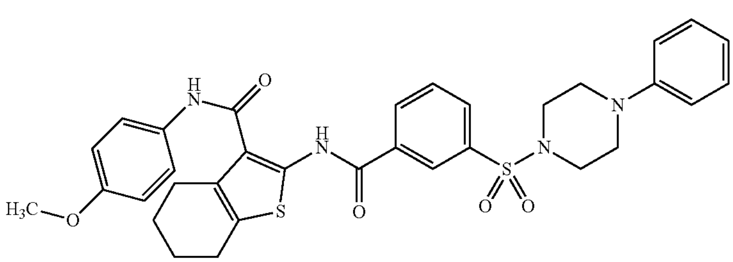 [SMILES: COc1ccc(NC(=O)c2c(NC(=O)c3cccc(S(=O)(=O)N4CCN(c5ccccc5)CC4)c3)sc3c2CCCC3)cc1] | 35 |

TABLE 49-continued

| Ex | Structure | Syn |
|---|---|---|
| 133 | 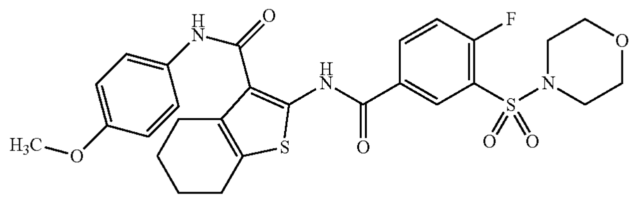 [SMILES: COc1ccc(NC(=O)c2c(NC(=O)c3ccc(F)c(S(=O)(=O)N4CCOCC4)c3)sc3c2CCCC3)cc1] | 35 |
| 134 | 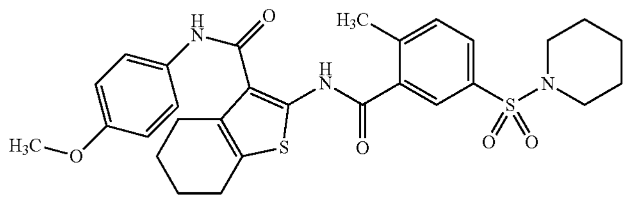 [SMILES: COc1ccc(NC(=O)c2c(NC(=O)c3cc(S(=O)(=O)N4CCCCC4)ccc3C)sc3c2CCCC3)cc1] | 35 |

TABLE 50

| Ex | Structure | Syn |
|---|---|---|
| 135 | 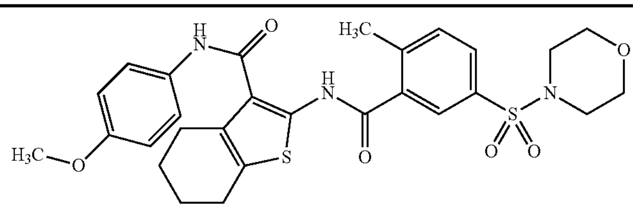 | 35 |
| 136 | 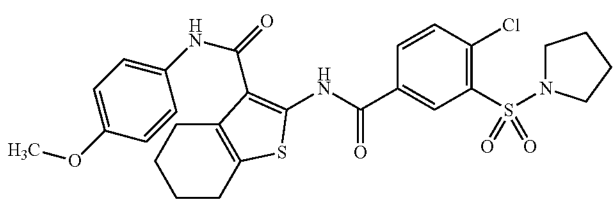 [SMILES: COc1ccc(NC(=O)c2c(NC(=O)c3ccc(Cl)c(S(=O)(=O)N4CCCC4)c3)sc3c2CCCC3)cc1] | 35 |
| 137 | 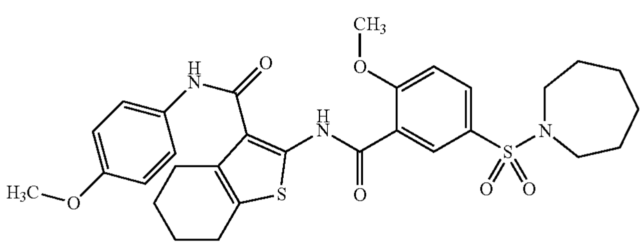 [SMILES: COc1ccc(NC(=O)c2c(NC(=O)c3cc(S(=O)(=O)N4CCCCCC4)ccc3OC)sc3c2CCCC3)cc1] | 35 |
| 138 | 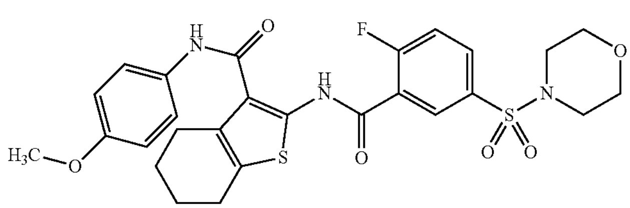 [SMILES: COc1ccc(NC(=O)c2c(NC(=O)c3cc(S(=O)(=O)N4CCOCC4)ccc3F)sc3c2CCCC3)cc1] | 35 |
| 139 | 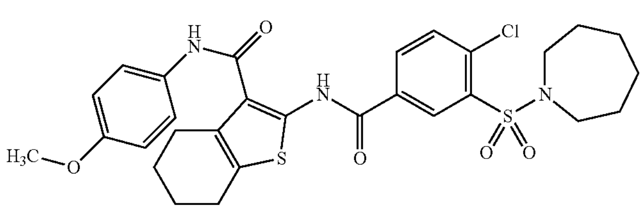 [SMILES: COc1ccc(NC(=O)c2c(NC(=O)c3ccc(Cl)c(S(=O)(=O)N4CCCCCC4)c3)sc3c2CCCC3)cc1] | 35 |

TABLE 51

| Ex | Structure | Syn |
|---|---|---|
| 140 | 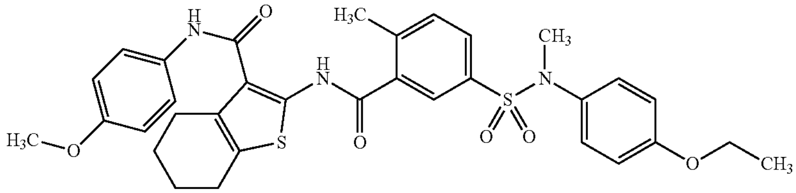 [SMILES: CCOc1ccc(N(C)S(=O)(=O)c2ccc(C)c(C(=O)Nc3sc4c(c3C(=O)Nc3ccc(OC)cc3)CCCC4)c2)cc1] | 35 |
| 141 | 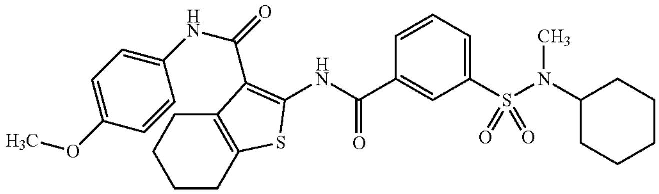 [SMILES: COc1ccc(NC(=O)c2c(NC(=O)c3cccc(S(=O)(=O)N(C)C4CCCCC4)c3)sc3c2CCCC3)cc1] | 35 |
| 142 | 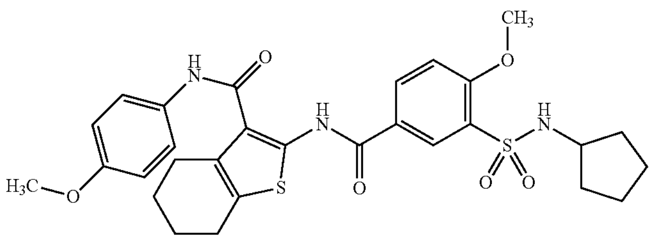 [SMILES: COc1ccc(NC(=O)c2c(NC(=O)c3ccc(OC)c(S(=O)(=O)NC4CCCC4)c3)sc3c2CCCC3)cc1] | 35 |
| 143 | 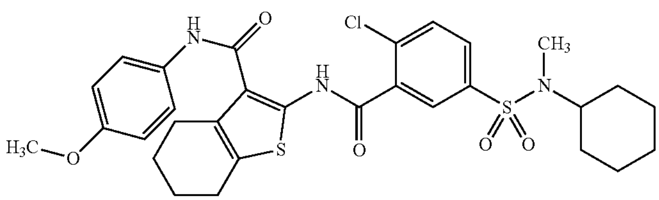 [SMILES: COc1ccc(NC(=O)c2c(NC(=O)c3cc(S(=O)(=O)N(C)C4CCCCC4)ccc3Cl)sc3c2CCCC3)cc1] | 35 |
| 144 | 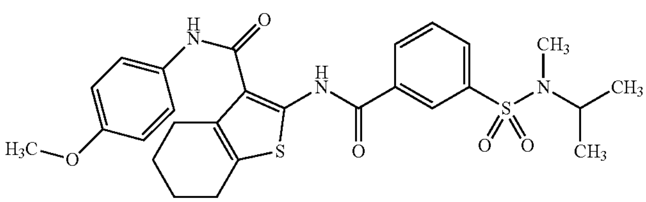 [SMILES: COc1ccc(NC(=O)c2c(NC(=O)c3cccc(S(=O)(=O)N(C)C(C)C)c3)sc3c2CCCC3)cc1] | 35 |

TABLE 52

| Ex | Structure | Syn |
|---|---|---|
| 145 | 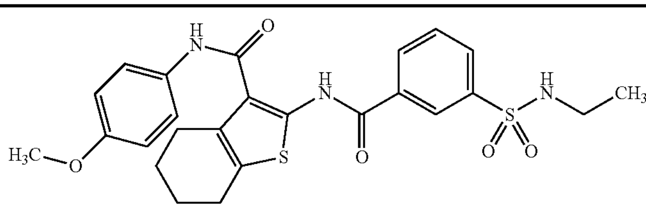 | 35 |
| 146 | 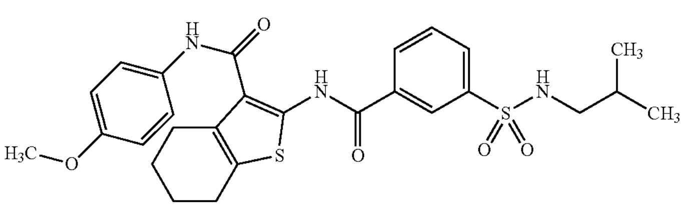 [SMILES: COc1ccc(NC(=O)c2c(NC(=O)c3cccc(S(=O)(=O)NCC(C)C)c3)sc3c2CCCC3)cc1] | 35 |

TABLE 52-continued

| Ex | Structure | Syn |
|---|---|---|
| 147 | 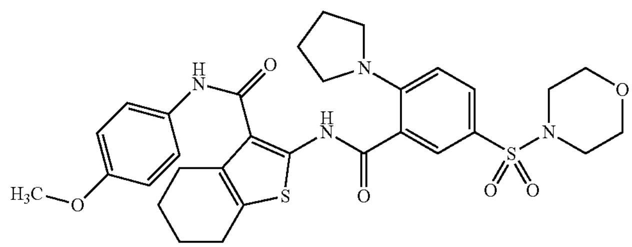 [SMILES: COc1ccc(NC(=O)c2c(NC(=O)c3cc(S(=O)(=O)N4CCOCC4)ccc3N3CCCC3)sc3c2CCCC3)cc1] | 35 |
| 148 | 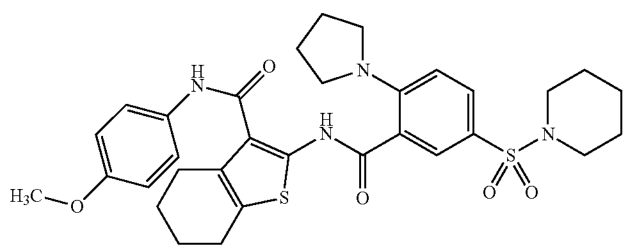 [SMILES: COc1ccc(NC(=O)c2c(NC(=O)c3cc(S(=O)(=O)N4CCCCC4)ccc3N3CCCC3)sc3c2CCCC3)cc1] | 35 |
| 149 | 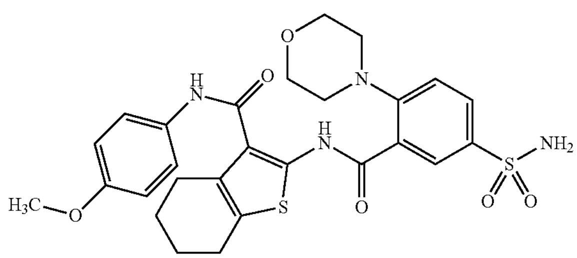 [SMILES: COc1ccc(NC(=O)c2c(NC(=O)c3cc(S(N)(=O)=O)ccc3N3CCOCC3)sc3c2CCCC3)cc1] | 35 |

TABLE 53

| Ex | Structure | Syn |
|---|---|---|
| 150 | 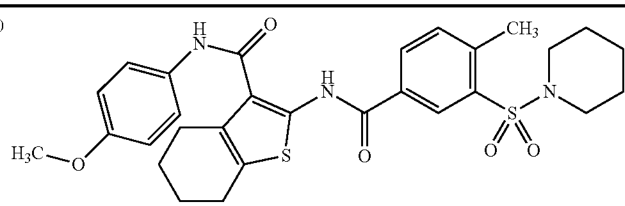 | 35 |
| 151 | 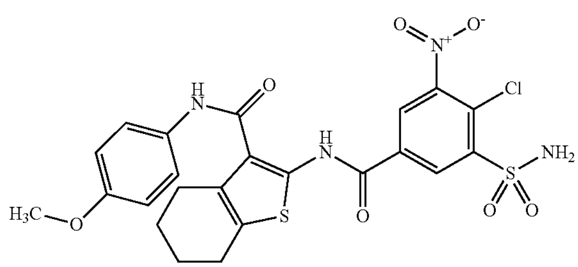 [SMILES: COc1ccc(NC(=O)c2c(NC(=O)c3cc([N+](=O)[O-])c(Cl)c(S(N)(=O)=O)c3)sc3c2CCCC3)cc1] | 35 |
| 152 | 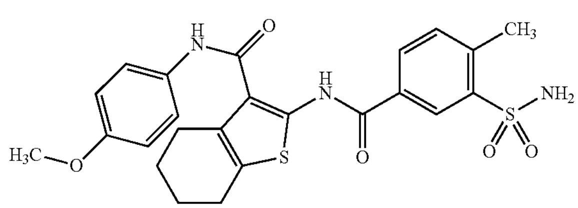 [SMILES: COc1ccc(NC(=O)c2c(NC(=O)c3ccc(C)c(S(N)(=O)=O)c3)sc3c2CCCC3)cc1] | 35 |

TABLE 53-continued

| Ex | Structure | Syn |
|---|---|---|
| 153 | 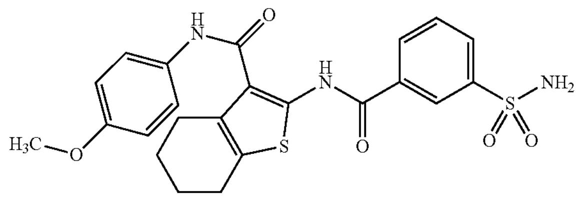 [SMILES: COc1ccc(NC(=O)c2c(NC(=O)c3cccc(S(N)(=O)=O)c3)sc3c2CCCC3)cc1] | 35 |

TABLE 54

| Ex | Data |
|---|---|
| 1 | ESI+: 786 |
| 2 | ESI+: 758<br>NMR: 1.13(3H, t, J = 7.0 Hz), 1.26-1.40(2H, m), 1.41-1.55(4H, m), 1.69-1.92 (6H, m), 2.05-2.14(1H, m), 2.64-2.78(4H, m), 2.84-3.01(4H, m), 3.20(2H, q, J = 7.0 Hz), 3.52-3.64(1H, m), 7.17(2H, d, J = 8.4 Hz), 7.35 (2H, d, J = 8.3 Hz), 7.61(2H, d, J = 8.4 Hz), 7.73-7.79(1H, m), 7.85(2H, d, J = 8.3 Hz), 8.07(1H, d, J = 8.1 Hz), 8.10(1H, d, J = 7.9 Hz), 8.27(1H, s), 9.67(1H, s), 11.67(1H, s), 12.06-12.75(2H, m).<br>m.p.: 262.8° C. |
| 3 | APCI/ESI−: 810 |
| 4 | ESI+: 770<br>NMR: 0.70-0.89(4H, m), 1.27-1.40(2H, m), 1.44-1.53(2H, m), 1.56-1.70(2H, m), 1.70-1.93(6H, m), 1.98-2.13(2H, m), 2.66-2.78(4H, m), 2.85-3.00 (4H, m), 3.65-3.74(1H, m), 7.17(2H, d, J = 8.5 Hz), 7.35(2H, d, J = 8.2 Hz), 7.59 (2H, d, J = 8.5 Hz), 7.78-7.87(3H, m), 8.09(1H, d, J = 7.9 Hz), 8.15(1H, d, J = 7.9 Hz), 8.27(1H, s), 9.64(1H, s), 11.72(1H, s), 12.16-12.66(2H, m). |
| 5 | ESI+: 770<br>NMR: 0.65-0.73(2H, m), 0.76-0.82(2H, m), 1.27-1.37(2H, m), 1.37-1.50(2H, m), 1.62-1.86(6H, m), 1.93-2.07(3H, m), 2.41-2.47(1H, m), 2.65-2.79 (4H, m), 2.85-3.00(4H, m), 3.67-3.78(1H, m), 7.18(2H, d, J = 8.4 Hz), 7.35 (2H, d, J = 8.2 Hz), 7.60(2H, d, J = 8.4 Hz), 7.78-7.87(3H, m), 8.07(1H, d, J = 7.7 Hz), 8.16(1H, d, J = 7.8 Hz), 8.27(1H, s), 9.63(1H, s), 11.73(1H, s), 12.36-12.57(2H, m).<br>m.p.: 186.8° C. |
| 6 | FAB+: 744 |
| 7 | FAB−: 770 |
| 8 | ESI+: 760 |
| 9 | ESI+: 760 |

TABLE 55

| Ex | Data |
|---|---|
| 10 | APCI/ESI−: 688<br>NMR: 1.70-1.86(4H, m), 2.43-2.48(2H, m), 2.64-2.78(7H, m), 2.84-2.99(4H, m), 3.21(2H, t, J = 7.2 Hz), 7.17(2H, d, J = 8.5 Hz), 7.35(2H, d, J = 8.2 Hz), 7.60(2H, d, J = 8.5 Hz), 7.78-7.87(3H, m), 8.00(1H, d, J = 8.3 Hz), 8.15(1H, d, J = 7.9 Hz), 8.23(1H, s), 9.68(1H, s), 11.65(1H, s), 12.35-12.69(2H, m).<br>m.p.: 230.3° C. |
| 11 | ESI+: 772 |
| 12 | ESI+: 730<br>NMR: 0.64-0.79(4H, m), 1.67-1.87(6H, m), 2.05-2.13(1H, m), 2.21(2H, t, J = 7.2 Hz), 2.65-2.78(4H, m), 2.84-3.00(4H, m), 3.16(2H, t, J = 7.4 Hz), 7.18 (2H, d, J = 8.5 Hz), 7.35(2H, d, J = 8.2 Hz), 7.60(2H, d, J = 8.5 Hz), 7.77-7.87 (3H, m), 8.04(1H, d, J = 8.3 Hz), 8.16(1H, d, J = 7.9 Hz), 8.26(1H, s), 9.65(1H, s), 11.71(1H, s), 12.27-12.55(2H, m).<br>m.p.: 250.8° C. |
| 13 | ESI+: 758 |
| 14 | APCI/ESI+: 716<br>NMR: 1.12(3H, t, J = 7.2 Hz), 1.23-1.70(4H, m), 1.70-1.88(4H, m), 2.64-2.81 (4H, m), 2.84-3.01(4H, m), 3.32-3.44(2H, m), 7.18(2H, d, J = 8.5 Hz), 7.35 (2H, d, J = 8.2 Hz), 7.61(2H, d, J = 8.5 Hz), 7.73-7.79(1H, m), 7.85(2H, d, J = 8.2 Hz), 8.02(1H, d, J = 8.5 Hz), 8.10(1H, d, J = 7.9 Hz), 8.24(1H, s), 9.60(1H, s), 11.75(1H, s), 12.50-12.79(2H, m).<br>m.p.: 254.7° C. |
| 15 | ESI+: 772 |
| 16 | ESI+: 758 |

TABLE 56

| Ex | Data |
|---|---|
| 17 | APCI/ESI−: 728<br>NMR: 1.10-1.29(6H, m), 1.37-1.64(4H, m), 1.67-1.88(4H, m), 2.66-2.81(4H, m), 2.83-3.00(4H, m), 3.88-4.00(1H, m), 7.18(2H, d, J = 8.5 Hz), 7.35(2H, d, J = 8.2 Hz), 7.61(2H, d, J = 8.5 Hz), 7.72-7.78(1H, m), 7.85(2H, d, J = 8.2 Hz), 8.06(1H, d, J = 8.4 Hz), 8.10(1H, d, J = 8.0 Hz), 8.29(1H, s), 8.59(1H, s), 9.59(1H, s), 11.76(1H, s), 12.43-12.87(2H, m).<br>m.p.: 261.4° C. |
| 18 | APCI/ESI+: 795 |
| 19 | ESI+: 794 |
| 20 | ESI+: 780 |
| 21 | ESI+: 752<br>NMR: 0.95(3H, t, J = 7.1 Hz), 1.69-1.86(4H, m), 2.64-2.78(4H, m), 2.83-2.99 (4H, m), 3.65(2H, q, J = 7.1 Hz), 7.17(2H, d, J = 8.5 Hz), 7.22(2H, d, J = 8.6 Hz), 7.34(2H, d, J = 8.3 Hz), 7.61(2H, d, J = 8.5 Hz), 7.68-7.77(2H, m), 7.85(2H, d, J = 8.3 Hz), 7.91(2H, d, J = 8.6 Hz), 8.12-8.18(2H, m), 9.70(1H, br-s), 11.66(1H, br-s), 12.93(2H, br-s).<br>m.p.: 159.4° C. |
| 22 | ESI+: 800 |
| 23 | ESI+: 772<br>NMR: 1.12(3H, t, J = 7.0 Hz), 1.25-1.54(6H, m), 1.71-1.95(8H, m), 2.04-2.14 (1H, m), 2.55-2.62(2H, m), 2.63-2.77(6H, m), 3.19(2H, q, J = 7.0 Hz), 3.51-3.63(1H, m), 7.17(2H, d, J = 8.5 Hz), 7.33(2H, d, J = 8.3 Hz), 7.63(2H, d, J = 8.5 Hz), 7.76(1H, dd, J = 7.8, 7.9 Hz), 7.87(2H, d, J = 8.3 Hz), 8.06(1H, d, J = 7.9 Hz), 8.11(1H, d, J = 7.8 Hz), 8.27(1H, s), 9.69(1H, s), 11.67(1H, s), 12.20-12.60(2H, m).<br>m.p.: 178.5° C. |
| 24 | ESI+: 730 |
| 25 | ESI+: 716 |

TABLE 57

| Ex | Data |
|---|---|
| 26 | ESI+: 729 |
| 27 | ESI+: 715<br>NMR: 1.69-1.85(4H, m), 1.89(3H, s), 2.64-2.77(4H, m), 2.79-3.02(8H, m), 3.40-3.55(4H, m), 7.19(2H, d, J = 8.5 Hz), 7.36(2H, d, J = 8.2 Hz), 7.62(2H, d, J = 8.5 Hz), 7.79-7.89(3H, m), 7.95(1H, d, J = 7.9 Hz), 8.12-8.21(2H, m), 9.73(1H, s), 11.64(1H, s), 12.78(1H, s).<br>m.p.: 241.4° C. |
| 28 | ESI+: 706 |
| 29 | ESI+: 692 |
| 30 | ESI+: 796 |
| 31 | ESI+: 782 |
| 32 | ESI+: 658 |
| 33 | ESI+: 732 |
| 34 | ESI+: 744<br>0.64-0.77(4H, m), 1.39-1.58(4H, m), 1.69-1.87(4H, m), 2.02-2.09(1H, m), 2.20(2H, t, J = 7.0 Hz), 2.65-2.78(4H, m), 2.84-2.99(4H, m), 3.14(2H, t, J = 7.0 Hz), 7.18(2H, d, J = 8.5 Hz), 7.35(2H, d, J = 8.3 Hz), 7.60(2H, d, J = 8.5 Hz), 7.78-7.87(3H, m), 8.01-8.06(1H, m), 8.13-8.18(1H, m), 8.24-8.27 (1H, m), 9.65(1H, s), 11.71(1H, s), 11.90-12.90(2H, m)<br>m.p.: 220.1° C. |
| 35 | ESI;  597 |
| 36 | ESI;  617 |
| 37 | ESI+: 772 |
| 38 | ESI+: 800 |
| 39 | ESI+: 800 |
| 40 | ESI+: 816 |
| 41 | FAB−: 742 |
| 42 | ESI+: 772 |

TABLE 58

| Ex | Data |
|---|---|
| 43 | ESI+: 772 |
| 44 | ESI+: 702 |
| 45 | APCI/ESI−: 702 |
| 46 | APCI/ESI+: 718 |
| 47 | ESI+: 732 |
| 48 | ESI+: 716 |
| 49 | ESI+: 716 |
| 50 | FAB−: 736 |
| 51 | ESI+: 808 |
| 52 | ESI+: 758 |

TABLE 58-continued

| Ex | Data |
|---|---|
| 53 | ESI+: 758 |
| 54 | ESI+: 758 |
| 55 | |
| 56 | ESI+: 857 |
| 57 | ESI+: 859 |
| 58 | ESI+: 780 |
| 59 | ESI+: 786 |
| 60 | |
| 61 | ESI+: 788 |
| 62 | APCI/ESI+: 718 |
| 63 | ESI+: 774 |

TABLE 58-continued

| Ex | Data |
|---|---|
| 64 | ESI+: 744 |
| 65 | ESI+: 760 |
| 66 | APCI/ESI−: 700 |
| 67 | APCI/ESI+: 718 |
| 68 | ESI+: 772 |

TABLE 59

| Ex | Data |
|---|---|
| 69 | ESI+: 730 |
| 70 | ESI+: 744 |
| 71 | ESI+: 758 |
| 72 | APCI/ESI−: 728 |
| 73 | APCI/ESI+: 795 |
| 74 | APCI/ESI+: 809 |
| 75 | APCI/ESI+: 809 |
| 76 | ESI+: 766 |
| 77 | FAB+: 794 |
| 78 | ESI+: 808 |
| 79 | ESI+: 794 |
| 80 | ESI+: 724 |
| 81 | ESI+: 766 |
| 82 | ESI+: 766 |
| 83 | ESI+: 766 |

TABLE 59-continued

| Ex | Data |
|---|---|
| 84 | ESI+: 766 |
| 85 | ESI+: 767 |
| 86 | ESI+: 767 |
| 87 | ESI+: 767 |
| 88 | ESI+: 767 |
| 89 | ESI+: 738 |
| 90 | ESI−: 714 |
| 91 | ESI+: 788 |
| 92 | ESI+: 772 |
| 93 | ESI+: 815 |
| 94 | ESI+: 817 |

TABLE 60

| Ex | Data |
|---|---|
| 95 | ESI+: 786 |
| 96 | ESI+: 814 |
| 97 | ESI+: 830 |
| 98 | ESI+: 788 |
| 99 | ESI+: 780 |
| 100 | ESI+: 822 |
| 101 | ESI+: 758 |
| 102 | FAB+: 786<br>NMR: 0.81(3H, t, J = 7.4 Hz), 1.26-1.60(8H, m), 1.70-1.94(8H, m), 2.04-2.14 (1H, m), 2.55-2.63(2H, m), 2.64-2.78(6H, m), 3.04-3.11(2H, m), 3.49-3.59 (1H, m), 7.16(2H, d, J = 8.5 Hz), 7.33(2H, d, J = 8.3 Hz), 7.63(2H, d, J = 8.5 Hz), 7.77(1H, dd, J = 7.9, 8.0 Hz), 7.87(2H, d, J = 8.3 Hz), 8.06(1H, d, J = 8.0 Hz), 8.11(1H, d, J = 7.9 Hz), 8.25(1H, s), 9.68(1H, s), 11.68(1H, s), 12.10-12.80(2H, m).<br>m.p.: 191.4° C. |
| 103 | ESI+: 802 |
| 104 | ESI+: 752 |
| 105 | ESI+: 780 |
| 106 | ESI+: 746 |
| 107 | FAB−: 742 |
| 108 | ESI+: 743 |
| 109 | ESI+: 729 |
| 110 | ESI+: 672 |
| 111 | ESI+: 766 |
| 112 | ESI+: 630 |
| 113 | ESI+: 633 |
| 114 | ESI+: 647 |

TABLE 61

| Ex | Data |
|---|---|
| 115 | ESI+: 686 |
| 116 | ESI+: 645 |
| 117 | ESI+: 643 |
| 118 | ESI+: 638 |
| 119 | ESI+: 617 |
| 120 | ESI+: 577 |
| 121 | ESI+: 573 |
| 122 | ESI+: 556 |
| 123 | ESI+: 572 |
| 124 | ESI+: 590 |
| 125 | ESI+: 554 |
| 126 | ESI+: 588 |
| 127 | ESI+: 586 |
| 128 | ESI+: 568 |
| 129 | ESI+: 540 |
| 130 | ESI+: 574 |
| 131 | ESI+: 570 |
| 132 | ESI+: 631 |
| 133 | ESI+: 574 |
| 134 | ESI+: 568 |
| 135 | ESI+: 570 |
| 136 | ESI+: 574 |
| 137 | ESI+: 598 |
| 138 | ESI+: 574 |

TABLE 61-continued

| Ex | Data |
|---|---|
| 139 | ESI+: 602 |
| 140 | ESI+: 634 |

TABLE 62

| Ex | Data |
|---|---|
| 141 | ESI+: 582 |
| 142 | ESI+: 584 |
| 143 | ESI+: 616 |

TABLE 62-continued

| Ex | Data |
|---|---|
| 144 | ESI+: 542 |
| 145 | ESI+: 514 |
| 146 | ESI+: 542 |
| 147 | ESI+: 625 |
| 148 | ESI+: 623 |
| 149 | ESI+: 571 |
| 150 | ESI+: 568 |
| 151 | ESI+: 565 |
| 152 | ESI+: 500 |
| 153 | ESI+: 486 |

TABLE 63

| Pr | Structure | Data |
|---|---|---|
| 1 | methyl 4-{2-[4-aminophenyl]ethyl}benzoate | EI: 255 |
| 2 | methyl 4-{3-[4-aminophenyl]propyl}benzoate | ESI+: 270 |
| 3 | methyl 4-(2-{4-[(cyanoacetyl)amino]phenyl}ethyl)benzoate | ESI+: 323 |
| 4 | methyl 4-(3-{4-[(cyanoacetyl)amino]phenyl}propyl)benzoate | ESI+: 337 |

TABLE 63-continued
| Pr | Structure | Data |
|---|---|---|
| 5 | 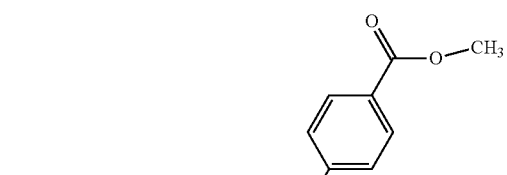 | ESI+: 435 |
TABLE 64
| Pr | Structure | Data |
|---|---|---|
| 6 | 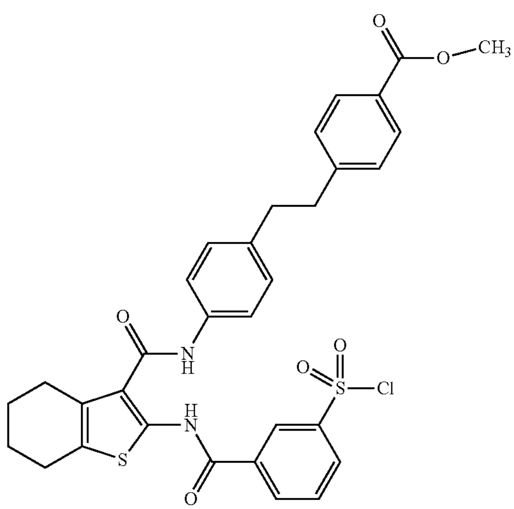 [SMILES: COC(=O)c1ccc(CCc2ccc(NC(=O)c3c(NC(=O)c4cccc(S(=O)(=O)Cl)c4)sc4c3CCCC4)cc2)cc1] | FAB−: 635, 637 |
| 7 | 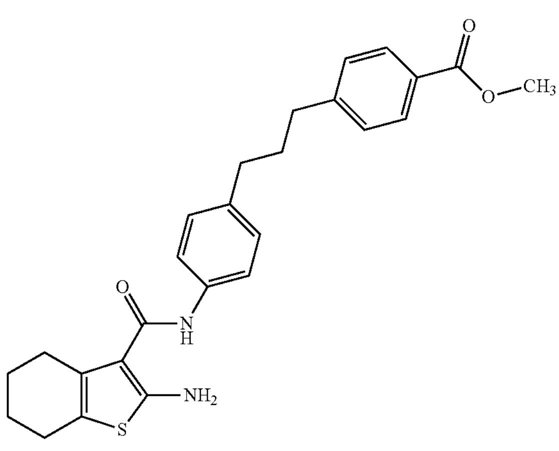 [SMILES: COC(=O)c1ccc(CCCc2ccc(NC(=O)c3c(N)sc4c3CCCC4)cc2)cc1] | ESI+: 449 |

TABLE 64-continued

| Pr | Structure | Data |
|---|---|---|
| 8 | 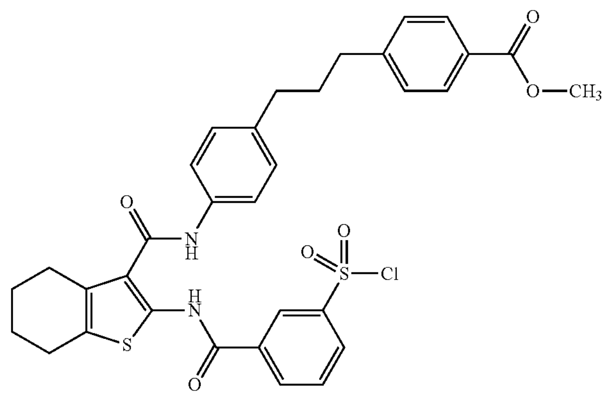 [SMILES: COC(=O)c1ccc(CCCc2ccc(NC(=O)c3c(NC(=O)c4cccc(S(=O)(=O)Cl)c4)sc4c3CCCC4)cc2)cc1] | ESI−: 649 |
| 9 | 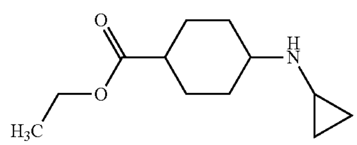 | ESI+: 212 |

TABLE 65

| Pr | Structure | Data |
|---|---|---|
| 9-1 | 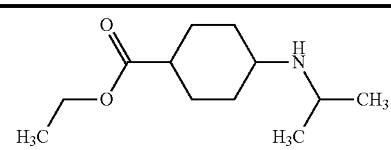 | ESI+: 214 |
| 10 | 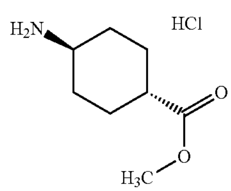 | FAB+: 158 |
| 11 | 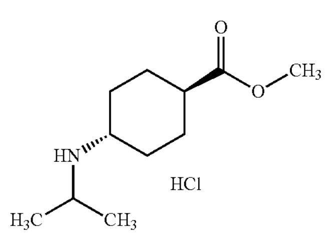 | ESI+: 200 |
| 12 | 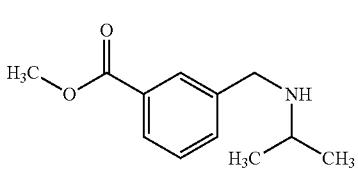 | ESI+: 208 |
| 13 | 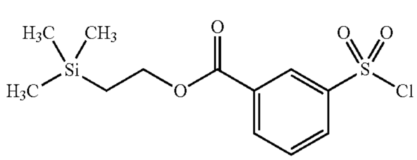 [SMILES: C[Si](C)(C)CCOC(=O)c1cccc(S(=O)(=O)Cl)c1] | EI: 319, 321 |

TABLE 65-continued

| Pr | Structure | Data |
|---|---|---|
| 14 | 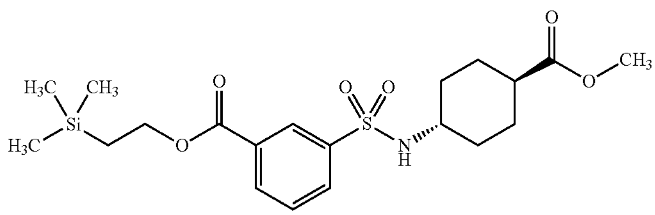 | FAB−: 440 |
| 15 | 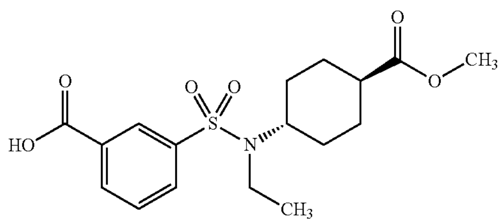 [SMILES: CCN([C@H]1CC[C@H](C(=O)OC)CC1)S(=O)(=O)c1cccc(C(=O)O)c1] | ESI+: 370 |

TABLE 66

| Pr | Structure | Data |
|---|---|---|
| 15-1 | 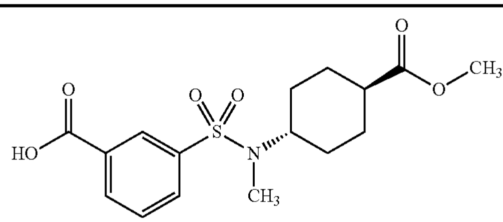 | ESI+: 356 |
| 15-2 | 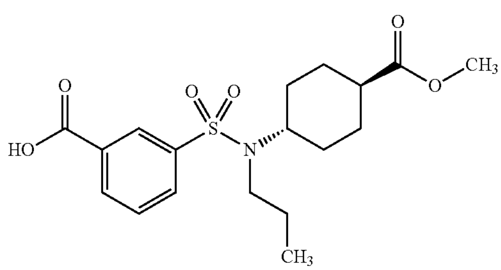 [SMILES: CCCN([C@H]1CC[C@H](C(=O)OC)CC1)S(=O)(=O)c1cccc(C(=O)O)c1] | ESI+: 384 |
| 16 | 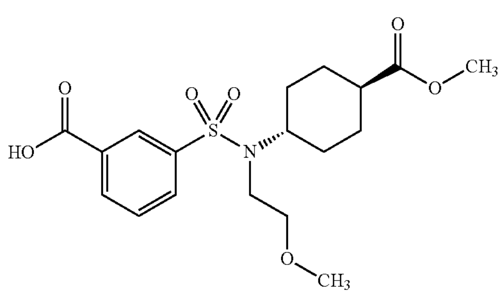 [SMILES: COCCN([C@H]1CC[C@H](C(=O)OC)CC1)S(=O)(=O)c1cccc(C(=O)O)c1] | ESI+: 400 |
| 17 | 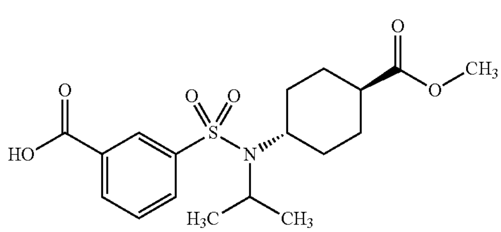 [SMILES: COC(=O)[C@H]1CC[C@H](N(C(C)C)S(=O)(=O)c2cccc(C(=O)O)c2)CC1] | ESI+: 384 |

TABLE 66-continued
| Pr | Structure | Data |
|---|---|---|
| 18 | 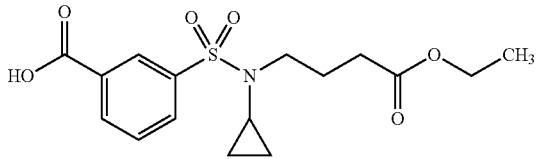 [SMILES: CCOC(=O)CCCN(C1CC1)S(=O)(=O)c1cccc(C(=O)O)c1] | ESI+: 356 |
| 18-1 | 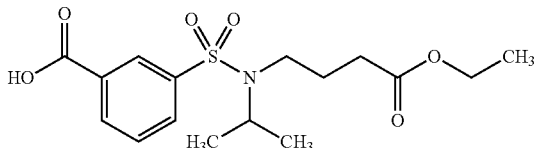 | ESI+: 358 |
TABLE 67
| Pr | Structure | Data |
|---|---|---|
| 19 | 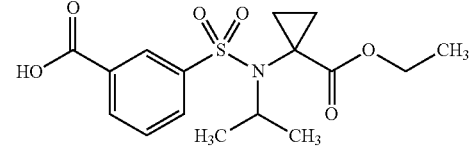 [SMILES: CCOC(=O)C1(N(C(C)C)S(=O)(=O)c2cccc(C(=O)O)c2)CC1] | ESI+: 356 |
| 19-1 | 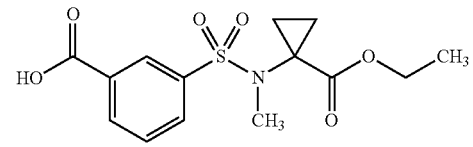 [SMILES: CCOC(=O)C1(N(C)S(=O)(=O)c2cccc(C(=O)O)c2)CC1] | ESI+: 328 |
| 19-2 | 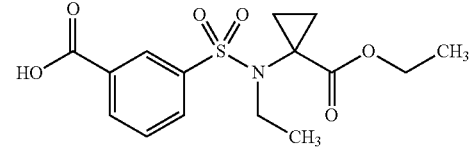 [SMILES: CCOC(=O)C1(N(CC)S(=O)(=O)c2cccc(C(=O)O)c2)CC1] | ESI+: 342 |
| 19-3 | 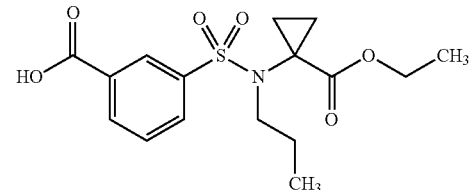 | ESI+: 356 |
| 20 | 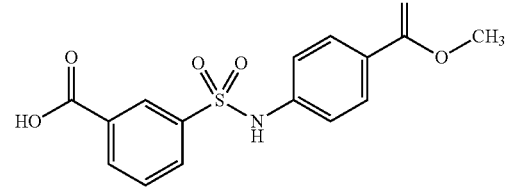 | ESI+: 336 |
| 21 | 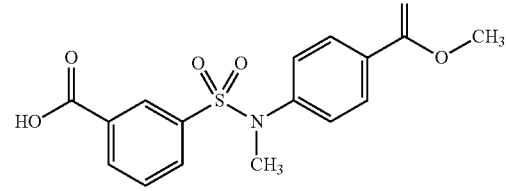 | ESI+: 350 |

TABLE 67-continued

| Pr | Structure | Data |
|---|---|---|
| 22 | 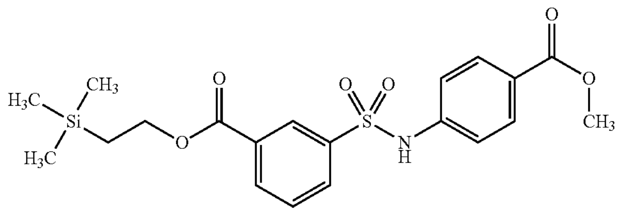 | ESI+: 458 [M + Na]+ |

TABLE 68

| Pr | Structure | Data |
|---|---|---|
| 22-1 | 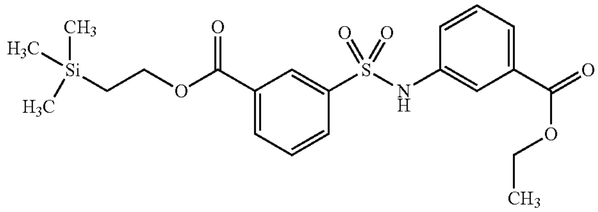 [SMILES: CCOC(=O)c1cccc(NS(=O)(=O)c2cccc(C(=O)OCC[Si](C)(C)C)c2)c1] | ESI+: 450 |
| 23 | 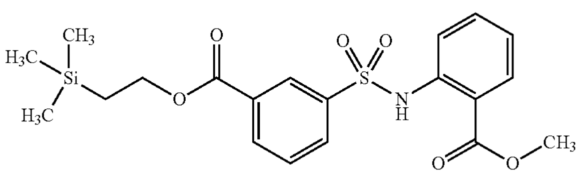 | ESI+: 436 |
| 23-1 | 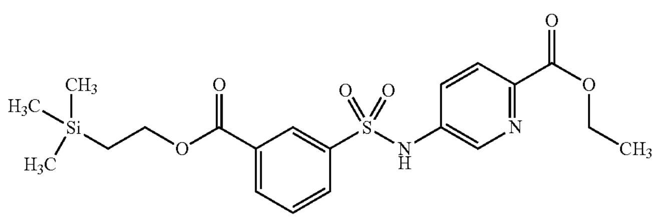 [SMILES: CCOC(=O)c1ccc(NS(=O)(=O)c2cccc(C(=O)OCC[Si](C)(C)C)c2)cn1] | ESI+: 451 |
| 24 | 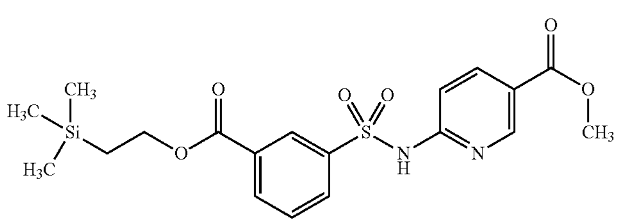 | ESI−: 435 |
| 25 | 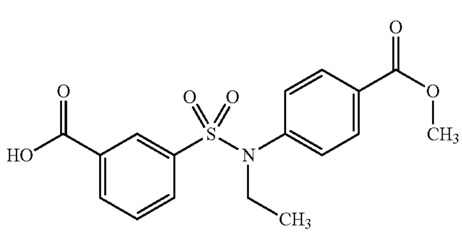 [SMILES: CCN(c1ccc(C(=O)OC)cc1)S(=O)(=O)c1cccc(C(=O)O)c1] | ESI+: 364 |

TABLE 68-continued

| Pr | Structure | Data |
|---|---|---|
| 25-1 | 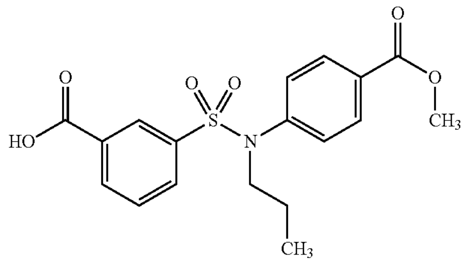 [SMILES: CCCN(c1ccc(C(=O)OC)cc1)S(=O)(=O)c1cccc(C(=O)O)c1] | ESI+: 378 |

TABLE 69

| Pr | Structure | Data |
|---|---|---|
| 25-2 | 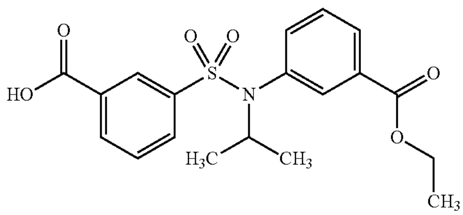 [SMILES: CCOC(=O)c1cccc(N(C(C)C)S(=O)(=O)c2cccc(C(=O)O)c2)c1] | ESI+: 392 |
| 25-3 | 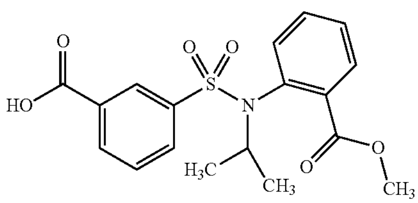 [SMILES: COC(=O)c1ccccc1N(C(C)C)S(=O)(=O)c1cccc(C(=O)O)c1] | ESI+: 378 |
| 26 | 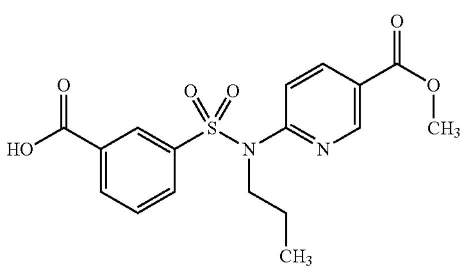 | ESI+: 379 |
| 26-1 | 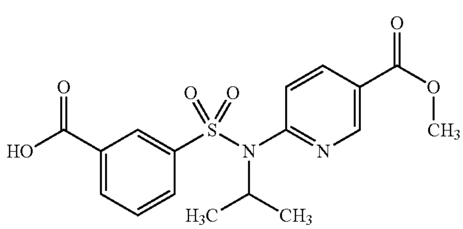 [SMILES: COC(=O)c1ccc(N(C(C)C)S(=O)(=O)c2cccc(C(=O)O)c2)nc1] | APCI/ESI+: 379 |
| 26-2 | 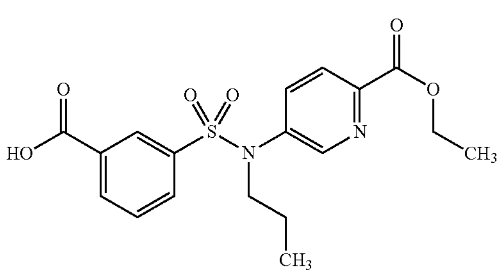 [SMILES: CCCN(c1ccc(C(=O)OCC)nc1)S(=O)(=O)c1cccc(C(=O)O)c1] | ESI+: 393 |

TABLE 69-continued

| Pr | Structure | Data |
|---|---|---|
| 26-3 | [structure] | ESI+: 393 |

TABLE 70

| Pr | Structure | Data |
|---|---|---|
| 27 | [structure] | ESI+: 257 |
| 27-1 | [structure] | ESI+: 259 |
| 28 | [structure] | ESI+: 303 |
| 29 | [structure] | ESI+: 252 |
| 30 | [structure] | ESI+: 364 |

INDUSTRIAL APPLICABILITY

The compound of the formula (I) or a salt thereof, or the compound of the formula (I) or a salt thereof has an NPT-IIb inhibitory action and can be used as an agent for preventing or treating hyperphosphatemia.

The invention claimed is:
1. A compound of the formula (I) or a salt thereof:

(I)

wherein
$R^1$ represents —O-lower alkyl, -lower alkylene-phenyl, or -lower alkylene-pyridyl, in which phenyl or pyridyl may be substituted with carboxy or —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—NH$_2$, —CO—NH-lower alkyl, —CO—N(lower alkyl)$_2$, —CO—N(lower alkyl)-aryl, —CO—N (lower alkyl)-(lower alkylene-aryl), —CO—NH-lower alkylene-OH, —CO—NH-lower alkylene-CO$_2$H, —CO—O-methyl, —CO—O-ethyl, or —COO-tert-butyl, $R^2$ and $R^3$ are the same or different and each independently represents H, lower alkyl, cycloalkyl, aryl, heteroaryl, nitrogen-containing saturated hetero ring, -lower alkylene-aryl, or -lower alkylene-heteroaryl, in which lower alkyl, cycloalkyl, aryl, heteroaryl, and a nitrogen-containing saturated hetero ring may be substituted with halogen, -lower alkyl, pyridyl, carboxy, —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—NH, —CO—NH-lower alkyl, —CO—N(lower alkyl)$_2$, —CO—N(lower alkyl)-aryl, —CO—N(lower alkyl)-lower alkylene-aryl), —CO—NH-lower alkylene-OH, —CO—NH-lower alkylene-CO$_2$H, —CO—O-methyl, —CO—O-ethyl, —COO-tert-butyl, amino which may be substituted with one -lower alkyl, or the same or different two or more -lower alkyls, —O-lower alkyl, —[CH(—OH)]$_m$—H or —OH, or $R^2$ and $R^3$ may be combined with the nitrogen atom to which they bind to form 5- to 7-membered saturated cyclic amino, in which the 5- to 7-membered saturated cyclic amino may be substituted with halogen, —OH, oxo(=O), —O-lower alkyl, cyano, nitro, cycloalkyl, aryl, hetero ring, -lower alkylene-aryl, -lower alkylene-hetero ring, -lower alkyl which may be substituted with halogen, —OH, —O-lower alkyl, or cyano, carboxy, —CO—O-lower alkyl, —CO—O-lower alkenyl, —CO—O-lower alkynyl, —CO—O-lower alkylene-O-lower alkyl, —CO—O-lower alkyelen-aryl, —CO—O-lower alkylene-O-aryl, —CO—NH$_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-CO$_2$H, —CO—O-methyl, —CO—O-ethyl, —COO-tert-butyl or —CO-lower alkyl, $R^4$'s are the same as or different and each independently represents halogen, lower alkyl, —OH, —O-lower alkyl, —NO$_2$, or a group represented by the formula (II):

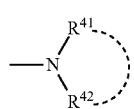

(II)

wherein $R^{41}$ and $R^{42}$ are the same or different and each independently represents H or lower-alkyl which may be substituted with —OH, or $R^{41}$ and $R^{42}$ may be combined with the nitrogen atom to which they bind to form 5- to 7-membered saturated cyclic amino, and m represents 1 to 5, and n represents 0 to 2, provided that N-(4-methoxyphenyl)-2-({3-[(4-methylpiperazin-1-yl)sulfonyl]benzoyl}amino)-4,5,6,7-tetrahydro-1-benzothiophene-3-carboxamide is excluded.

2. The compound or a salt thereof according to claim 1, wherein n is 0.

3. The compound or a salt thereof according to claim 2, wherein $R^1$ is -lower alkylene-(phenyl substituted with carboxy or —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—NH$_2$, —CO—NH-lower alkyl, —CO—N(lower alkyl)), —CO—N(lower alkyl)-aryl, —CO—N(lower alkyl)-(lower alkylene-aryl), —CO—NH-lower alkylene-OH, —CO—NH-lower alkylene-CO$_2$H, —CO—O-methyl, —CO—O-ethyl, or —COO-tert-butyl).

4. The compound or a salt thereof according to claim 3, wherein $R^1$ is -lower alkylene-(phenyl substituted with carboxy).

5. The compound or a salt thereof according to claim 4, wherein $R^2$ is -lower alkyl, cycloalkyl, or phenyl, each of which is substituted with carboxy.

6. The compound or a salt thereof according to claim 5, wherein $R^3$ is -lower alkyl or cycloalkyl.

7. The compound or a salt thereof according to claim 6, wherein $R^2$ and $R^3$ are combined with the nitrogen atom to which they bind to form pyrrolidin-1-yl, piperidin-1-yl, piperazin-1-yl, morpholin-4-yl, or azepan-1-yl, each of which may be substituted with halogen, —OH, oxo(=O), —O—lower-alkyl, cyano, nitro, cycloalkyl, aryl, hetero ring, -lower alkylene-aryl, -lower alkylene-hetero ring, -lower alkyl which may be substituted with halogen, —OH, —O-lower alkyl, or cyano, carboxy, —CO—O-lower alkyl, —CO—O-lower -alkenyl, —CO—O-lower alkynyl, —CO—O-lower alkylene-O-lower alkyl, —CO—O-lower alkylene-aryl, —CO—O-lower alkylene-O-aryl, —CO—NH$_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-CO$_3$H, —CO—O-methyl, —CO—O-ethyl, —COO-tert-butyl or —CO-lower alkyl.

8. The compound or a salt thereof according to claim 7, wherein $R^2$ and $R^3$ are combined with the nitrogen atom to which they bind to form piperazin-1-yl which may be substituted with halogen, —OH, oxo(=O), —O-lower alkyl, cyano, nitro, cycloalkyl, aryl, hetero ring, -lower alkylene-aryl, -lower alkylene-hetero ring, -lower alkyl which may be substituted with halogen, —OH, —O-lower alkyl, or cyano, carboxy, —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—NH), —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-CO$_2$H, —CO—O-methyl, —CO—O-ethyl, —COO-tert-butyl or —CO-lower alkyl.

9. A pharmaceutical composition, comprising a compound or a salt thereof according to claim 1, and a pharmaceutically acceptable excipient.

* * * * *